(12) United States Patent
Naidu et al.

(10) Patent No.: US 7,897,593 B2
(45) Date of Patent: Mar. 1, 2011

(54) HIV INTEGRASE INHIBITORS

(75) Inventors: B. Narasimhulu Naidu, Durham, CT (US); Margaret E. Sorenson, Meriden, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 572 days.

(21) Appl. No.: 11/754,462

(22) Filed: May 29, 2007

(65) Prior Publication Data
US 2007/0281917 A1 Dec. 6, 2007

Related U.S. Application Data

(60) Provisional application No. 60/809,194, filed on May 30, 2006.

(51) Int. Cl.
| | |
|---|---|
| *A61P 31/00* | (2006.01) |
| *A61K 31/54* | (2006.01) |
| *A61K 31/55* | (2006.01) |
| *A61K 31/535* | (2006.01) |
| *C07D 403/00* | (2006.01) |
| *C07D 498/00* | (2006.01) |

(52) U.S. Cl. ............ 514/210.02; 514/210.21; 514/212.08; 514/217.06; 514/228.5; 514/230.2; 540/524; 540/600; 544/61; 544/71

(58) Field of Classification Search ............ 514/210.02, 514/210.21, 212.08, 217.06, 228.5, 230.2; 540/524, 600; 544/61, 71
See application file for complete search history.

(56) References Cited

U.S. PATENT DOCUMENTS

| | | |
|---|---|---|
| 7,037,908 B2 | 5/2006 | Naidu et al. |
| 7,115,601 B2 | 10/2006 | Naidu et al. |
| 7,135,467 B2 | 11/2006 | Walker et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,273,859 B2 | 9/2007 | Naidu |
| 2006/0046985 A1 | 3/2006 | Crescenzi et al. |

FOREIGN PATENT DOCUMENTS

| | | |
|---|---|---|
| EP | 1698628 A1 | 9/2006 |
| WO | WO 2005/061490 A1 | 7/2005 |
| WO | WO 2005/061501 A2 | 7/2005 |
| WO | WO 2006/103399 A1 | 10/2006 |
| WO | WO 2006/121831 A2 | 11/2006 |

OTHER PUBLICATIONS

U.S. Appl. No. 11/599,580, filed Nov. 14, 2006, B. Narasimhulu Naidu.
U.S. Appl. No. 11/768,458, filed Jun. 26, 2007, Michael A. Walker, et al.
U.S. Appl. No. 11/511,751, filed Aug. 29, 2006, Jacques Banville, et al.
U.S. Appl. No. 11/561,039, filed Nov. 17, 2006, B. Narasimhulu Naidu, et al.
U.S. Appl. No. 11/595,429, filed Nov. 10, 2006, B. Narasimhulu Naidu, et al.
U.S. Appl. No. 11/590,637, filed Oct. 31, 2006, B. Narasimhulu Naidu.

*Primary Examiner*—Brenda L Coleman
(74) *Attorney, Agent, or Firm*—James Epperson

(57) ABSTRACT

The invention encompasses series bicyclic pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

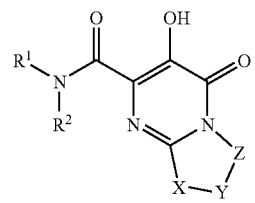

11 Claims, No Drawings

HIV INTEGRASE INHIBITORS

CROSS REFERENCE TO RELATED APPLICATIONS

This application claims the benefit of U.S. Provisional Application Ser. No. 60/809,194, filed May 30, 2006.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. N. Engl. J. Med. 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. JAMA 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. Science 2000, 287, 646). And recently, HIV integrase inhibitors have been accepted into clinical trials for treating AIDS and HIV infection (Neamati Expert. Opin. Ther. Patents 2002, 12, 709, Pais and Burke Drugs Fut. 2002, 27, 1101).

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

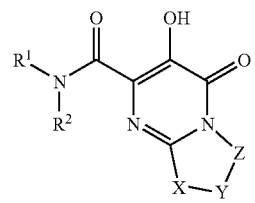

where:

$R^1$ is $(Ar_1)$alkyl;

$R^2$ is hydrogen, alkyl, hydroxy, or alkoxy;

$R^3$ is hydrogen, halo, hydroxy, cyano, alkyl, cycloalkyl, haloalkyl, alkoxy, haloalkoxy, $CON(R^6)(R^6)$, $CON(R^{11})(R^{12})$, $SOR^7$, $SO_2R^7$, $SO_2N(R^6)(R^6)$, $SO_2N(R^{11})(R^{12})$, $N(R^6)(R^6)$, $N(R^6)(R^6)$, $N(R^6)COR^7$, $N(R^6)CO_2R^7$, $N(R^6)SO_2R^7$, $PO(OR^6)_2$, $R^{16}$, or $Ar^2$;

$R^4$ is hydrogen, halo, hydroxy, cyano, alkyl, alkoxy, haloalkyl, or haloalkoxy;

$R^5$ is hydrogen, halo, hydroxy, cyano, alkyl, alkoxy, haloalkyl, or haloalkoxy;

$R^6$ is hydrogen or alkyl;

$R^7$ is alkyl or cycloalkyl;

$R^8$ and $R^9$ taken together is $CH_2N(R^{10})CH_2$, $CH_2N(R^{10})CH_2CH_2$, $CH_2N(R^{10})CH_2CH_2CH_2$, $CH_2N(R^{10})CH_2CH_2CH_2CH_2$, $CH_2CH_2N(R^{10})CH_2CH_2$, or $CH_2CH_2N(R^{10})CH_2CH_2CH_2$;

$R^{10}$ is $COR^6$, $CO_2(R^6)$, $COCO_2(R^6)$, $CON(R^6)(R^6)$, $COCON(R^6)(R^6)$, $CO_2(benzyl)$, $CO(phenyl)$, $SO_2R^7$, $SO_2N(R^6)(R^6)$, or $SO_2(phenyl)$ where the phenyl is substituted with 0-2 groups selected from alkyl, halo, haloalkyl, cyano, alkoxy, and haloalkoxy;

or $R^{10}$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of oxo, halo, alkyl, and alkoxy;

$R^{11}$ and $R^{12}$ taken together with the nitrogen to which they are attached is azetidinyl, pyrrolidinyl, $(R^6)$-piperidinyl, piperazinyl, dialkylpiperazinyl, $(R^{13})$-piperazinyl, $(R^{13})$-dialkylpiperazinyl, homopiperidinyl, morpholinyl, dialkylmorpholinyl, or thiomorpholinyl;

$R^{13}$ is alkyl, (cycloalkyl)alkyl, $SO_2R^{14}$, or $COR^{15}$;

$R^{14}$ is hydrogen, alkyl, amino, alkylamino, dialkylamino, azetidinyl, pyrrolidinyl, piperidinyl, hydroxypiperidinyl, piperizinyl, (alkyl)piperizinyl, morpholinyl, or thiomorpholinyl;

$R^{15}$ hydrogen, alkyl, hydroxy, alkoxy, amino, alkylamino, dialkylamino, azetidinyl, pyrrolidinyl, piperidinyl, hydroxypiperidinyl, piperizinyl, (alkyl)piperizinyl, morpholinyl, or thiomorpholinyl;

$R^{16}$ azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

$Ar^1$ is

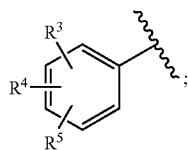

$Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of oxo, halo, alkyl, alkoxy, and $N(R^6)(R^6)$; and X—Y—Z is $C(R^8)(R^9)OCH_2$, $C(R^8)(R^9)OCH_2CH_2$, $C(R^8)(R^9)OCH_2CH_2CH_2$, $C(R^8)(R^9)N(R^6)CH_2$, $C(R^8)(R^9)N(R^6)CH_2CH_2$, $C(R^8)(R^9)N(R^6)CH_2CH_2CH_2$, $C(R^8)(R^9)N(R^1)CH_2$, $C(R^8)(R^9)N(R^1)CH_2CH_2$, or $C(R^8)(R^9)N(R^1)CH_2CH_2CH_2$;

or a pharmaceutically acceptable salt thereof.

Another aspect of the invention is a compound of formula I as above but where $R^{10}$ is $CO_2(R^6)$, $COCO_2(R^6)$, $CON(R^6)(R^6)$, $COCON(R^6)(R^6)$, $CO_2$(benzyl), CO(phenyl), $SO_2R^7$, $SO_2N(R^6)(R^6)$, or $SO_2$(phenyl) where the phenyl is substituted with 0-2 groups selected from alkyl, halo, haloalkyl, cyano, alkoxy, and haloalkoxy;

$R^{11}$ and $R^{12}$ taken together with the nitrogen to which they are attached is azetidinyl, pyrrolidinyl, ($R^6$)-piperidinyl, piperazinyl, ($R^{13}$)-piperazinyl, homopiperidinyl, morpholinyl, or thiomorpholinyl; and X—Y—Z is $C(R^8)(R^9)OCH_2$, $C(R^8)(R^9)OCH_2CH_2$, or $C(R^8)(R^9)OCH_2CH_2CH_2$;

or a pharmaceutically acceptable salt thereof.

Another aspect of the invention is a compound of Formula I according one of the following structures.

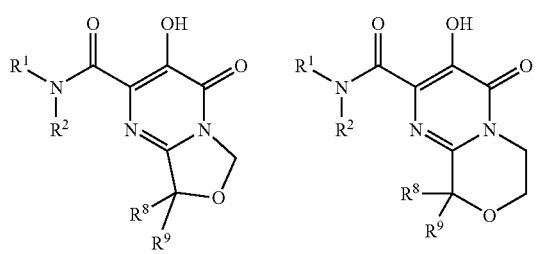

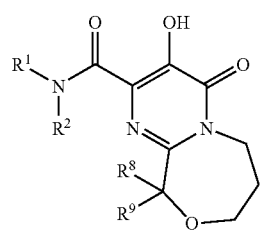

Another aspect of the invention is a compound of Formula I where $R^1$ is ($Ar^1$)methyl.

Another aspect of the invention is a compound of Formula I where $R^1$ is

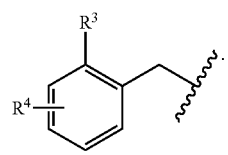

Another aspect of the invention is a compound of Formula I where $R^1$ is

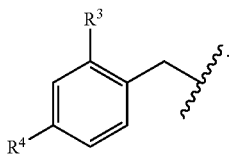

Another aspect of the invention is a compound of Formula I where $R^2$ is hydrogen.

Another aspect of the invention is a compound of Formula I where $R^3$ is fluoro, chloro, methyl, $CON(R^6)(R^6)$, or $Ar^2$.

Another aspect of the invention is a compound of Formula I where $R^4$ is hydrogen, fluoro, chloro, or methyl.

Another aspect of the invention is a compound of Formula I where $R^5$ is hydrogen.

Another aspect of the invention is a compound of Formula I where $Ar^1$ is

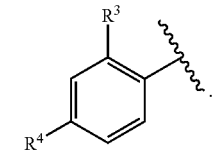

For a compound of Formula I, the scope of any variable, including $R^1$, $R^2$, $R^3$, $R^4$, $R^5$, $R^6$, $R^7$, $R^{10}$, $R^{11}$, $R^{12}$, $R^{13}$, $R^{14}$, $R^{15}$, $R^{16}$, $Ar^1$, $Ar^2$, $R^8$ and $R^9$ taken together, and X—Y—Z, can be used independently with any scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with an alkyl moiety include straight and branched isomers composed of 1 to 6 carbon atoms for the alkyl portion. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Some substituents are divalent and should be construed to attach in either of the two configurations.

"Dioxothiazinyl" means

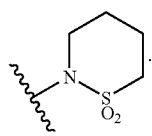

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

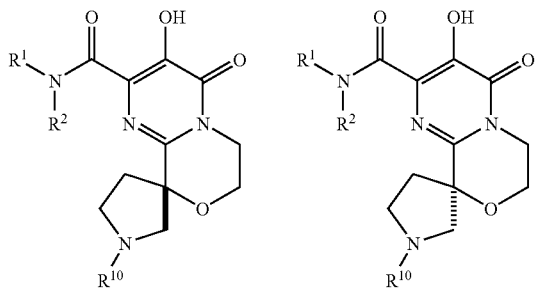

The invention includes all tautomeric forms of the compounds. An example of a tautomeric pair is shown below.

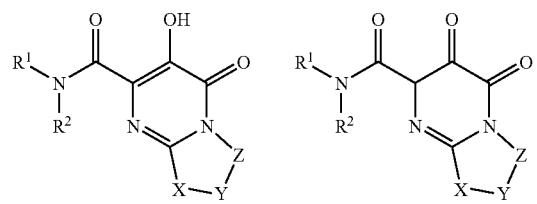

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

Scheme 1.

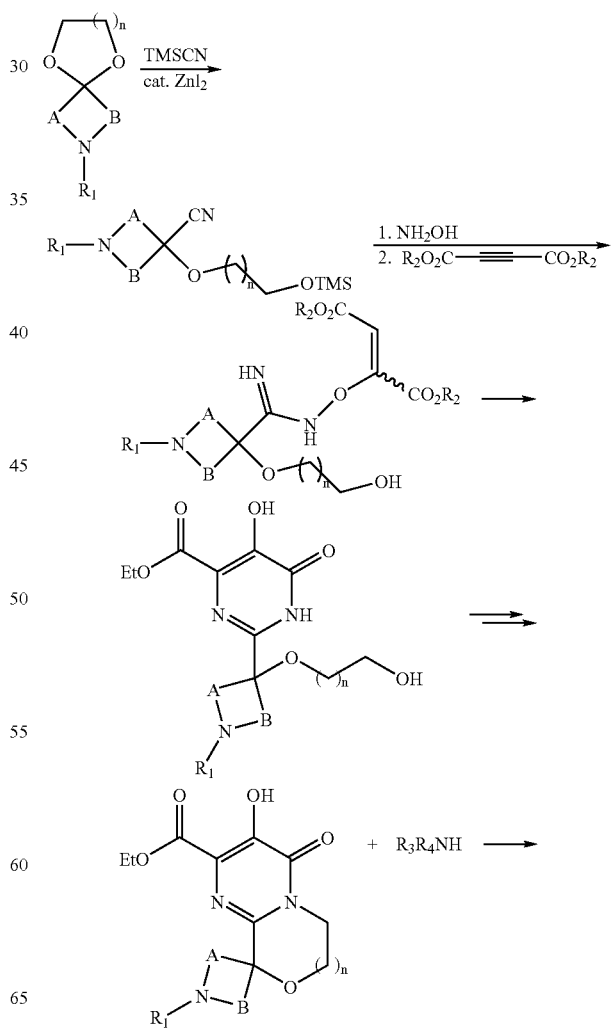

-continued

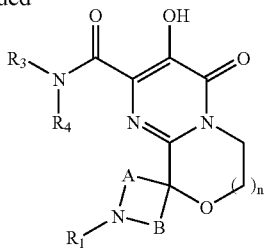

Biological Methods

HIV-Integrase InhibitionActivity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol* 69, 5908-5911 (1995). The sequences of substrate and target DNA were described in *Nucleic Acid Research* 22, 1121-1122 (1994). Results are shown in the Table 1. Activity equal to A refers to a compound having $IC_{50}=0.001$ to $0.01$ μM $B=0.01$-$0.1$, and $C \geq 0.1$ μM respectively.

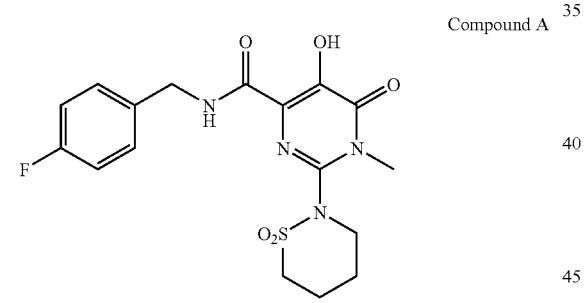

Compound A

HIV-Integrase binding assay. In this assay competitive binding experiments with test compounds and a radiolabeled integrase inhibitor (compound A) are performed against purified integrase. SPA bead/DNA/enzyme complexes were prepared as for the integrase inhibition assay except, to each well, 0.69 μl of integrase enzyme (0.42 mg/μl) was used per 2 μl of LTR DNA-attached scintillation proximity beads (stock 50 mg/ml). Binding reactions were carried out in 96-well white polystyrene assay plates (Corning, #3600). The following was added sequentially to each well: 20 μl of water or 20μl of human serum (Cellgro Cat# 35-060-CL), 5 μl of serially diluted compound (in 50% DMSO/50% integrase SPA buffer), 5 μl of [$^3$H]-compound I (6,000 cpm/μl in SPA buffer) and 20 μl of bead/DNA/enzyme complex. The plates were shaken for 2 hours and then allowed to sit at room temperature without shaking overnight. The [$^3$H]-compound I binding was measured using a Topcount scintillation counter. Cheng and Prusoff equations were used to convert the inhibition of compound 1 binding into the corresponding Ki value. Results are shown in the Table 1. Activity equal to A refers to a compound having $Ki=0.001$ to $0.003$ μM while B and C denote compounds having $Ki=0.003$ to $0.05$ μM and $Ki \geq 0.050$ μM respectively.

Inhibition of HIV replication. A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10 % FBS, 15 mg/ml human serum albumin/10 % FBS or 40% human serum/5% FBS, and the results from at least 2 experiments were used to calculate the $EC_{50}$ values. Results are shown in the Table 1. Activity $EC_{50}=0.001$-$0.01$ μM; $B=0.01$ to $0.1$ μM; and $EC_{50} \geq 0.1$ μM respectively.

TABLE 1

Biological data

| Example | Inhibition Activity | Binding Activity | Antiviral Activity |
|---------|---------------------|------------------|--------------------|
| 1 | A | | A |
| 2 | A | | A |
| 3 | A | | A |
| 4 | A | | A |
| 5 | A | | A |
| 6 | A | | A |
| 7 | A | | A |
| 8 | A | | A |
| 9 | B | | A |
| 10 | B | | A |
| 11 | A | | A |
| 12 | B | | A |
| 13 | B | | B |
| 14 | B | | A |
| 15 | B | | A |
| 16 | B | | A |
| 17 | B | | A |
| 18 | A | | A |
| 19 | A | | A |
| 20 | A | | A |
| 21 | B | | A |
| 22 | A | | A |
| 23 | B | | A |
| 24 | — | | — |
| 25 | C | | C |
| 26 | B | | B |
| 27 | B | | C |
| 28 | A | | B |
| 29 | A | | C |
| 30 | A | | B |
| 31 | A | | A |
| 32 | B | | C |
| 33 | A | | A |
| 34 | | B | B |
| 35 | | B | B |
| 36 | A | | A |
| 37 | B | | B |

TABLE 1-continued

Biological data

| Example | Inhibition Activity | Binding Activity | Antiviral Activity |
|---|---|---|---|
| 38 | A |   | B |
| 39 | B |   | B |
| 40 | A |   | B |
| 41 | B |   | C |
| 42 | A |   | A |
| 43 | B |   | B |
| 44 |   | A | B |
| 45 |   | A | B |
| 46 |   | B | C |
| 47 |   | B | C |
| 48 |   | A | B |
| 49 | B |   | B |
| 50 | B |   | B |
| 51 |   | B | A |
| 52 | B |   | B |
| 53 |   | B | A |
| 54 | B |   | B |
| 55 |   | B | A |
| 56 | B |   | B |
| 57 |   | A | A |
| 58 |   | A | A |
| 59 |   | A | A |
| 60 |   | A | A |
| 61 |   | A | A |
| 62 |   | B | B |
| 63 |   | B | B |
| 64 |   | B | A |
| 65 |   | B | A |
| 66 |   | B | A |
| 67 |   | B | B |
| 68 |   | B | B |
| 69 |   | B | C |
| 70 |   | B | B |
| 71 |   | B | B |
| 72 |   | B | B |
| 73 |   | B | C |
| 74 |   | B | C |
| 75 |   | B | B |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 10 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 10 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 3 lists some agents useful in treating AIDS and HIV infection which are suitable for this invention.

TABLE 2

ANTIVIRALS

| Drug Name | Manufacturer | Indication |
| --- | --- | --- |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |

TABLE 2-continued

ANTIVIRALS

| Drug Name | Manufacturer | Indication |
|---|---|---|
| Adefovir dipivoxil | Gilead Sciences | HIV infection, ARC, |
| AL-721 | Ethigen | PGL HIV positive, |
| | (Los Angeles, CA) | AIDS |
| Alpha Interferon | Glaxo Wellcome | Kaposi's sarcoma |
| HIV in combination | | |
| w/Retrovir | | |
| Ansamycin | Adria Laboratories | ARC |
| LM 427 | (Dublin, OH) | |
| | Erbamont | |
| | (Stamford, CT) | |
| Antibody which | Advanced Biotherapy | AIDS, ARC |
| Neutralizes pH | Concepts | |
| Labile alpha aberrant | (Rockville, MD) | |
| Interferon | | |
| AR177 | Aronex Pharm | HIV infection, AIDS, ARC |
| Beta-fluoro-ddA | Nat'l Cancer Institute | AIDS-associated diseases |
| BMS-232623 | Bristol-Myers Squibb/ | HIV infection, AIDS, |
| (CGP-73547) | Novartis | ARC |
| (protease inhibitor) | | |
| BMS-234475 | Bristol-Myers Squibb/ | HIV infection, AIDS, |
| (CGP-61755) | Novartis | ARC |
| (protease inhibitor) | | |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine | Pharmacia-Upjohn | HIV infection, AIDS, ARC |
| (RT inhibitor) | | |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combinationwith AZT/d4T |
| DMP-450 | AVID | HIV infection, AIDS, |
| (protease inhibitor) | (Camden, NJ) | ARC |
| Efavirenz | DuPont Merck | HIV infection, AIDS, |
| (DMP 266) | | ARC |
| (−)6-Chloro-4-(S)- | | |
| cyclopropylethynyl- | | |
| 4(S)-trifluoro- | | |
| methyl-1,4-dihydro- | | |
| 2H-3,1-benzoxazin- | | |
| 2-one, STOCRINE | | |
| (non-nucleoside RT | | |
| inhibitor) | | |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC |
| (reverse transcriptase inhibitor) | | |
| GS 840 | Gilead | HIV infection, AIDS, ARC |
| (reverse transcriptase inhibitor) | | |
| HBY097 | Hoechst Marion Roussel | HIV infection, AIDS, ARC |
| (non-nucleoside reverse transcriptaseinhibitor) | | |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC | Glaxo Wellcome | HIV infection, AIDS, ARC, also with AZT |
| (reverse transcriptase inhibitor) | | |
| Lobucavir | Bristol-Myers Squibb | CMV infection |
| Nelfinavir | Agouron Pharmaceuticals | HIV infection, AIDS, ARC |
| (protease inhibitor) | | |
| Nevirapine | Boeheringer Ingleheim | HIV infection, AIDS, ARC |
| (RT inhibitor) | | |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC |
| (protease inhibitor) | | |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC |
| (protease inhibitor) | | |
| Saquinavir | Hoffmann-LaRoche | HIV infection, AIDS, ARC |
| (protease inhibitor) | | |
| Stavudine; d4T Didehydrodeoxy-thymidine | Bristol-Myers Squibb | HIV infection, AIDS, ARC |
| Valaciclovir | Glaxo Wellcome | Genital HSV & CMVinfections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® | GSK | HIV infection, AIDS |
| (reverse transcriptase inhibitor) | | |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |

TABLE 3

IMMUNOMODULATORS

| Drug Name | Manufacturer | Indication |
| --- | --- | --- |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, in combination w/AZT ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

TABLE 4

ANTI-INFECTIVES

| Drug Name | Manufacturer | Indication |
| --- | --- | --- |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Description of Specific Embodiments

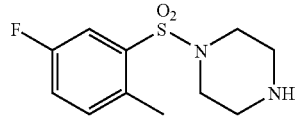

Intermediate 1

1-(5-Fluoro-2-methylphenylsulfonyl)Piperazine. To a stirred suspension of piperazine (28.4 g, 288 mmol) in triethylamine (42 mL, 300 mmol) and diethyl ether (500 mL) that was cooled to 0° C. was added dropwise a solution of 5-fluoro-2-methylbenzene sulfonylchloride (30 g, 144 mmol) dissolved in diethyl ether (50 mL). The resulting mixture was stirred at room temp for 2 h then diluted with EtOAc and saturated aqueous $NaHCO_3$. The organic phase was washed with water, brine and dried ($Na_2SO_4$). Concentration gave the title compound as a white solid (20.6 g, 55% yield). $^1$H NMR (300 MHz, $CDCl_3$) δ: 7.57 (1H, dd, J=8.6, 2.7 Hz), 7.25 (1H, dd, J=8.4, 5.1 Hz), 7.12 (1H, td, J=8.1, 2.8 Hz), 3.13-3.10 (4H, m), 2.98-2.85 (4H, m), 2.55 (3H, s), 1.69 (1H, bs). LCMS (M+H) calcd for $C_{11}H_{16}FN_2O_2S$: 259.09; found: 259.18.

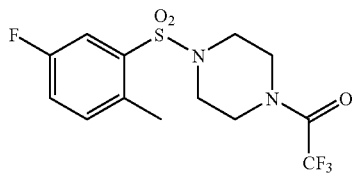

Intermediate 2

2,2,2-Trifluoro-1-(4-(5-fluoro-2-methylphenylsulfonyl) piperazin-1-yl)ethanone. To a solution of Intermediate 1 (20.6 g, 80 mmol) dissolved in methanol (40 mL) and triethylamine (11.2 mL, 80 mmol) was added trifluoroethyl acetate (12 mL, 100 mmol). The resulting mixture was stirred at room temp for 24 h and concentrated. The residue was partitioned between EtOAc and water and the organic phase was washed with 1N HCl, brine and dried ($Na_2SO_4$). Concentration gave the title compound as a white solid (28.3 g, 100% yield). $^1$H NMR (300 MHz, $CDCl_3$) δ: 7.58 (1H, dd, J=8.4, 2.9 Hz), 7.29 (1H, dd, J=8.4, 5.1 Hz), 7.18 (1H, td, J=8.0, 2.8 Hz), 3.76-3.73 (2H, m), 3.68-3.65 (2H, m), 3.28-3.23 (4H, m), 2.55 (3H, s). LCMS (M+H) calcd for $C_{13}H_{15}F_4N_2O_3S$: 355.07; found: 355.14.

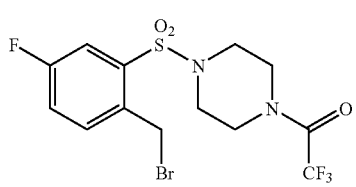

Intermediate 3

1-(4-(2-(Bromomethyl)-5-fluorophenylsulfonyl)piperazin-1-yl)-2,2,2-trifluoroethanone. To a solution of Intermediate 2 (9.5 g, 27 mmol) in $CCl_4$ (70 mL) was added AIBN (0.5 g, 3 mmol) and the mixture was brought to reflux. NBS (5.3 g, 30 mmol) was added and the mixture was refluxed for 4 h, cooled and filtered to remove solids. Concentration and purification by flash chromatography (0% to 25% EtOAc/hexane) gave the title compound as colorless oil (5.715 g, 49% yield). $^1$H NMR (300 MHz, $CDCl_3$) δ: 7.65-7.60 (2H, m), 7.33-7.27 (1H, m), 4.83 (2H, s), 3.82-3.79 (2H, m), 3.74-3.71 (2H, m), 3.34-3.30 (4H, m). LCMS (M+H) calcd for $C_{13}H_{14}BrF_4N_2O_3S$: 433.97; found: 435.11.

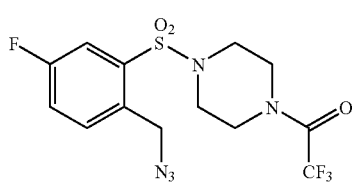

Intermediate 4

1-(4-(2-(Azidomethyl)-5-fluorophenylsulfonyl)piperazin-1-yl)-2,2,2-trifluoroethanone. To a solution of Intermediate 3 (10.86 g, 25 mmol) in DMF (150 mL) was added sodium azide (1.63 g, 25.10 mmol) and the mixture was stirred at 80° C. for 4 h. Then, the reaction mixture was concentrated to near dryness and the resulting residue was diluted with water and extracted with EtOAc. The organic phase was washed with brine, dried ($Na_2SO_4$) and concentrated to give the title compound as yellow oil that solidified to white solid upon standing (10.0 g, 100% yield). $^1$H NMR (300 MHz, $CDCl_3$) δ: 7.64-7.50 (2H, m), 7.37-7.31 (1H, m), 4.72 (2H, s), 3.79-3.75 (2H, m), 3.70-3.67 (2H, m), 3.29-3.26 (4H, m).

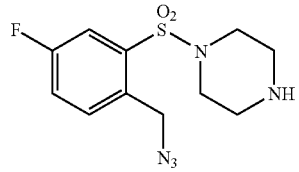

Intermediate 5

1-(2-(Azidomethyl)-5-fluorophenylsulfonyl)piperazine. To a solution of Intermediate 4 (0.50 g, 1.26 mmol) in MeOH (10 mL) was added KOH (0.35 g, 6.3 mmol). The mixture was stirred at room temp for 1 h and neutralized with 1N HCl and concentrated. The residue was triturated with ether and the solids were removed by filtration. The ethereal solution was concentrated to give the title compound as yellow oil (0.277 g, 73% yield). LCMS (M+H) calcd for $C_{11}H_{15}FN_5O_2S$: 300.09; found: 300.27.

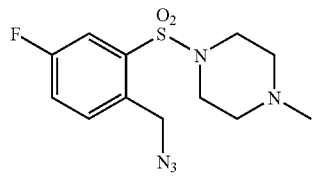

Intermediate 6

1-(2-(Azidomethyl)-5-fluorophenylsulfonyl)-4-methylpiperazine. To a solution of Intermediate 5 (7.0 g, 23 mmol) and triethylamine (11.10 mL, 80 mmol) in DCE (45 mL) was added 33 wt % aqueous formaldehyde (1.8 mL, 23 mmol). The mixture was stirred at room temperature for 1 h before adding $NaBH(OAc)_3$. The mixture was stirred at room temperature for 18 h and quenched with saturated aqueous $NaHCO_3$. The organic phase was washed with water, brine and dried ($Na_2SO_4$). Concentration and purification by flash chromatography (1 % MeOH/EtOAc) gave the title compound as yellow oil (2.69 g, 37% yield). LCMS (M+H) calcd for $C_{12}H_{17}FN_5O_2S$: 314.10; found: 314.16.

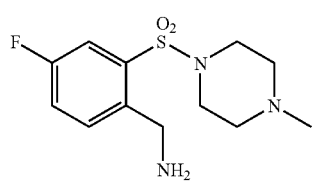

Intermediate 7

(4-Fluoro-2-(4-methylpiperazin-1-ylsulfonyl)phenyl) methanamine. A solution of Intermediate 6 (2.7 g, 8.6 mmol) in EtOAc (100 mL) and 1N HCl (10 mL) was shaken with catalytic Pd/C under $H_2$ at 45 psi for 18 h. The mixture was filtered over celite and concentrated. The resulting residue was dissolved in water and washed with EtOAc, diethyl ether and $CH_2Cl_2$. The aqueous layer was freeze dried to give the title compound as a yellow powder and bis-HCl salt (2.34 g, 76% yield).

¹H NMR (500 MHz, DMSO) δ: 7.93 (1H, dd, J=8.5, 5.2 Hz), 7.79-7.74 (2H, m), 4.33 (2H, d, J=4.0 Hz), 3.80 (2H, d, J=10.7 Hz), 3.46-3.44 (2H, m), 3.17 (4H, bs), 3.15 (2H, bs), 2.76 (3H, s). LCMS (M+H) calcd for $C_{12}H_{19}FN_3O_2S$: 288.11; found: 288.16.

(2H, m), 7.57 (1H, td, J=8.1,2.8 Hz), 4.43 (2H, s), 3.76-3.73 (4H, m), 3.19-3.15 (4H, m). LCMS (M+H) calcd for $C_{11}H_{16}FN_2O_3S$: 275.08; found: 275.15.

Intermediate 8

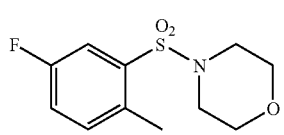

4-(5-Fluoro-2-methylphenylsulfonyl)morpholine. Following the procedure for Intermediate 1 using 5-fluoro-2-methylbenzenesulfonyl chloride (10.0 g, 48 mmol), triethylamine (13.9 mL, 100 mmol) and morpholine (8.37 g, 96 mmol) gave the title compound as white solid (10.07 g, 81% yield). ¹H NMR (300 MHz, CDCl₃) δ: 7.58 (1H, dd, J=8.6, 2.7 Hz), 7.27 (1H, dd, J=8.4, 5.1 Hz), 7.15 (1H, td, J=8.1, 2.8 Hz), 3.72-3.68 (4H, m), 3.16-3.13 (4H, m), 2.57 (3H, s). LCMS (M+H) calcd for $C_{11}H_{15}FNO_3S$: 260.07; found: 260.15.

Intermediate 9

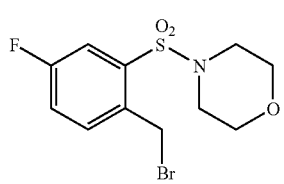

4-(2-(Bromomethyl)-5-flurorphenylsulfonyl)morpholine. Following the procedure for Intermediate 3 using Intermediate 8 (10.0 g, 38.6 mmol) gave the title compound as yellow oil that was carried on without purification.

Intermediate 10

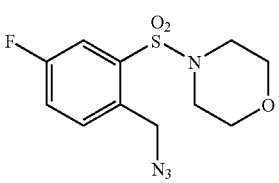

4-(2-(Azidomethyl)-5-fluorophenylsulfonyl)morpholine. Following the procedure for Intermediate 4 using Intermediate 9 (crude) gave the title compound as pale yellow oil (8.21 g, 71% yield over 2 steps).

Intermediate 11

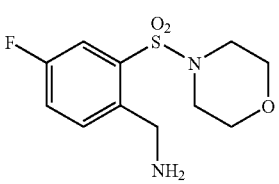

(4-Fluoro-2-(morpholinosulfonyl)phenyl)methanamine. Following the procedure for Intermediate 7 using Intermediate 10 gave the title compound as brown solid HCl salt (4.29 g, 51% yield). ¹HNMR (300 MHz, CD₃OD) δ: 7.80-7.73

Intermediate 12

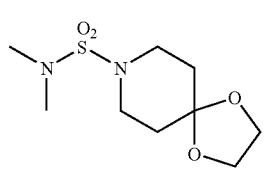

N,N-Dimethyl-1,4-dioxa-8-azaspiro[4.5]decane-8-sulfonamide. To a solution of 1,4-dioxa-8-azaspiro[4,5]decane (5.0 g, 35 mmol) in THF (25 mL) was added triethylamine (5 mL, 36 mmol) followed by N,N-dimethylsulfamoyl chloride (3.7 mL, 35 mmol). The resulting white mixture was stirred at room temperature for 1 h. The solids were removed by filtration and the solution was concentrated to give the title compound as a white solid (8.7 g, 100% yield). ¹H NMR (300 MHz, CDCl₃) δ: 3.93 (4H, s), 3.35 (4H, t, J=5.8 Hz), 2.78 (6H, s), 1.73 (4H, t, J=5.8 Hz). LCMS (M+H) calcd for $C_9H_{19}N_2O_4S$: 251.10; found: 251.24.

Intermediate 13

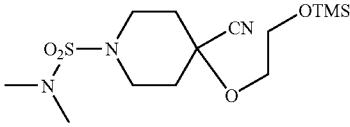

4-Cyano-N,N-dimethyl-4-(2-(trimethylsilyloxy)ethoxy)piperidine-1-sulfonamide. To a solution of Intermediate 12 (8.7 g, 35 mmol) in dichloromethane (4 mL) was added zinc iodide (2.2 g, 7 mmol). After stirring for 5 min, trimethylsilyl cyanide (4.75 mL, 35 mmol) was added and the mixture was stirred at room temperature for 2 h to give the title compound as yellow oil. ¹H NMR (300 MHz, CDCl₃) δ: 3.87-3.63 (4H, m), 3.54-3.42 (2H, m), 3.31-3.21 (2H, m), 2.78 (6H, d, J=2.9 Hz), 2.19-1.95 (4H, m), 0.095 (9H, s).

Intermediate 14

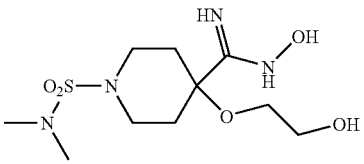

1-(N,N-Dimethylsulfamoyl)-N-hydroxy-4-(2-hydroxyethoxy)piperidine-4-carboximidamide. To a solution of crude Intermediate 13 (35 mmol) in ethanol (50 mL) was added 50 wt % aqueous hydroxylamine (2.5 mL, 35 mmol) and the resultant mixture was stirred at room temperature for 2 h to give the title compound which was carried on without purification. LCMS (M+H) calcd for $C_{10}H_{23}N_4O_5S$: 311.13; found: 311.26.

Intermediate 15

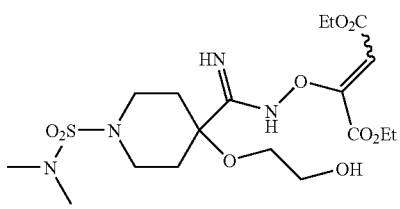

Diethyl 2-(1-(N,N-dimethylsulfamoyl)-4-(2-hydroxyethoxy)piperidine-4-carboximidamidooxy)but-2-enedioate. To a stirred solution of crude Intermediate 14 (35 mmol) in ethanol was added dietylacetylene dicarboxylate (5.7 mL, 36 mmol). The mixture was stirred at room temperature for 18 h, then concentrated and purified by flash chromatography (50% EtOAc/hexane to 100% EtOAC) to give the title compound as yellow foam (11.6 g, 69% yield). $^1$H NMR (300 MHz, CDCl$_3$) δ: 5.87 (1H, bs), 5.39 (1H, bs), 4.31 (2H, q, J=7.2 Hz), 4.18-4.11 (2H, m), 3.81 (2H, d, J=15.4 Hz), 3.48-3.39 (4H, m), 3.16-3.09 (2H, m), 2.78 (6H, d, J=5.5 Hz), 1.98 (5H, bs), 1.35-1.22 (6H, m). LCMS (M+H) calcd for $C_{18}H_{33}N_4O_9S$: 481.19; found: 481.29.

Intermediate 16

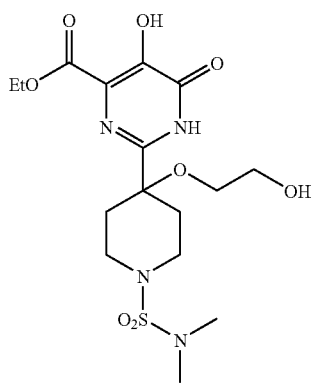

Ethyl 2-(1-(N,N-dimethylsulfamoyl)-4-(2-hydroxyethoxy)piperidin-4-yl)-5-hydroxy-6-oxo-1,6-dihydropyrimidine-4-carboxylate. A solution of Intermediate 15 (11.6 g, 24 mmol) in xylenes (250 mL) was stirred at 150° C. for 24 h. The mixture was concentrated and purified by chromatography (YMC Combiprep ODS-A, 30 mm×50 mm, MeOH/H2O/0.1% TFA) to yield the title compound as white solid (0.403 g, 8% yield). LCMS (M+H) calcd for $C_{16}H_{27}N_4O_8S$: 435.15; found: 435.14.

Intermediate 17

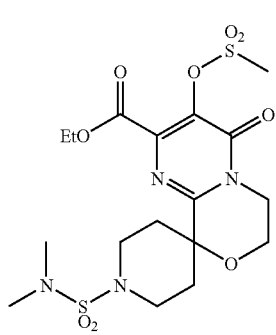

Ethyl 1-(N,N-dimethylsulfamoyl)-3'-(methylsulfonyloxy)-4'-oxo-6',7'-dihydro-4'H-spiro[piperidine-4,9'-pyrimido[2,1-c][1,4]oxazine]-2'-carboxylate. A solution of Intermediate 16 (0.40 g, 0.92 mmol) in THF (6 mL) was cooled to 0° C. and treated with methanesulfonyl chloride (0.210 mL, 2.8 mmol) followed by triethylamine (0.50 mL, 3.7 mmol). The mixture was stirred while gradually warming to room temperature for 18 h. Then, the mixture was diluted with ethyl acetate, washed with water, dried (Na$_2$SO$_4$) and concentrated. The resulting yellow foam was dissolved in THF/EtOH (10 mL, 1:1) and stirred with potassium carbonate (0.12 g, 0.9 mmol) at 75° C. for 3 h. The mixture was concentrated and partitioned between ethyl acetate and water. The organic phase was washed with water, brine, dried (Na$_2$SO$_4$) and concentrated to give the title compound as an amber glass (0.49 g, 98% yield). LCMS (M+H) calcd for $C_{17}H_{27}N_4O_9S_2$: 495.12; found: 495.20.

Intermediate 18

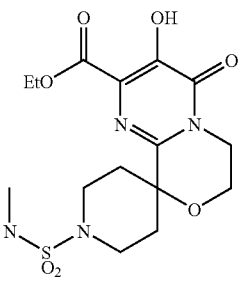

Ethyl 1-(N,N-dimethylsulfamoyl)-3'-hydroxy-4'-oxo-6',7'-dihydro-4'H-spiro[piperidine-4,9'-pyrimido[2,1-c][1,4]oxazine]-2'-carboxylate. To a solution of Intermediate 17 (0.49 g, 0.90 mmol) in EtOH (10 mL) was added sodium ethoxide (0.07 g, 1.2 mmol) and the mixture was stirred at 80° C. for 1 h. The mixture was cooled, concentrated and the residue was partitioned between ethyl acetate and water. The organic phase was concentrated and the resulting yellow oil was dissolved in methanol and let stand at room temp for 1 h. The solids that formed were collected by filtration to give the title compound as white solid (0.164 g, 44% yield). $^1$H NMR (300 MHz, CDCl$_3$) δ: 11.33 (1H, s), 4.30 (2H, q, J=7.1 Hz), 4.04-4.00 (2H, m), 3.89-3.85 (2H, m), 3.49 (2H, d, J=12.4 Hz), 3.04 (2H, td, J=12.0, 3.2 Hz), 2.77 (6H, s), 2.12-1.97 (4H, m), 1.28 (3H, t, J=7.1 Hz). LCMS (M+H) calcd for $C_{16}H_{25}N_4O_7S$: 417.14; found: 417.25.

Intermediate 19

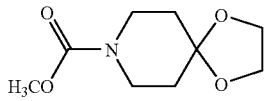

Methyl 1,4-dioxa-8-azaspiro[4.5]decane-8-carboxylate. Following the procedure for Intermediate 12 using methyl chloroformate gave the title compound as colorless oil (5.79 g, 82% yield). $^1$H NMR (300 MHz, CDCl$_3$) δ: 3.93 (4H, s), 3.65 (3H, s), 3.53-3.50 (4H, m), 1.65-1.61 (4H, m). LCMS (M+H) calcd for $C_9H_{16}NO_4$: 202.20; found: 202.23.

Intermediate 20

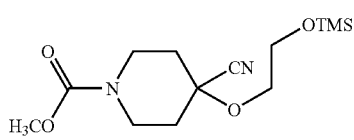

Methyl 4-cyano-4-(2-(trimethylsilyloxy)ethoxy)piperidine-1-carboxylate. Following the procedure for Intermediate 13 using Intermediate 19 gave the title compound as yellow oil. $^1$H NMR (300 MHz, CDCl$_3$) δ: 3.75-3.64 (6H, m), 3.71 (3H, s), 3.48-3.43 (2H, m), 2.07-2.01 (2H, m), 1.91-1.86 (2H, m), 0.085 (9H, s).

Intermediate 21

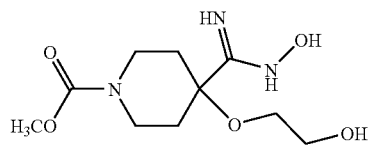

Methyl 4-(N-hydroxycarbamimidoyl)-4-(2-hydroxyethoxy)piperidine-1-carboxylate. Following the procedure for Intermediate 14 using Intermediate 20 gave the title compound that was carried on without purification. LCMS (M+H) calcd for C$_{10}$H$_{20}$N$_3$O$_5$: 262.14; found: 262.26.

Intermediate 22

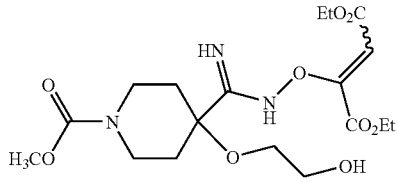

Diethyl 2-(4-(2-hydroxyethoxy)-1-(methoxycarbonyl)piperidine-4-carboximidamidooxy)but-2-enedioate. Following the procedure for Intermediate 15 using Intermediate 21 gave the title compound as yellow foam (5.6 g, 45% yield over 3 steps). $^1$H NMR (300 MHz, CDCl$_3$) δ: 5.80 (1H, bs), 5.34 (1H, bs), 4.35-4.25 (2H, m), 4.19-4.09 (2H, m), 3.93 (1H, bs), 3.82-3.76 (4H, m), 3.67 (3H, d, J=3.3 Hz), 3.48 (1H, bs), 3.43-3.41 (1H, m), 3.21-3.12 (2H, m), 1.89 (5H, bs), 1.35-1.20 (6H, m). LCMS (M+H) calcd for C$_{18}$H$_{30}$N$_3$O$_9$: 432.19; found: 432.27.

Intermediate 23

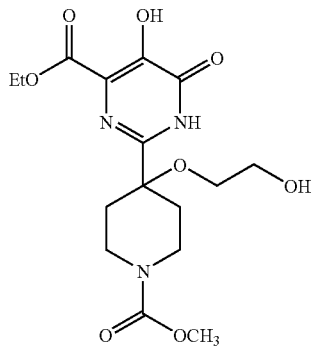

Ethyl 5-hydroxy-2-(4-(2-hydroxyethoxy)-1-(methoxycarbonyl)piperidin-4-yl)-6-oxo-1,6-dihydropyrimidine-4-carboxylate. Following the procedure for Intermediate 16 using Intermediate 22 gave the title compound as brown oil (1.71 g, 30% yield). LCMS (M+H) calcd for C$_{16}$H$_{24}$N$_3$O$_8$: 386.15; found: 386.27.

Intermediate 24

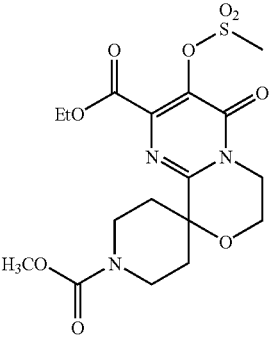

2'-Ethyl 1-methyl 3'-(methylsulfonyloxy)-4'-oxo-6',7'-dihydro-4'H-spiro[piperidine-4,9'-pyrimido[2,1-c][1,4]oxazine]-1,2'-dicarboxylate. Following the procedure for Intermediate 17 using Intermediate 23 gave the title compound as an amber glass (0.23 g, 12% yield over 2 steps). LCMS (M+H) calcd for C$_{17}$H$_{24}$N$_3$O$_9$S: 446.12; found: 446.21.

Intermediate 25

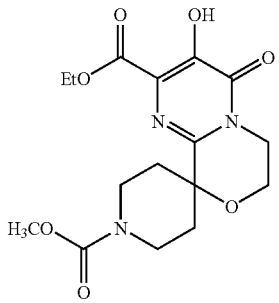

2'-Ethyl 1-methyl 3'-hydroxy-4'-oxo-6',7'-dihydro-4'H-spiro[piperidine-4,9'-pyrimido[2,1-c][1,4]oxazine]-1,2'-dicarboxylate. Following the procedure for Intermediate 18 using Intermediate 24 gave the title compound as a white solid (0.07 g, 36% yield). $^1$H NMR (300 MHz, DMSO-d$_6$) δ: 10.32 (1H, s), 4.29 (2H, q, J=7.1 Hz), 4.04-4.01 (2H, m), 3.93-3.86 (4H, m), 3.61 (3H, s), 3.06-2.99 (2H, m), 1.95-1.91 (4H, m), 1.27 (3H, t, J=7.10 Hz). LCMS (M+H) calcd for C$_{16}$H$_{22}$N$_3$O$_7$: 368.14; found: 368.28.

Intermediate 26

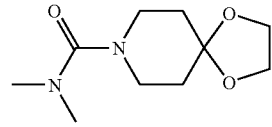

N,N-Dimethyl-1,4-dioxa-8-azaspiro[4.5]decane-8-carboxamide. Following the procedure for Intermediate 12 using dimethylcarbamyl chloride gave the title compound as a white solid (1.80 g, 60% yield). $^1$H NMR (300 MHz, CDCl$_3$)

δ: 3.92 (4H, s), 3.29-3.25 (4H, m), 2.77 (6H, s), 1.68-1.64 (4H, m). LCMS (M+H) calcd for $C_{10}H_{19}N_2O_3$: 215.14; found: 215.25.

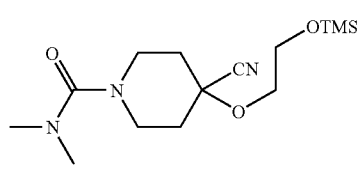

Intermediate 27

4-Cyano-N,N-dimethyl-4-(2-(trimethylsilyloxy)ethoxy)piperidine-1-carboxamide. Following the procedure for Intermediate 13 using Intermediate 26 gave the title compound that was carried on without purification.

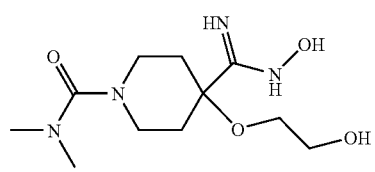

Intermediate 28

4-(N-Hydroxycarbamimidoyl)-4-(2-hydroxyethoxy)-N,N-dimethylpiperidine-1-carboxamide. Following the procedure for Intermediate 14 using Intermediate 27 gave the title compound that was carried on without purification. LCMS (M+H) calcd for $C_{11}H_{23}N_4O_4$: 275.17; found: 275.27.

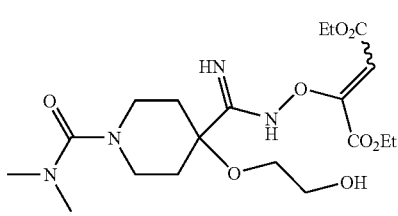

Intermediate 29

Diethyl 2-(1-(dimethylcarbamoyl)-4-(2-hydroxyethoxy)piperidine-4-carboximidamidooxy)but-2-enedioate. Following the procedure for Intermediate 15 using Intermediate 28 gave the title compound as yellow foam (0.85 g, 23% yield over 3 steps). $^1$H NMR (300 MHz, CDCl$_3$) δ: 5.74 (1H, d, J=16.5 Hz), 5.47 (1H, bs), 5.28 (1H, bs), 4.35-4.23 (2H, m), 4.18-4.09 (2H, m), 3.77-3.74 (2H, m), 3.46-3.36 (4H, m), 3.13-3.05 (2H, m), 2.81 (3H, s), 2.78 (3H, s), 1.98-1.86 (5H, m), 1.36-1.21 (6H, m). LCMS (M+H) calcd for $C_{19}H_{33}N_4O_8$: 445.23; found: 445.25.

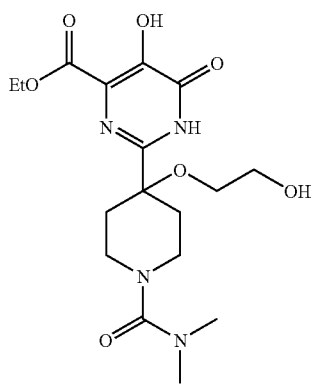

Intermediate 30

Ethyl 2-(1-(dimethylcarbamoyl)-4-(2-hydroxyethoxy)piperidin-4-yl)-5-hydroxy-6-oxo-1,6-dihydropyrimidine-4-carboxylate. Following the procedure for Intermediate 16 using Intermediate 29 gave the title compound as brown oil that was carried on without purification. LCMS (M+H) calcd for $C_{17}H_{27}N_4O_7$: 399.18; found: 399.27.

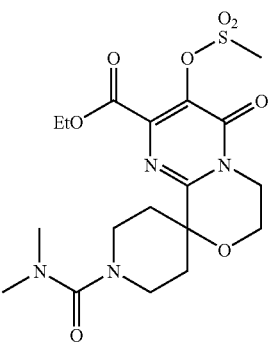

Intermediate 31

Ethyl 1-(dimethylcarbamoyl)-3'-(methylsulfonyloxy)-4'-oxo-6',7'-dihydro-4'H-spiro[piperidine-4,9'-pyrimido[2,1-c][1,4]oxazine]-2'-carboxylate. Following the procedure for Intermediate 17 using Intermediate 30 gave the title compound as white solid (0.1588 g, 22% yield over 2 steps). $^1$H NMR (300 MHz, CDCl$_3$) δ: 4.43 (2H, q, J=7.10 Hz), 4.07-4.00 (4H, m), 3.60 (2H, d, J=12.8 Hz), 3.53 (3H, s), 3.12 (2H, td, J=13.0, 1.5 Hz), 2.85 (6H, s), 2.33 (2H, td, J=1.89 (2H, d, J=12.8 Hz), 1.41 (3H, t, J=7.2 Hz). LCMS (M+H) calcd for $C_{18}H_{27}N_4O_8S$: 459.15; found: 459.23.

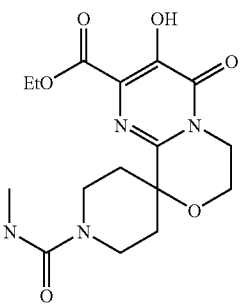

Intermediate 32

Ethyl 1-(dimethylcarbamoyl)-3'-hydroxy-4'-oxo-6',7'-dihydro-4'H-spiro[piperidine-4,9'-pyrimido[2,1-c][1,4]oxazine]-2'-carboxylate. Following the procedure for Intermediate 18 using Intermediate 31 gave the title compound as yellow solid (0.0758 g, 57% yield). $^1$H NMR (300 MHz, CDCl$_3$) δ: 10.59 (1H, s), 4.45 (2H, q, J=7.1 Hz), 4.03 (4H, s), 3.63 (2H, d, J=13.1 Hz), 3.16 (2H, t, J=12.5 Hz), 2.85 (6H, s), 2.29 (2H, td, J=13.3, 4.5 Hz), 1.86 (2H, d, J=13.4 Hz), 1.42 (3H, t, J=7.0 Hz). LCMS (M+H) calcd for $C_{17}H_{25}N_4O_6$: 381.17; found: 381.28.

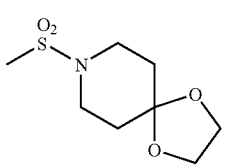

Intermediate 33

8-(Methylsulfonyl)-1,4-dioxa-8-azaspiro[4.5]decane. Following the procedure for Intermediate 12 using methanesulfonyl chloride gave the title compound as white solid (1.77 g, 80% yield). $^1$H NMR (300 MHz, CDCl$_3$) δ: 3.94 (4H, s), 3.31 (4H, t, J=5.8 Hz), 2.76 (2H, s), 1.79 (4H, t, J=5.7 Hz). LCMS (M+H) calcd for C$_8$H$_{16}$NO$_4$S: 222.08; found: 222.17.

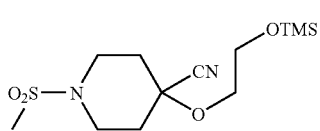

Intermediate 34

1-(Methylsulfonyl)-4-(2-(trimethylsilyloxy)ethoxy)piperidine-4-carbonitrile. Following the procedure for Intermediate 13 using Intermediate 33 gave the title compound as yellow oil that was carried on without purification. $^1$H NMR (300 MHz, CDCl$_3$) δ: 3.80-3.72 (4H, m), 3.56-3.48 (2H, m), 3.26-3.18 (2H, m), 2.80 (3H, s), 2.25-2.17 (2H, m), 2.08-1.99 (2H, m), 0.03 (9H, s).

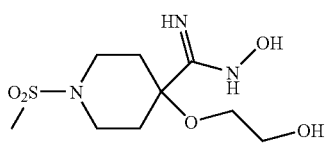

Intermediate 35

N-Hydroxy-4-(2-hydroxyethoxy)-1-(methylsulfonyl)piperidine-4-carboximidamide. Following the procedure for Intermediate 14 using Intermediate 34 gave the title compound that was used without purification.

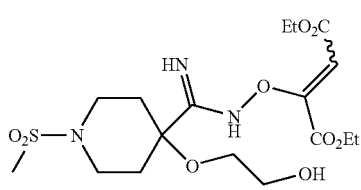

Intermediate 36

Diethyl 2-(4-(2-hydroxyethoxy)-1-(methylsulfonyl)piperidine-4-carboximidamidooxy)but-2-enedioate. Following the procedure for Intermediate 15 using Intermediate 35 gave the title compound as colorless foam (1.627 g, 45% yield over 3 steps). $^1$H NMR (300 MHz, CDCl$_3$) δ: 5.72 (1H, d, J=6.9 Hz), 5.52 (1H, bs), 5.33 (1H, bs), 4.44-4.23 (2H, m), 4.19-4.05 (2H, m), 3.81-3.71 (3H, m), 3.58-3.47 (2H, m), 3.44-3.41 (2H, m), 3.26-3.18 (1H, m), 3.11-3.01 (1H, m), 2.78 (3H, d, J=3.3 Hz), 2.25-1.97 (4H, m), 1.37-1.30 (3H, m), 1.26-1.21 (3H, m). LCMS (M+H) calcd for C$_{17}$H$_{30}$N$_3$O$_9$S: 452.17; found: 452.20.

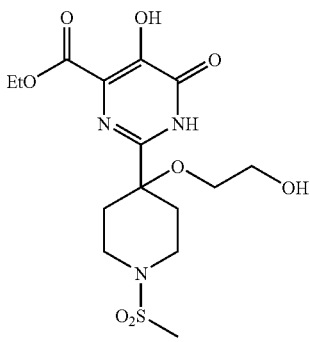

Intermediate 37

Ethyl 5-hydroxy-2-(4-(2-hydroxyethoxy)-1-(methylsulfonyl)piperidin-4-yl)-6-oxo-1,6-dihydropyrimidine-4-carboxylate. Following the procedure for Intermediate 16 using Intermediate 36 gave the title compound as brown oil (0.651 g, 45% yield). LCMS (M+H) calcd for C$_{15}$H$_{24}$N$_3$O$_8$S: 406.12; found: 406.19.

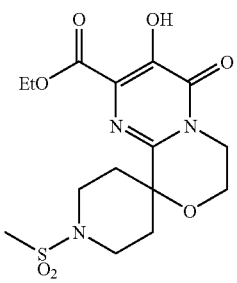

Intermediate 38

Ethyl 3'-hydroxy-1-(methylsulfonyl)-4'-oxo-6',7'-dihydro-4'H-spiro[piperidine-4,9'-pyrimido[2,1-c][1,4]oxazine]-2'-carboxylate. To a solution of Intermediate 37 (0.65 g, 1.6 mmol) in THF (5 mL) cooled to 0° C. was added methanesulfonyl chloride (0.37 mL, 4.8 mmol) and triethylamine (0.65 mL, 4.8 mmol). The mixture was gradually warmed to room temperature over 4 h, diluted with EtOAc and washed with water. The organic phase was dried (Na$_2$SO$_4$) and concentrated. The resulting brown oil was dissolved in EtOH/THF (20 mL, 1:1) and stirred with K$_2$CO$_3$ (0.15 g, 1.10 mmol) at 65° C. for 4 h. The mixture was concentrated and the residue was partitioned between EtOAc and water. The aqueous phase was made acidic with 6 N HCl and extracted with EtOAc. The organic phases were combined and washed with water and brine, dried (Na$_2$SO$_4$) and concentrated to give the title compound as pale brown solid (0.123 g, 29% yield). $^1$H NMR (300 MHz, CDCl$_3$) δ: 10.70 (1H, s), 4.43 (2H, q, J=8.1 Hz), 4.00 (4H, s), 3.71 (2H, d, J=11.3 Hz), 3.00 (2H, td, J=12.2, 2.3 Hz), 2.80 (3H, s), 2.43 (2H, td, J=13.2, 4.6 Hz), 1.95 (2H, dd, J=14.1, 2.0 Hz), 1.42 (3H, t, J=7.1 Hz). LCMS (M+H) calcd for C$_{15}$H$_{22}$N$_3$O$_7$S: 388.11; found: 388.19.

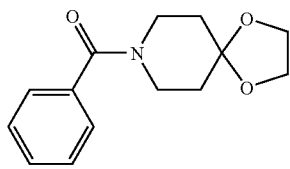

Intermediate 39

Phenyl(1,4-dioxa-8-azaspiro[4.5]decan-8-yl)methanone. Following the procedure for Intermediate 12 using benzoyl chloride gave the title compound as pale yellow oil (12.73 g, 51% yield). $^1$H NMR (300 MHz, CDCl$_3$) δ: 7.37 (5H, s), 3.95 (4H, s), 3.82 (2H, bs), 3.45 (2H, bs), 1.77 (2H, bs), 1.62 (2H, bs). LCMS (M+H) calcd for C$_{14}$H$_{18}$NO$_3$: 248.12; found: 248.20.

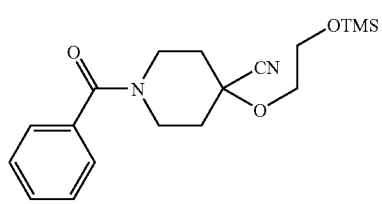

Intermediate 40

1-Benzoyl-4-(2-(trimethylsilyloxy)ethoxy)piperidine-4-carbonitrile. Following the procedure for Intermediate 13 using Intermediate 39 gave the title compound that was carried on without purification.

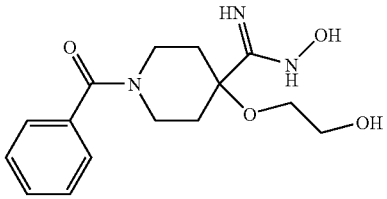

Intermediate 41

1-Benzoyl-N-hydroxy-4-(2-hydroxyethoxy)piperidine-4-carboximidamide. Following the procedure for Intermediate 14 using Intermediate 40 gave the title compound that was carried on without purification. LCMS (M+H) calcd for C$_{15}$H$_{22}$N$_3$O$_4$: 308.16; found: 308.16.

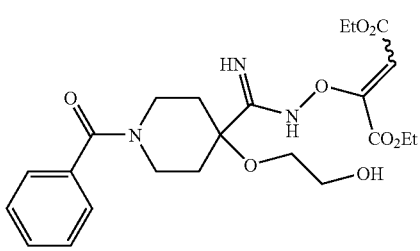

Intermediate 42

Diethyl 2-(1-benzoyl-4-(2-hydroxyethoxy)piperidine-4-carboximidamidooxy)-but-2-enedioate. Following the procedure for Intermediate 15 using Intermediate 41 gave the title compound as yellow foam (4.71 g, 19% yield over 3 steps). LCMS (M+H) calcd for C$_{23}$H$_{32}$N$_3$O$_8$: 478.21; found: 478.28.

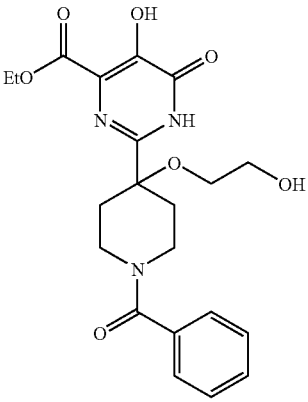

Intermediate 43

Ethyl 2-(1-benzoyl-4-(2-hydroxyethoxy)piperidin-4-yl)-5-hydroxy-6-oxo-1,6-dihydropyrimidine-4-carboxylate. Following the procedure for Intermediate 16 using Intermediate 42 gave the title compound as yellow foam (1.65 g, 39% yield). LCMS (M+H) calcd for C$_{21}$H$_{26}$N$_3$O$_7$: 432.17; found: 432.23.

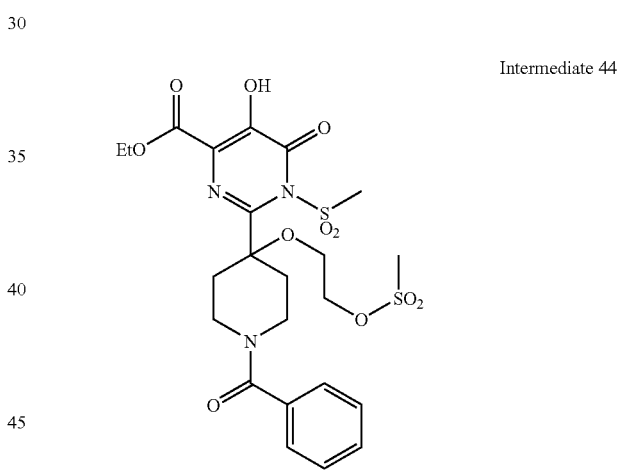

Intermediate 44

Ethyl 2-(1-benzoyl-4-(2-(methylsulfonyloxy)ethoxy)piperidin-4-yl)-5-hydroxy-1-(methylsulfonyl)-6-oxo-1,6-dihydropyrimidine-4-carboxylate. Intermediate 43 (1.65 g, 3.8 mmol) was dissolved in THF (15 mL) and cooled to 0° C. Methanesulfonyl chloride (0.90 mL, 11.610 mmol) was added followed by the dropwise addition of triethylamine (1.57 mL, 11.61 mmol). The resulting mixture was stirred for 4 h gradually warming to room temperature, diluted with EtOAc and washed with water and brine. The organic phase was dried (Na$_2$SO$_4$) and concentrated to give the title compound as an amber oil that was used without purification. LCMS (M+H) calcd for C$_{24}$H$_{32}$N$_3$O$_{13}$S$_3$: 666.11; found: 666.16.

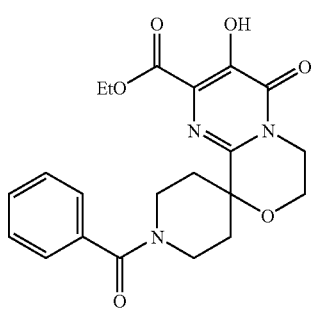

Intermediate 45

Ethyl 1-benzoyl-3'-hydroxy-4'-oxo-6',7'-dihydro-4'H-spiro[piperidine-4,9'-pyrimido[2,1-c][1,4]oxazine]-2'-carboxylate. To a stirred solution of Intermediate 44 (3.8 mmol) was dissolved in EtOH (30 mL) and THF (25 mL) was added potassium carbonate (0.535 g, 3.8 mmol) and the mixture was stirred at 65° C. for 18 h and concentrated. The residue was partitioned between EtOAc and water. The aqueous phase was made acidic with conc. HCl and extracted with EtOAc. The organic phases were combined, dried ($Na_2SO_4$) and concentrated to give the title compound as a pale brown solid (0.57 g, 36% yield over 2 steps). $^1$H NMR (300 MHz, $CDCl_3$) δ: 10.63 (1H, s), 7.443-7.38 (5H, m), 4.68-4.62 (1H, m), 4.49-4.41 (2H, m), 4.02 (4H, s), 3.70-3.64 (1H, m), 3.42-3.32 (1H, m), 3.20-3.11 (1H, m), 2.38-2.29 (1H, m), 2.26-2.17 (1H, m), 2.01-1.94 (1H, m), 1.80-1.74 (1H, m), 1.44 (3H, t, J=7.1 Hz). LCMS (M+H) calcd for $C_{21}H_{24}N_3O_6$: 414.16; found: 414.24.

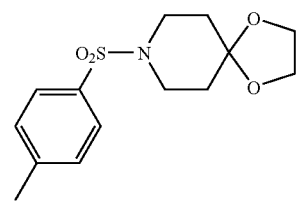

Intermediate 46

8-Tosyl-1,4-dioxa-8-azaspiro[4.5]decane. Following the procedure for Intermediate 12 using p-toluenesulfonyl chloride gave the title compound as white solid (10.3 g, 100% yield). $^1$H NMR (300 MHz, $CDCl_3$) δ: 7.61 (2H, d, J=8.4 Hz), 7.28 (2H, d, J=8.1 Hz), 3.86 (4H, s), 3.13-3.09 (4H, m), 2.40 (3H, s), 1.77-1.73 (4H, m). LCMS (M+H) calcd for $C_{14}H_{20}NO_4S$: 298.11; found: 289.20.

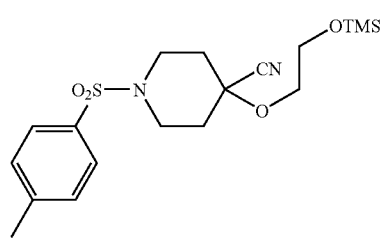

Intermediate 47

1-Tosyl-4-(2-(trimethylsilyloxy)ethoxy)piperidine-4-carbonitrile. Following the procedure for Intermediate 13 using Intermediate 46 gave the title compound that was used without purification. $^1$H NMR (300 MHz, $CD_3OD$) δ: 7.69 (2H, d, J=8.4 Hz), 7.45 (2H, d, J=8.0 Hz), 3.64 (4H, s), 3.30-3.22 (2H, m), 3.11-3.03 (2H, m), 2.47 (3H, s), 2.23-2.03 (4H, m), 0.14-0.12 (9H, m).

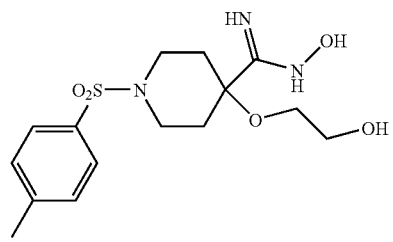

Intermediate 48

N-Hydroxy-4-(2-hydroxyethoxy)-1-tosylpiperidine-4-carboximidamide. Following the procedure for Intermediate 14 using Intermediate 47 gave the title compound that was carried on without purification.

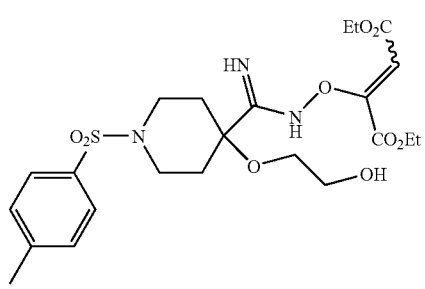

Intermediate 49

Diethyl 2-(4-(2-hydroxyethoxy)-1-tosylpiperidine-4-carboximidamidooxy)but-2-enedioate. Following the procedure for Intermediate 15 using Intermediate 48 gave the title compound as yellow foam (11.72 g, 71% yield). $^1$H NMR (300 MHz, $CDCl_3$) δ: 7.62 (2H, t, J=7.7 Hz), 7.30 (2H, t, J=8.2, 2.0 Hz), 5.27 (1H, s), 4.34-4.23 (2H, m), 4.19-4.05 (2H, m), 3.68-3.66 (2H, m), 3.54-3.49 (2H, m), 3.34-3.28 (2H, m), 2.72 (1H, td, J=11.4, 2.5 Hz), 2.66-2.57 (1H, m), 2.40 (3H, d, J=1.6 Hz), 2.05-1.89 (4H, m), 1.35-1.22 (6H, m). LCMS (M+H) calcd for $C_{23}H_{34}N_3O_9S$: 528.20; found: 528.12.

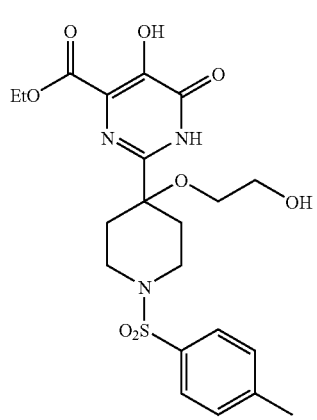

Intermediate 50

Ethyl 5-hydroxy-2-(4-(2-hydroxyethoxy)-1-tosylpiperidin-4-yl)-6-oxo-1,6-dihydropyrimidine-4-carboxylate. Following the procedure for Intermediate 16 using Intermediate 49 gave the title compound as brown solid (5.027 g, 47% yield). LCMS (M+H) calcd for $C_{21}H_{28}N_3O_8S$: 482.16; found: 482.11.

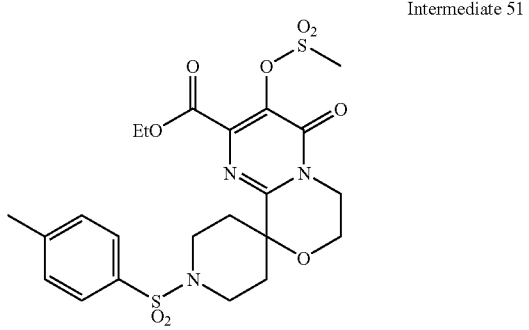

Intermediate 51

Ethyl 3'-(methylsulfonyloxy)-4'-oxo-1-tosyl-6',7'-dihydro-4'H-spiro-[piperidine-4,9'-pyrimido[2,1-c][1,4]oxazine]-2'-carboxylate. Following the procedure for Intermediate 17 using Intermediate 50 gave the title compound as brown foam (1.55 g, 46% yield). $^1$H NMR (300 MHz, CDCl$_3$) δ: 7.63 (2H, d, J=8.4 Hz), 7.31 (2H, d, J=8.0 Hz), 4.41 (2H, q, J=7.3 Hz), 3.92-3.89 (2H, m), 3.73-3.68 (1H, m), 3.49 (3H, s), 3.49-3.42 (1H, m), 2.63-2.48 (2H, m), 2.43-2.41 (4H, m), 1.92 (2H, d, J=13.5 Hz), 1.39 (3H, t, J=7.1 Hz). LCMS (M+H) calcd for $C_{22}H_{28}N_3O_9S_2$: 542.12; found: 542.03.

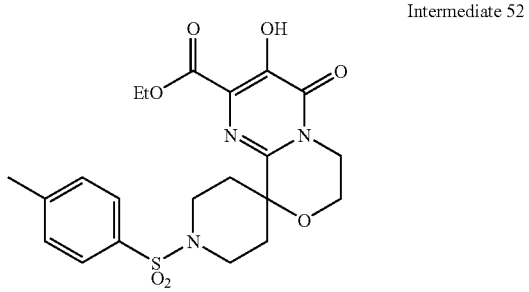

Intermediate 52

Ethyl 3'-hydroxy-4'-oxo-1-tosyl-6',7'-dihydro-4'H-spiro[piperidine-4,9'-pyrimido[2,1-c][1,4]oxazine]-2'-carboxylate. Following the procedure for Intermediate 18 using Intermediate 51 gave the title compound as pale yellow foam (0.3337 g, 91% yield). $^1$H NMR (300 MHz, CDCl$_3$) δ: 10.69 (1H, s), 7.63 (2H, d, J=8.4 Hz), 7.31 (2H, d, J=8.0 Hz), 4.41 (2H, q, J=7.1 Hz), 3.93-3.85 (4H, m), 3.73-3.69 (2H, m), 2.63-2.39 (4H, m), 2.42 (3H, s), 1.91 (2H, dd, J=13.2,1.1 Hz), 1.39 (3H, t, J=6.9 Hz). LCMS (M+H) calcd for $C_{21}H_{26}N_3O_7S$: 464.14; found: 464.12.

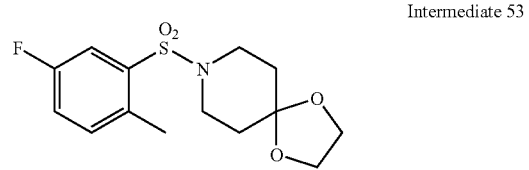

Intermediate 53

8-(5-Fluoro-2-methylphenylsulfonyl)-1,4-dioxa-8-azaspiro[4.5]decane. A stirred solution of 1,4-dioxa-8-azaspiro[4,5]decane (10.73 g, 75 mmol) and Et$_3$N (8 mL, 57 mmol) in THF (150 mL) was cooled in an ice-water bath. To this mixture was slowly added 5-fluoro-2-methylbenzenesulfonyl chloride (10.5 g, 50.33 mmol) and stirred for 1 h and then cold bath was removed. After 15 h at room temperature, the reaction mixture was diluted with ether (200 mL), washed with 1N aq. HCl (2×50 mL), brine (50 mL), dried (Na$_2$SO$_4$), filtered and concentrated to give product as an off-white solid 15.9 g, 100%). $^1$H NMR (500 MHz, CDCl$_3$) δ: 7.61 (1H, dd, J=8.6, 2.8 Hz), 7.28-7.26 (1H, m), 7.15 (1H, td, J=8.1, 2.8 Hz), 3.94 (4H, s), 3.35-3.32 (4H, m), 2.57 (3H, s), 1.78-1.76 (4H, m). HRMS (M+H) calcd for $C_{14}H_{19}FNO_4S$: 316.1019; found: 316.1013.

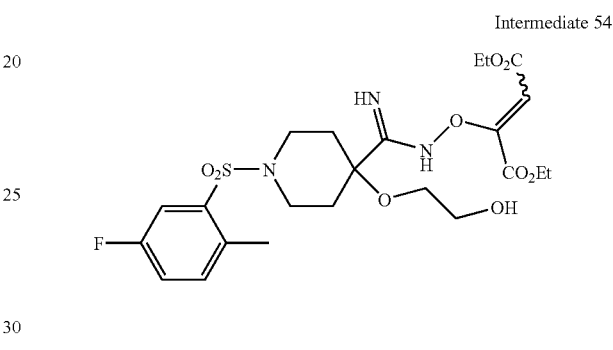

Intermediate 54

Diethyl 2-(1-(5-fluoro-2-methylphenylsulfonyl)-4-(2-hydroxyethoxy)-piperidine-4-carboximidamidooxy)but-2-enedioate. To stirred mixture of Intermediate 53 (7.884 g, 25 mmol) and ZnI$_2$ (0.96 g, 2 mmol) in CH$_2$Cl$_2$ (25 mL) was added trimethylsilyl cyanide (4 mL, 30 mmol) at room temperature. After 18 h, the reaction mixture was concentrated and the resulting residue was dissolved in EtOH/H$_2$O (4:1, 50 mL). To this was added 50% aq. NH$_2$OH (3.3 g, 50 mmol) and stirred for 2 h at 50° C. Then, the resulting white slurry was concentrated give viscous residue which was triturated with water (50 mL) and filtered to give white solid. This solid was suspended in DMF/H$_2$O (9:1, 200 mL) and treated with diethyl acetylenedicarboxylate (4 mL, 25 mmol). After 24 h at room temperature, the reaction mixture was concentrated and the resulting residue was taken up in ether (200 mL), washed with water (3×25 mL), brine (25 mL), dried (Na$_2$SO$_4$), filtered and concentrated to give paste. This paste was suspended in EtOAc/Hexanes/CH$_2$Cl$_2$, filtered and filtrate was concentrated and purified to afford product as white foam (9.28 g, 68%). $^1$H NMR (500 MHz, CDCl$_3$) δ: 7.65-7.61 (1H, m), 7.31-7.27 (1H, m), 7.19-7.13 (1H, m), 5.74 (0.5H, s), 5.73 (0.5H, s), 5.54 (1H, br s), 5.34 (1H, br s), 4.35-4.25 (2H, m), 4.18-4.13 (2H, m), 3.79-3.75 (2H, m), 3.56-3.48 (2H, m), 3.42-3.39 (2H, m), 3.13-3.05 (2H, m), 2.57 (1.5 H, s), 2.55 (1.5H, s), 2.05-1.95 (5H, m), 1.69 (1H, br s), 1.36-1.25 (6H, m). HRMS (M+H) calcd for $C_{23}H_{33}FN_3O_9S$: 546.1922; found: 546.1901.

Intermediate 55

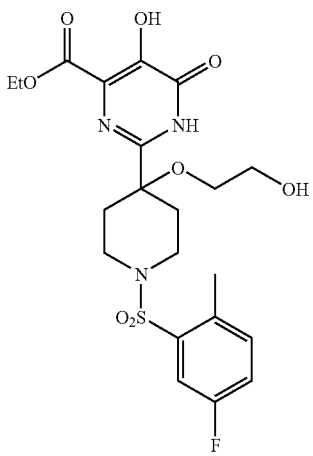

Ethyl 2-(1-(5-fluoro-2-methylphenylsulfonyl)-4-(2-hydroxyethoxy)piperidin-4-yl)-5-hydroxy-6-oxo-1,6-dihydropyrimidine-4-carboxylate. A solution of Intermediate 54 (9.26 g, 16.97 mmol) in xylenes (170 mL) was heated at reflux for 4 h and cooled. Then, the reaction mixture was diluted with ether (200 mL) and extracted with 0.2 M $Na_2CO_3$ (3×50 mL). The combined aq. Extracts acidified with conc. HCl and extracted with $CH_2Cl_2$ (3×100 mL). The combined $CH_2Cl_2$ extracts dried ($Na_2SO_4$), filtered and concentrated to give light brown foam (4.1 g, 48%) which was used in subsequent step without purification. $^1$H NMR (500 MHz, $CDCl_3$) δ: 10.81 (1H, s), 7.63 (1H, dd, J=8.7, 2.6 Hz), 7.31-7.28 (1H, m), 7.17 (1H, td, J=8.1, 2.8 Hz), 4.45 (2H, q, J=7.0 Hz), 3.86-3.82 (2H, br s), 3.74-3.67 (2H, m), 3.43-3.39 (2H, br s), 3.07 (2H, t, J=11.3 Hz), 2.60 (3H, s), 2.31-2.25 (4H, m), 2.01-1.98 (2H, m), 1.44 (3H, t, 7.0 Hz). HRMS (M+H) calcd for $C_{21}H_{27}FN_3O_8S$: 500.1503; found: 500.1509.

Intermediate 56

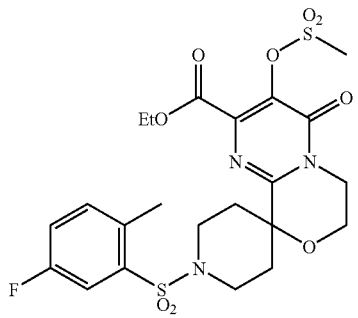

Ethyl 1-(5-fluoro-2-methylphenylsulfonyl)-3'-(methylsulfonyloxy)-4'-oxo-6',7'-dihydro-4'H-spiro[piperidine-4,9'-pyrimido[2,1-c][1,4]oxazine]-2'-carboxylate. To a stirred solution of Intermediate 55 (2.9 g, 5.8057 mmol) and $Et_3N$ (4.22 mL, 30 mmol) in THF (50 mL) at room temperature was added methanesulfonyl chloride (1.55 mL, 20 mmol) over 5 min. After 3 h, the resulting slurry was concentrated and suspended in EtOAc (150 mL), washed with water (2×20 mL), sat. $NaHCO_3$ (20 mL), brine (20 ml), dried ($Na_2SO_4$), filtered and concentrated to give viscous yellow oil. Flash column chromatography on silica gel using Hexanes/EtOAc mixtures afforded product as white solid (2.4922 g, 77%). $^1$H NMR (500 MHz, $CDCl_3$) δ: 7.63 (1H, dd, J=8.6, 2.8 Hz), 7.30 (1H, dd, J=8.4, 5.4 Hz), 7.17 (1H, td, J=8.1, 2.8 Hz), 4.44 (2H, q, J=7.0 Hz), 4.02-3.97 (4H, m), 3.72-3.67 (2H, m), 3.51 (3H, s), 3.02 (2H, td, J=12.5, 2.1 Hz), 2.61 (3H, s), 2.40 (2H, td, J=13.4, 4.6 Hz), 1.99-1.94 (2H, m), 1.41 (3H, t, J=7.0 Hz). HRMS (M+H) calcd for $C_{22}H_{27}FN_3O_9S_2$: 560.1173; found: 560.1187.

Intermediate 57

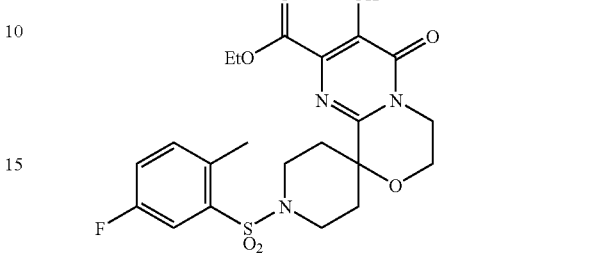

Ethyl 1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxylate. To a stirred solution Intermediate 56 (0.827 g, 1.4779 mmol) in THF (10 mL) was added 1N aq. NaOH (2 mL, 2 mmol). After 2 h at room temperature, the reaction mixture was taken up in EtOAc (50 mL), washed with 1N HCl (10 mL), water (10 mL), brine (10 mL), and dried ($Na_2SO_4$), filtered and concentrated to give orange solid (0.6615 g, 93%) which was used without purification. HRMS (M+H) calcd for $C_{21}H_{25}FN_3O_7S$: 482.1397; found: 482.1376.

Intermediate 58

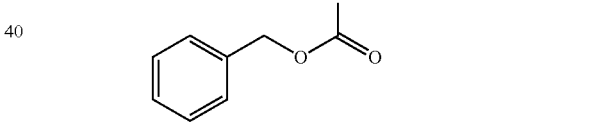

Benzyl 1,4-dioxa-8-azaspiro[4.5]decane-8-carboxylate. Following the procedure for Intermediate 12 using benzyl chloroformate gave the title compound as yellow oil (19.0 g, 98%). $^1$H NMR (300 MHz, $CDCl_3$) δ: 7.35-7.27 (5H, m), 5.10 (2H, s), 3.93 (4H, s), 3.58-3.54 (4H, m), 1.65-1.63 (4H, m). LCMS (M+H) calcd for $C_{15}H_{20}NO_4$: 278.13; found: 278.32.

Intermediate 59

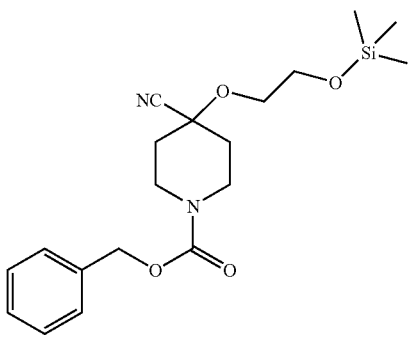

Benzyl 4-cyano-4-(2-(trimethylsilyloxy)ethoxy)piperidine-1-carboxylate. To Intermediate 58 (22.0 g, 70 mmol) was added zinc iodide (5.4 g, 16 mmol). After stirring for 5 min, trimethylsilyl cyanide (10.8 mL, 80 mmol) was added and the mixture was stirred at room temperature for 3 days to give the title compound that was carried on without purification.

Intermediate 60

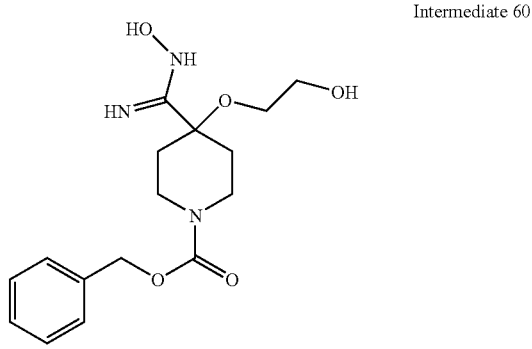

Benzyl 4-(N-hydroxycarbamimidoyl)-4-(2-hydroxyethoxy)piperidine-1-carboxylate. Following the procedure for Intermediate 14 using Intermediate 59 gave the title compound that was used without purification. LCMS (M+H) calcd for $C_{16}H_{24}N_3O_5$: 338.17; found: 338.33.

Intermediate 61

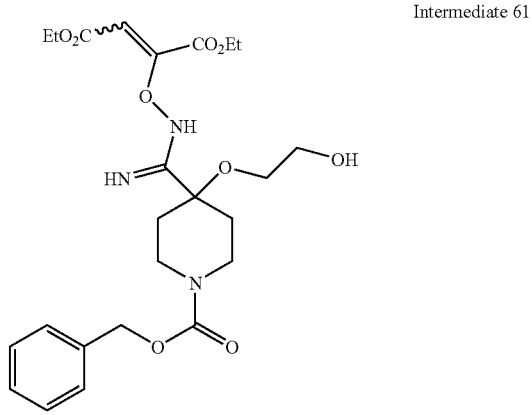

Diethyl 2-(1-(benzyloxycarbonyl)-4-(2-hydroxyethoxy)piperidine-4-carboximidamidooxy)but-2-enedioate. Following the procedure for Intermediate 15 using Intermediate 60 gave the title compound as pink oil (17.2 g, 48% yield over 3 steps). LCMS (M+H) calcd for $C_{24}H_{34}N_3O_9$: 508.23; found: 508.32.

Intermediate 62

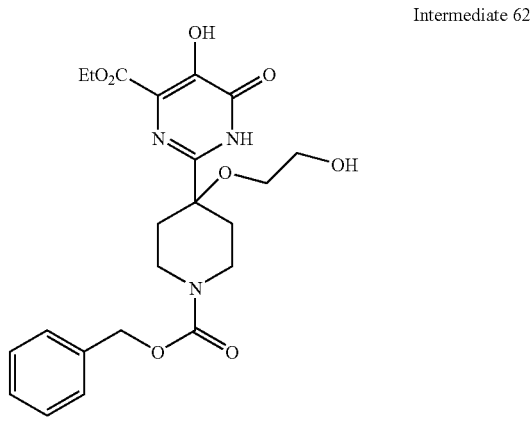

Ethyl 2-(1-(benzyloxycarbonyl)-4-(2-hydroxyethoxy)piperidin-4-yl)-5-hydroxy-6-oxo-1,6-dihydropyrimidine-4-carboxylate. Following the procedure for Intermediate 16 using Intermediate 61 gave the title compound as brown foam (12.3 g, 79%). LCMS (M+H) calcd for $C_{22}H_{28}N_3O_8$: 462.18; found: 462.32.

Intermediate 63

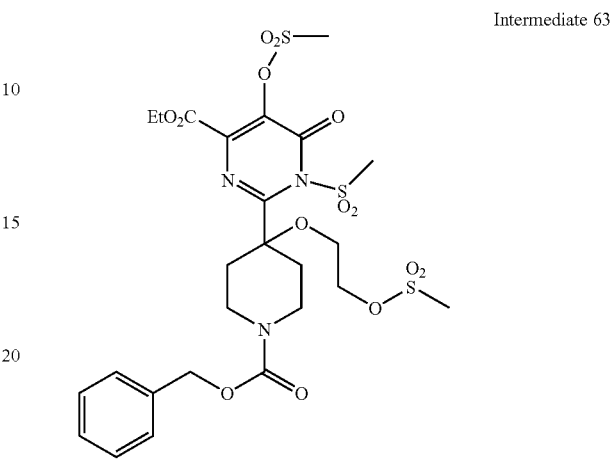

Ethyl 2-(1-(benzyloxycarbonyl)-4-(2-(methylsulfonyloxy)ethoxy)piperidin-4-yl)-1-(methylsulfonyl)-5-(methylsulfonyloxy)-6-oxo-1,6-dihydropyrimidine-4-carboxylate.

To a solution of Intermediate 62 (12.3 g, 27 mmol) in THF (50 mL) was added methane sulfonyl chloride (7.2 mL, 94.5 mmol) followed by dropwise addition of triethylamine (15 mL, 108 mmol). The mixture was stirred at 60° C. for 1 h and then at room temperature for 18 h. The mixture was diluted with EtOAc, washed with water, brine and was dried ($Na_2SO_4$). Concentration gave the title compound as brown foam that was carried on without purification. LCMS (M+H) calcd for $C_{25}H_{34}N_3O_{14}$: 696.12; found: 696.21.

Intermediate 64

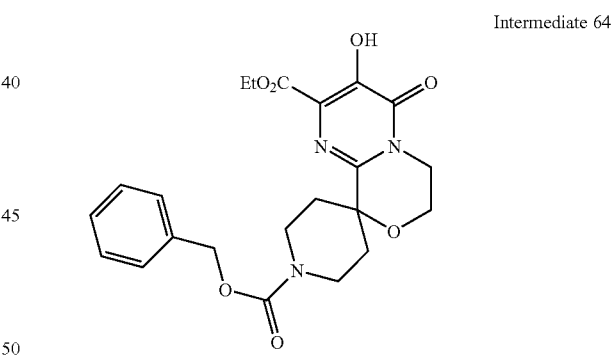

1-Benzyl 2'-ethyl 3'-hydroxy-4'-oxo-6',7'-dihydro-4'H-spiro[piperidine-4,9'-pyrimido[2,1-c][1,4]oxazine]-1,2'-dicarboxylate. To a solution of Intermediate 63 (27 mmol) in EtOH/THF (200 mL, 3:1) was added NaOEt (4.53 g, 54 mmol). The mixture was stirred at room temp for 2 h and concentrated. The residue was partitioned between EtOAc and H2O. The aqueous phase was extracted with EtOAc and the combined organic phases were washed with brine and dried ($Na_2SO_4$) and concentrated. The oil was purified by flash chromatography eluting with 0% to 5% MeOH in $CH_2Cl_2$ to give the title compound as brown foam (7.23 g, 60%). $^1$H NMR (300 MHz, $CDCl_3$) δ: 10.62 (1H, s), 7.335-7.29 (5H, m), 5.12 (2H, d, J=11.0 Hz), 4.43 (2H, q, J=14.3, 6.9 Hz), 4.37-4.30 (1H, m), 4.12-4.05 (1H, m), 4.00 (4H, s), 3.19-3.10 (2H, m), 2.28-2.18 (2H, m), 1.88-1.80 (2H, m), 1.40 (3H, t, J=7.1 Hz). LCMS (M+H) calcd for $C_{22}H_{26}N_3O_7$: 444.17; found: 444.31.

EXAMPLE 1

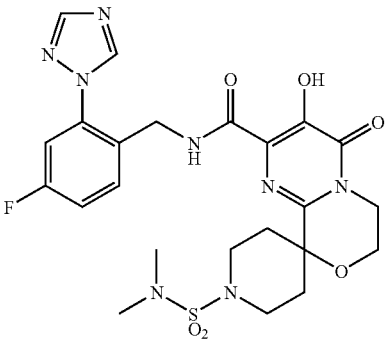

1-(N,N-Dimethylsulfamoyl)-N-(4-fluoro-2-(1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide. To a mixture of Intermediate 18 (0.042 g, 0.10 mmol) in DMF/EtOH (2 mL, 1:1) was added triethylamine (0.045 mL, 0.32 mmol) and (4-fluoro-2-(1H-1,2,4-triazol-1-yl)phenyl)methanamine HCl salt (prepared using procedure reported by Naidu, B. N. et al in U.S. Pat. No. 7,557,447, 0.04 g 0.20 mmol). The resulting mixture was stirred at 80° C. for 3 days and concentrated. The residue was triturated with hot MeOH and filtered to give the title compound as white solid (0.0238 g, 42% yield). $^1$H NMR (500 MHz, CDCl$_3$) δ: 12.05 (1H, s), 8.83 (1H, t, J=6.6 Hz), 8.43 (2H, s), 7.67 (1H, dd, J=8.4, 5.9 Hz), 7.17 (1H, td, J=8.2, 2.6 Hz), 7.07 (1H, dd, J=8.4, 2.6 Hz), 4.42 (2H, d, J=6.6 Hz), 3.98 (4H, s), 3.68 (2H, dd, J=12.6, 1.6 Hz), 3.18 (2H, td, J=12.8, 1.9 Hz), 2.81 (6H, s), 2.36 (2H, td, J=13.4, 4.8 Hz), 1.89 (2H, d, J=13.5 Hz). HRMS (M+H) calcd for C$_{23}$H$_{28}$N$_8$O$_6$SF: 563.1837; found: 563.1812.

The following examples in Table 5 were prepared according to the above procedure using appropriate intermediate and benzyl amine (some benzylamines used here were prepared using procedure reported by Naidu, B. N. et al in U.S. Pat. No. 7,557,447).

TABLE 5

| Example | Structure | Analytical Data |
|---|---|---|
| 2 | 1-(N,N-Dimethylsulfamoyl)-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide | Yield: 59%. $^1$H NMR(500 M Hz, CDCl$_3$) δ: 12.12(1H, bs), 7.87(1H, t, J=5.3 Hz), 7.31(2H, dd, J=8.6, 5.3 Hz), 7.01(2H, t, J=8.8 Hz), 4.56(2H, d, J=6.6 Hz), 3.99(4H, s), 3.64(2H, dd, J=11.7, 2.2 Hz), 3.15(2H, t, J=12.1 Hz), 2.79(6H, s), 2.25(2H, td, J=13.3, 4.3 Hz), 1.88(2H, d, J=13.5 Hz). HRMS(M + H) calcd for C$_{21}$H$_{27}$N$_5$O$_6$FS: 496.1666; found: 496.1644. |
| 3 | Methyl 2'-(4-fluoro-2-(1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate | Yield: 22%. $^1$H NMR(500 M Hz, CDCl$_3$) δ: 11.94(1H, s), 8.92(1H, t, J=6.8 Hz), 8.42(1H, s), 8.13(1H, s), 7.66(1H, dd, J=8.4, 5.9 Hz), 7.18(1H, td, J=8.2, 2.4 Hz), 7.09(1H, dd, J=8.6, 2.4 Hz), 4.40(2H, d, J=6.6 Hz), 4.13-4.06(2H, m), 3.09(4H, s), 3.74(3H, s), 3.17-3.08(2H, m), 2.23-2.13(2H, m), 1.86(2H, d, J=13.2 Hz). HRMS (M + H) calcd for C$_{23}$H$_{25}$N$_7$O$_6$F: 514.1850; found: 514.1857. |

TABLE 5-continued

| Example | Structure | Analytical Data |
|---|---|---|
| 4 | 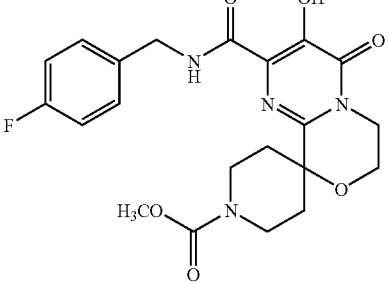<br>Methyl 2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-carboxylate | Yield: 49%. $^1$H NMR(500 MHz, CDCl$_3$) δ: 12.11(1H, s), 7.78-7.73(1H, m), 7.33-7.29(2H, m), 7.06-7.00(2H, m), 4.58(2H, d, J=6.2 Hz), 4.11-4.03(2H, m), 4.00(4H, s), 3.68(3H, s), 3.14-3.05(2H, m), 2.12-2.00(2H, m), 1.85(2H, d, J=12.4 Hz). HRMS(M + H) calcd for C$_{21}$H$_{24}$N$_4$O$_6$F: 447.1680; found: 447.1676. |
| 5 | 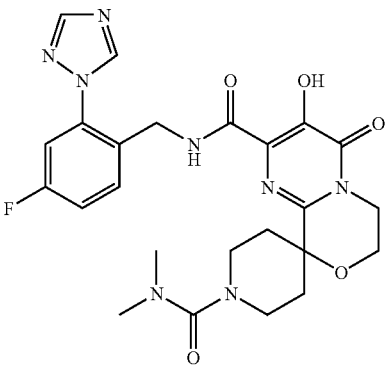<br>N$^{2'}$-(4-Fluoro-2-(1H-1,2,4-triazol-1-yl)benzyl)-3'-hydroxy-N$^1$,N$^1$-dimethyl-4'-oxo-6',7'-dihydro-4'H-spiro[piperidine-4,9'-pyrimido[2,1-c][1,4]oxazine]-1,2'-dicarboxamide | Yield: 13%. $^1$H NMR(500 MHz, CDCl$_3$) δ: 12.03(1H, bs), 8.81(1H, t, J=6.0 Hz), 8.41(1H, s), 8.36(1H, s), 7.67(1H, dd, J=8.8, 5.9 Hz), 7.18(1H, td, J=8.0, 2.6 Hz), 7.08(1H, td, J=8.4, 2.2 Hz), 4.42(2H, d, J=6.6 Hz), 3.99(4H, s), 3.65(2H, d, J=12.8 Hz), 3.20(2H, t, J=11.7 Hz), 2.84(6H, s), 2.31-2.21(2H, m), 1.84(2H, d, J=13.2 Hz). HRMS(M + H) calcd for C$_{24}$H$_{28}$N$_8$O$_5$F: 527.2167; found: 527.2153. |
| 6 | 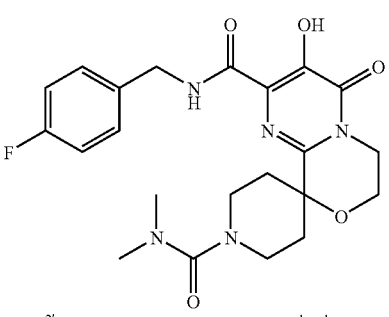<br>N$^{2'}$-(4-Fluorobenzyl)-3'-hydroxy-N$^1$,N$^1$-dimethyl-4'-oxo-6',7'-dihydro-4'H-spiro[piperidine-4,9'-pyrimido[2,1-c][1,4]oxazine]-1,2'-dicarboxamide | Yield: 12%. $^1$H NMR(500 MHz, CDCl$_3$) δ: 12.15(1H, bs), 7.92(1H, t, J=5.2 Hz), 7.33(2H, dd, J=8.4, 5.3 Hz), 7.04(2H, t, J=8.7 Hz), 4.59(2H, d, J=6.4 Hz), 4.03(4H, s), 3.64(2H, d, J=13.4 Hz), 3.18(2H, t, J=12.5 Hz), 2.82(6H, s), 2.18(2H, td, J=13.3, 4.0 Hz), 1.85(2H, d, J=13.1 Hz). HRMS (M + H) calcd for C$_{22}$H$_{27}$N$_5$O$_5$F: 460.1996; found: 460.1975. |

TABLE 5-continued

| Example | Structure | Analytical Data |
|---|---|---|
| 7 | 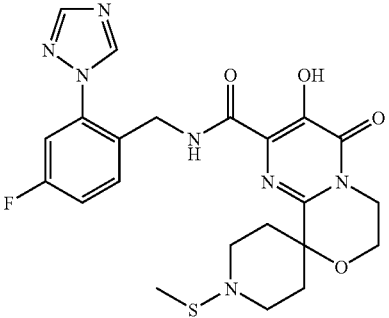<br>N-(4-Fluoro-2-(1H-1,2,4-triazol-1-yl)benzyl)-3'-hydroxy-1-(methylsulfonyl)-4'-oxo-6',7'-dihydro-4'H-spiro[piperidine-4,9'-pyrimido[2,1-c][1,4]oxazine]-2'-carboxamide | Yield: 33%. $^1$H NMR(500 M Hz, CDCl$_3$) δ: 11.97(1H, s), 8.91(1H, bs), 8.46-8.38(2H, m), 7.65(1H, dd, J=7.9, 6.0 Hz), 7.18(1H, t, J=8.6 Hz), 7.10-7.07(1H, m), 4.42(2H, s), 3.99(4H, s), 3.75(2H, d, J=11.0 Hz), 3.00(2H, t, J=11.3 Hz), 2.81(3H, s), 2.46-2.38(2H, m), 1.99(2H, d, J=12.8 Hz). HRMS(M + H) calcd for C$_{22}$H$_{25}$N$_7$O$_6$FS: 534.1571; found: 534.1570. |
| 8 | 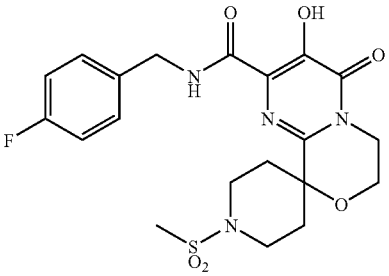<br>N-(4-Fluorobenzyl)-3'-hydroxy-1-(methylsulfonyl)-4'-oxo-6',7'-dihydro-4'H-spiro[piperidine-4,9'-pyrimido[2,1-c][1,4]oxazine]-2'-carboxamide | Yield: 53%. $^1$H NMR(500 M Hz, CDCl$_3$) δ: 12.16(1H, s), 7.81(1H, t, J=6.0 Hz), 7.35-7.30(2H, m), 7.05-6.99(2H, m), 4.57(2H, d, J=6.6 Hz), 4.00(4H, d, J=1.1 Hz), 3.72-3.67(2H, m), 3.00-2.91(2H, m), 2.78(3H, s), 2.30(2H, td, J=13.3, 4.6 Hz), 1.97(2H, d, J'213.17 Hz). HRMS(M + H) calcd for C$_{20}$H$_{24}$N$_4$O$_6$FS: 467.1401; found: 467.1423. |
| 9 | 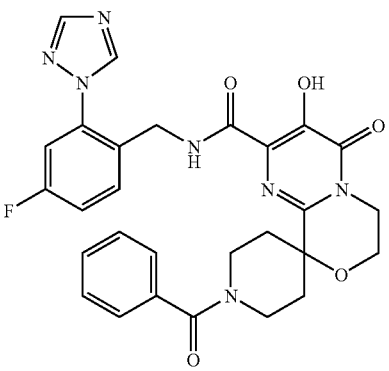<br>1-Benzoyl-N-(4-fluoro-2-(1H-1,2,4-triazol-1-yl)benzyl)-3'-hydroxy-4'-oxo-6',7'-dihydro-4'H-spiro[piperidine-4,9-pyrimido[2,1-c][1,4]oxazine]-2'-carboxamide | Yield: 33%. $^1$H NMR(500 M Hz, CDCl$_3$) δ: 12.03(1H, s), 8.74(1H, t, J=6.8 Hz), 8.42(1H, s), 8.22(1H, s), 7.66(1H, dd, J=8.6, 5.7 Hz), 7.42-7.31(5H, m), 7.20(1H, td, J=8.0, 2.6 Hz), 7.10(1H, dd, J=8.2, 2.4 Hz), 4.77-4.68(1H, m), 4.42(2H, d, J=6.2 Hz), 4.01(4H, s), 3.77-3.66(1H, m), 3.47-3.36(1H, m), 3.22-3.09(1H, m), 2.34-1.78(4H, m). HRMS (M + H) calcd for C$_{28}$H$_{27}$N$_7$O$_5$F: 560.2058; found: 560.2039. |

TABLE 5-continued

| Example | Structure | Analytical Data |
|---|---|---|
| 10 | 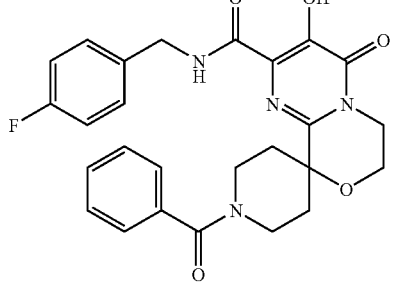<br>1-Benzoyl-N-(4-fluorobenzyl)-3′-hydroxy-4′-oxo-6′,7′-dihydro-4′H-spiro[piperidine-4,9′-pyrimido[2,1-c][1,4]oxazine]-2′-carboxamide | Yield: 63%. $^1$H NMR(500 M Hz, CDCl$_3$) δ: 12.13(1H, s), 7.75(1H, t, J=6.0 Hz), 7.39-7.31(7H, m), 7.04(2H, t, J=8.6 Hz), 4.71-4.57(3H, m), 4.02(4H, s), 3.70-3.67(1H, m), 3.46-3.35(1H, m), 3.16-3.08(1H, m), 2.29-2.18(1H, m), 2.02-1.94(2H, m), 1.85-1.78(1H, m). HRMS(M + H) calcd for C$_{26}$H$_{26}$N$_4$O$_5$F: 493.1887; found: 493.1884. |
| 11 | 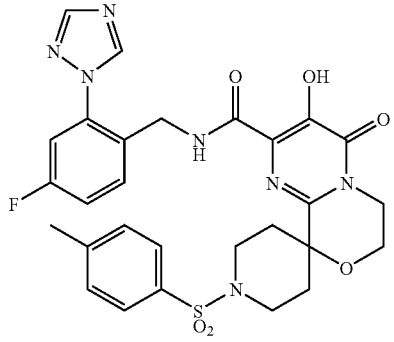<br>N-(4-Fluoro-2-(1H-1,2,4-triazol-1-yl)benzyl)-3′-hydroxy-4′-oxo-1-tosyl-6′,7′-dihydro-4′H-spiro[piperidine-4,9′-pyrimido[2,1-c][1,4]oxazine]-2′-carboxamide | Yield: 12%. $^1$H NMR(500 M Hz, CDCl$_3$) δ: 11.92(1H, s), 8.99-8.93(1H, m), 8.45(2H, d, J=4.4 Hz), 7.65(3H, d, J=8.0 Hz), 7.32(2H, d, J=8.0 Hz), 7.23-7.15(1H, m), 7.10(1H, dd, J=8.4, 2.2 Hz), 4.44(2H, d, J=6.2 Hz), 3.93(2H, t, J=4.4 Hz), 3.85(2H, t, J=9.9 Hz), 2.59-2.48(2H, m), 2.44-2.39(2H, m), 2.42(3H, s), 1.93(2H, d, J=12.4 Hz). HRMS(M + H) calcd for C$_{28}$H$_{29}$N$_7$O$_6$FS: 610.1884; found: 610.1876. |
| 12 | 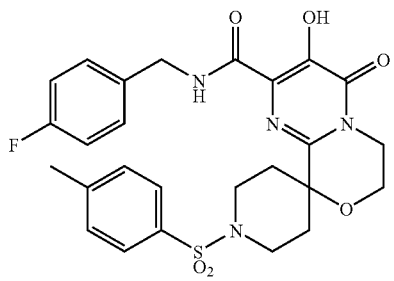<br>N-(4-Fluoro-2-(1H-1,2,4-triazol-1-yl)benzyl)-3′-hydroxy-4′-oxo-1-tosyl-6′,7′-dihydro-4′H-spiro[piperidine-4,9′-pyrimido[2,1-c][1,4]oxazine]-2′-carboxamide | Yield: 4%. $^1$H NMR(500 M Hz, CDCl$_3$) δ: 12.17(1H, bs), 7.84(1H, t, J=6.4 Hz), 7.64(2H, d, J=8.2 Hz), 7.38-7.24(4H, m), 7.09-7.04(2H, m), 4.61(2H, d, J=6.4 Hz), 3.97(2H, t, 4.9 Hz), 3.87(2H, t, J=4.9 Hz), 3.72(2H, d, J=12.5 Hz), 2.54(2H, t, J=1.11 Hz), 2.45(3H, s), 2.35(2H, dt, J=13.4, 4.6 Hz), 1.94(2H, d, J=13.4 Hz). HRMS(M + H) calcd for C$_{26}$H$_{28}$N$_4$O$_6$FS: 543.1714; found: 543.1722. |
| 13 | 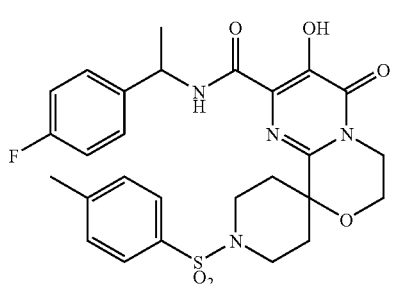<br>N-(1-(4-Fluorophenyl)ethyl)-3′-hydroxy-4′-oxo-1-tosyl-6′,7′-dihydro-4′H-spiro[piperidine-4,9′-pyrimido[2,1-c][1,4]oxazine]-2′-carboxamide | Yield: 5%. $^1$H NMR(500 M Hz, CDCl$_3$) δ: 12.21(1H, s), 7.65-7.57(3H, m), 7.37-7.31(4H, m), 7.08-7.02(2H, m), 5.29-5.19(1H, m), 3.95-3.92(2H, m), 3.86-3.82(2H, m), 3.73-3.68(2H, m), 2.57-2.48(2H, m), 2.43(3H, s), 2.39-2.25(2H, m), 1.96-1.89(2H, m), 1.65(3H, d, J=7.3 Hz). HRMS(M + H) calcd for C$_{27}$H$_{30}$N$_4$O$_6$S: 557.1870; found: 557.1878. |

TABLE 5-continued

| Example | Structure | Analytical Data |
|---|---|---|
| 14 | 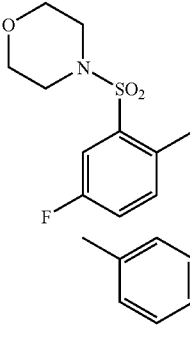<br>N-(4-Fluoro-2-(morpholinosulfonyl)benzyl)-3'-hydroxy-4'-oxo-1-tosyl-6',7'-dihydro-4'H-spiro[piperidine-4,9'-pyrimido[2,1-c][1,4]oxazine]-2'-carboxamide | Yield: 31%. $^1$H NMR(500 M Hz, CDCl$_3$) δ: 11.91(1H, s), 7.64-7.58(3H, m), 7.50(1H, dd, J=8.0, 1.8 Hz), 7.32(2H, d, J=8.0 Hz), 7.28-7.25(1H, m), 4.85(2H, d, J=5.9 Hz), 3.94-3.90(2H, m), 3.83-3.80(6H, m), 3.68(2H, d, J=10.6 Hz), 3.34-3.32(4H, m), 2.57-2.49(2H, m), 2.42(3H, s), 2.39-2.32(2H, m), 1.90(2H, d, J=13.5 Hz). HRMS (M + H) calcd for C$_{30}$H$_{35}$N$_5$O$_9$FS2: 692.1860; found: 692.1887. |
| 15 | 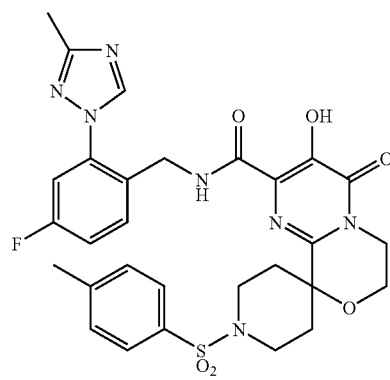<br>N-(4-Fluoro-2-(3-methyl-1H-1,2,4-triazol-1-yl)benzyl)-3'-hydroxy-4'-oxo-1-tosyl-6',7'-dihydro-4'H-spiro[piperidine-4,9'-pyrimido[2,1-c][1,4]oxazine]-2'-carboxamide | Yield: 44%. $^1$H NMR(500 M Hz, CDCl$_3$) δ: 12.27(1H, s), 8.68(1H, t, J=7.3 Hz), 8.37(1H, s), 7.67(1H, dd, J=8.4, 6.2 Hz), 7.61(2H, d, J=8.0 Hz), 7.31(2H, d, J=8.0 Hz), 7.20-7.07(2H, m), 4.46(2H, d, J=6.6 Hz), 3.94-3.91(2H, m), 3.85-3.81(2H, m), 3.69(2H, d, J=9.5 Hz), 2.68(3H, s), 2.42(3H, s), 2.53-2.33(4H, m), 1.93(2H, d, J 12.4 Hz). HRMS (M + H) calcd for C$_{29}$H$_{31}$N$_7$O$_6$FS: 624.2041; found: 624.2065. |
| 16 | 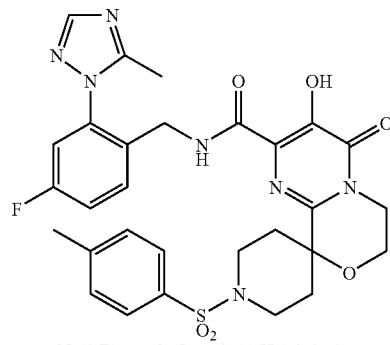<br>N-(4-Fluoro-2-(5-methyl-1H-1,2,4-triazol-1-yl)benzyl)-3'-hydroxy-4'-oxo-1-tosyl-6',7'-dihydro-4'H-spiro[piperidine-4,9'-pyrimido[2,1-c][1,4]oxazine]-2'-carboxamide | Yield: 34%. $^1$H NMR(500 M Hz, CDCl$_3$) δ: 11.92(1H, s), 8.78(1H, t, J=6.0 Hz), 8.29(1H, s), 7.69-7.59(1H, m), 7.62(2H, d, J=8.0 Hz), 7.31(2H, d, J=8.0 Hz), 7.25-7.18(1H, m), 7.03(1H, dd, J=8.4, 2.6 Hz), 4.32(2H, d, J=6.6 Hz), 3.94-3.91(2H, m), 3.86-3.83(2H, m), 3.73-3.71(2H, m), 2.53-2.48(4H, m), 2.52(3H, s), 2.42 (3H, s), 1.93(2H, d, J=11.3 Hz). HRMS(M + H) calcd for C$_{29}$H$_{31}$N$_7$O$_6$FS: 624.2041; found: 624.2022. |

TABLE 5-continued

| Example | Structure | Analytical Data |
|---|---|---|
| 17 | 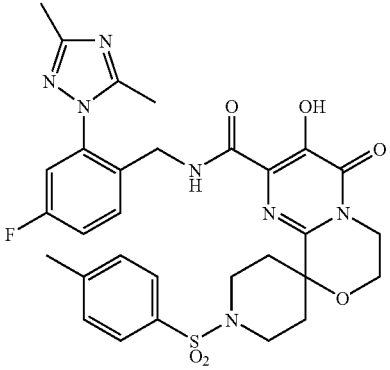<br>N-(2-(3,5-Dimethyl-1H-1,2,4-triazol-1-yl)-4-fluorobenzyl)-3'-hydroxy-4'-oxo-1-tosyl-6',7'-dihydro-4'H-spiro[piperidine-4,9'-pyrimido[2,1-c][1,4]oxazine]-2'-carboxamide | Yield: 59%. $^1$H NMR(500 M Hz, CDCl$_3$) δ: 12.18(1H, s), 8.44(1H, t, J=7.1 Hz), 7.67(1H, dd, J=7.9, 6.0 Hz), 7.60(2H, d, J=8.4 Hz), 7.31(2H, d, J=8.0 Hz), 7.20(1H, td, J=8.4, 2.9 Hz), 7.02(1H, dd, J=8.4, 2.6 Hz), 4.35(2H, d, J=6.6 Hz), 3.94-3.91(2H, m), 3.85-3.81(2H, m), 3.68(2H, d, J=9.5 Hz), 2.58(3H, s), 2.48-2.42(10H, m). HRMS(M + H) calcd for C$_{30}$H$_{33}$N$_7$O$_6$FS: 638.2197; found: 638.2184. |
| 18 | 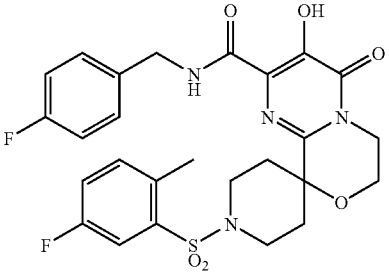<br>1-(5-Fluoro-2-methylphenylsulfonyl)-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide | Yield: 60%, white solid. $^1$H NMR(500 M Hz, CDCl$_3$) δ: 12.16(1H, s), 7.84(1H, s), 7.56(1H, dd, J=8.5, 2.4 Hz), 7.37-7.34(2H, m), 8.6, 5.5 Hz), 7.17(1H, td, J=7.9, 2.8 Hz), 7.06(2H, t, J=8.6 Hz), 4.62(2H, d, J=5.5 Hz), 4.01-3.94(4H, m), 3.77-3.71(2H, m), 2.94(2H, t, J=12.1 Hz), 2.57(3H, s), 2.36-2.28(2H, m), 1.97-1.92(2H, m). HRMS(M + H) calcd for C$_{26}$H$_{27}$F$_2$N$_4$O$_6$S: 561.1619; found: 561.1617. Anal. calcd for C$_{26}$H$_{26}$F$_2$N$_4$O$_6$S: C, 55.70; H, 4.67; N, 9.99; found: C, 55.63; H, 4.54; N, 9.88. |
| 19 | 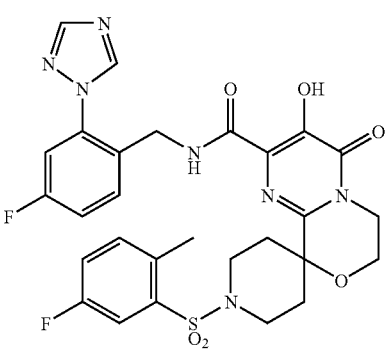<br>N-(4-Fluoro-2-(1H-1,2,4-triazol-1-yl)benzyl)-1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxamide | Yield: 52%, off-white solid. $^1$H NMR(500 M Hz, CDCl$_3$) δ: 12.08(1H, s), 8.85(1H, br s), 8.48(1H, s), 8.45(1H, s), 7.73-7.69(1H, m), 7.60(1H, dd, J=8.6, 2.8 Hz), 7.30(1H, dd, J=8.4, 5.3 Hz), 7.22-7.15(2H, m), 7.12(1H, dd, J=8.4, 2.3 Hz), 4.47(2H, d, J=6.7 Hz), 4.00-3.94(4H, m), 3.83-3.77(2H, m), 3.01(2H, t, J=11.9 Hz), 2.59(3H, s), 2.44(2H, td, J=13.1, 4.0 Hz), 1.99-1.93(2H, m). HRMS(M + H) calcd for C$_{28}$H$_{28}$F$_2$N$_7$O$_6$S: 628.1790; found: 628.1802. Anal. calcd for C$_{28}$H$_{27}$F$_2$N$_7$O$_6$S•0.5CH$_3$OH; C, 53.18; H, 4.54; N, 15.23; found: C 52.96; H, 4.20; N, 15.06. |

TABLE 5-continued

| Example | Structure | Analytical Data |
|---|---|---|
| 20 | N-(4-Fluoro-2-(3-methyl-1H-1,2,4-triazol-1-yl)benzyl)-1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxamide | Yield: 56%, purple solid. $^1$H NMR(500 M Hz, CDCl$_3$) δ: 12.29(1H, s), 8.61(1H, br s), 8.31(1H, s), 7.69-7.66(1H, m), 7.54(1H, dd, J=8.7, 2.6 Hz), 7.29-7.25(1H, m), 7.19-7.15(2H, m), 7.11(1H, dd, J=8.6, 2.5 Hz), 4.49(2H, d, J=6.1 Hz), 4.00-3.92(4H, m), 3.76-3.71(2H, m), 2.85(2H, t, J=11.9 Hz), 2.59(3H, s), 2.56(3H, s), 2.37(2H, td, J=12.8, 3.4 Hz), 2.00-1.94(2H, m). HRMS (M + H) calcd for C$_{29}$H$_{30}$F$_2$N$_7$O$_6$S: 642.1946; found: 642.1965. Anal. calcd for C$_{29}$H$_{29}$F$_2$N$_7$O$_6$S: C, 54.28; H, 4.55; N, 15.28; found: C, 54.10; H, 4.26; N, 15.27. |
| 21 | N-(4-Fluoro-2-(5-methyl-1H-1,2,4-triazol-1-yl)benzyl)-1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxamide | Yield: 70%, purple solid. $^1$H NMR(500 M Hz, CDCl$_3$) δ: 12.04(1H, s), 8.64(1H, t, J=6.1 Hz), 8.25(1H, s), 7.68(1H, dd, J=8.2, 6.1 Hz), 7.58(1H, dd, J=8.7, 2.6 Hz), 7.29(1H, dd, J=8.6, 5.5 Hz), 7.23(1H, td, J=8.2, 2.4 Hz), 7.17(1H, td, J=8.1, 2.8 Hz), 7.03(1H, dd, J=8.4, 2.6 Hz), 4.31(2H, d, J=6.4 Hz), 4.00-3.94(4H, m), 3.82-3.77(2H, m), 2.99(2H, t, J=11.9 Hz), 2.59(3H, s), 2.47(3H, s), 2.46(2H, td, J=13.6, 4.4 Hz), 1.99-1.94(2H, m). HRMS (M + H) calcd for C$_{29}$H$_{30}$F$_2$N$_7$O$_6$S: 642.1946; found: 642.1945. Anal. Calcd for C$_{29}$H$_{29}$F$_2$N$_7$O$_6$S•0.5 CH$_3$OH: C, 53.8; H, 4.75; N, 14.91; found: C, 53.58; H, 4.36; N, 14.77. |
| 22 | Benzyl 2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-carboxylate | Yield: 35%, brown solid. $^1$H NMR(300 M Hz, CDCl$_3$) δ: 12.11(1H, s), 7.76(1H, t, J=6.0 Hz), 7.34-7.27(7H, m), 7.05-6.99(2H, m), 5.10(2H, s), 4.56(2H, d, J=6.6 Hz), 4.12-4.05(2H, m), 4.00(4H, s), 3.16-3.07(2H, m), 2.12-2.01(2H, m), 1.87-1.83(2H, m). LCMS (M + H) calcd for C$_{27}$H$_{28}$FN$_4$O$_6$: 523.19; found: 523.24. |

TABLE 5-continued

| Example | Structure | Analytical Data |
|---|---|---|
| 23 | 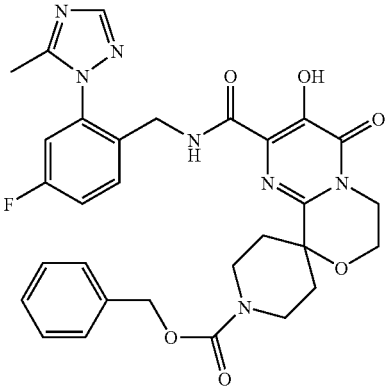 Benzyl 2'-(4-fluoro-2-(5-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate | Yield: 32%, white solid. $^1$H NMR(300 M Hz, CDCl$_3$) δ: 11.90(1H, s), 8.61(1H, t, J=6.6 Hz), 7.97(1H, s), 7.61(1H, dd, J=8.4, 5.9 Hz), 7.35-7.28(5H, m), 7.20(1H, td, J=8.4, 2.6 Hz), 6.95(1H, dd, J=8.2, 2.7 Hz), 5.19-5.11(2H, m), 4.25(2H, d, J=6.6 Hz), 4.16-4.12(2H, m), 3.99(4H, s), 3.19-3.10(2H, m), 2.44(3H, s), 2.21(2H, td, J=13.4, 4.9 Hz), 1.89-1.85(2H, m). HRMS(M + H) calcd for C$_{30}$H$_{31}$FN$_7$O$_6$: 604.2320; found: 604.2346. |
| 24 | 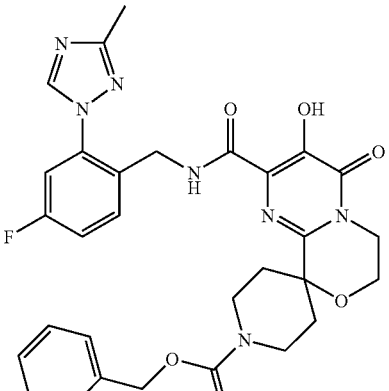 Benzyl 2'-(4-fluoro-2-(3-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate | Yield: 37%; White solid. $^1$H NMR(300 M Hz, CDCl$_3$) δ: 12.21(1H, s), 8.57(1H, s), 8.42(1H, t, J=6.6 Hz), 7.66(1H, dd, J=8.8, 5.8 Hz), 7.35-7.30(5H, m), 7.20(1H, td, J=8.2, 2.4 Hz), 7.07(1H, td, J=8.0, 2.6 Hz), 5.11(2H, s), 4.44-4.40(2H, m), 4.12-4.07(2H, m), 4.00(4H, s), 3.18-3.08(2H, m), 2.42(3H, s), 2.13(2H, td, J=13.4, 4.9 Hz), 1.92-1.87(2H, m). LCMS (M + H) calcd for C$_{30}$H$_{30}$FN$_7$O$_6$; 604.23; found: 604.55. |

EXAMPLE 25

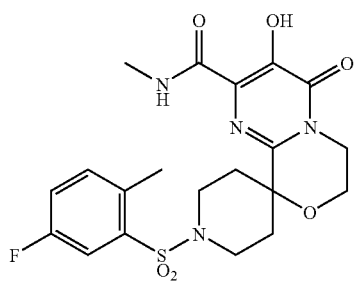

1-(5-Fluoro-2-methylphenylsulfonyl)-3'-hydroxy-N-methyl-4'-oxo-6',7'-dihydro-4'H-spiro[piperidine-4,9'-pyrimido[2,1-c][1,4]oxazine]-2'-carboxamide. A solution of intermediate 56(0.056 g, 0.10 mmol) in 2 M CH$_3$NH$_2$ in MeOH (3 mL) was heated at 70 C for 18 h in a sealed vial. Then, cooled and purified by preparative HPLC to afford product as white solid (0.0464 g, 67%). $^1$H NMR (500 MHz, CDCl$_3$) δ: 12.26 (1H, s), 7.58 (1H, dd, J=8.6, 2.8 Hz), 7.48 (1H, br s), 7.31 (1H, dd, J=8.4, 5.3 Hz), 7.18 (1H, td, J=8.1, 2.8 Hz), 4.02-3.95 (4H, m), 3.80-3.75 (2H, m), 3.05 (3H, d, J=4.9 Hz), 3.01-2.94 (2H, m), 2.60 (3H, s), 2.37 (2H, td, J=13.4, 4.3 Hz), 1.99-1.94 (2H, m), HRMS (M+H) calcd for C$_{20}$H$_{24}$FN$_4$O$_6$S: 467.1401; found: 467.1403.

Intermediate 65

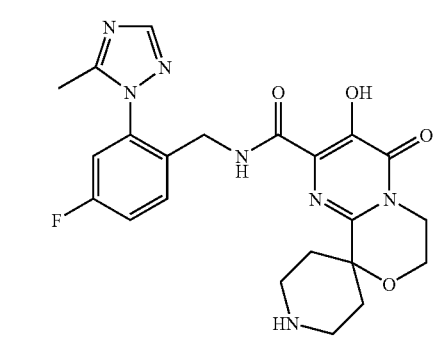

N-(4-Fluoro-2-(5-methyl-1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide. A solution of Example 23 (0.65 g, 1.88 mmol) in EtOAc (30 mL), EtOH (8 mL) and 1N HCl (2 mL, 2 mmol) was shaken with a 10% Pd/C (200 mg) under H$_2$ at 55 psi for 8 h. The mixture was filtered over celite and concentrated. The residue was dissolved in H$_2$O and washed with EtOAc. The aqueous phase was freeze-dried to give the title compound as a pale yellow solid and HCl salt (0.135 g, 14%). $^1$H NMR (300 MHz, CD$_3$OD) δ: 8.96-8.92 (1H, m), 8.73 (1H, s), 7.87 (1H, dd, J=8.4, 5.8 Hz), 7.52-7.43 (2H, m), 4.47 (2H, s), 4.14-4.11 (2H, m), 4.04-4.01 (2H, m), 3.42-3.26 (4H, m), 2.47-2.64 (2H, m), 2.62 (3H, s), 2.24 (2H, d, J=14.3 Hz). LCMS (M+H) calcd for C$_{22}$H$_{25}$FN$_7$O$_4$: 470.19; found: 470.38.

Intermediate 66

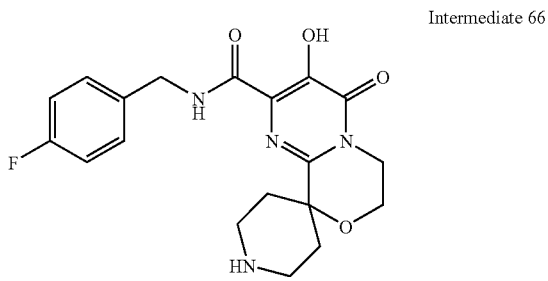

N-(4-Fluorobenzyl)-3'-hydroxy-4'-oxo-6',7'-dihydro-4'H-spiro[piperidine-4,9'-pyrimido[2,1-c][1,4]oxazine]-2'-carboxamide. Following the procedure for Intermediate 65 using Example 22 gave the title compound as white solid and HCl salt (0.63 g, 21%). $^1$H NMR (300 MHz, CD$_3$OD) δ: 7.41 (2H, dd, J=8.0, 5.5 Hz), 7.08 (2H, t, J=8.6 Hz), 4.61 (2H, s), 4.15-4.12 (2H, m), 4.06-4.02 (2H, m), 3.36 (4H, s), 2.59-2.49 (2H, m), 2.28-2.23 (2H, m). LCMS (M+H) calcd for C$_{19}$H$_{22}$FN$_4$O$_4$: 389.16; found: 389.29.

Intermediate 67

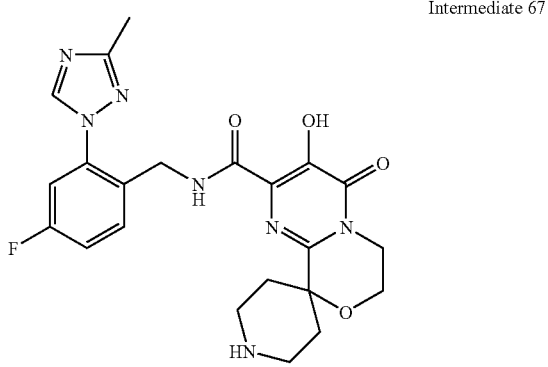

N-(4-Fluoro-2-(3-methyl-1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide. To a solution of Example 24 (0.51 g, 0.85 mmol) in CH$_2$Cl$_2$ (2 mL) was added HBr (10 mL, 33 wt % in HOAC) and the solution was stirred at room temp for 30 min. The solution was concentrated and the residue was partitioned between H$_2$O and EtOAc. The aqueous phase was freeze-dried to give the title compound as a light brown powder (0.30 g, 64%). $^1$H NMR (500 MHz, D$_2$O) δ: 8.66 (1H, s), 7.64 (1H, dd, J=7.5, 6.4 Hz), 7.39 (1H, td, J=8.2,1.7 Hz), 7.31 (1H, dd, J=8.2, 0.9 Hz), 4.61 (2H, s), 4.17-4.15 (2H, m), 4.05-4.03 (2H, m), 3.42-3.40 (2H, m), 3.36-3.30 (2H, m), 2.43-2.36 (2H, m), 2.33 (3H, s), 2.29-2.27 (2H, m). LCMS (M+H) calcd for C$_{22}$H$_{25}$FN$_7$O$_4$: 470.19; found: 470.10.

EXAMPLE 26

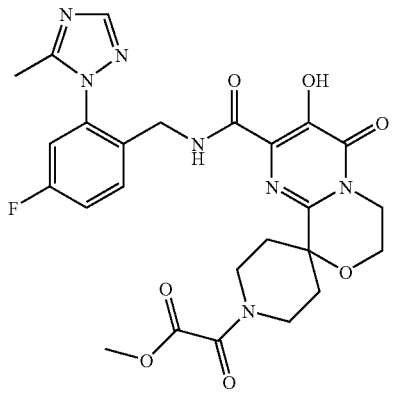

Methyl 2-(2'-(4-fluoro-2-(5-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-yl)-2-oxoacetate. To a mixture of Intermediate 65 (0.135 g, 0.27 mmol) suspended in CH$_2$Cl$_2$ (2 mL) was added diisopropylethylamine (0.14 mL, 0.81 mmol) followed by methyl chlorooxoacetate (0.05 mL, 0.54 mmol). The resulting mixture was stirred at room temp for 18 h. and concentrated. Purification (YMC Combiprep ODS-A, 30 mm×50 mm, MeOH/H$_2$O/0.1% TFA) yielded the title compound as lavender solid (0.686 g, 45% yield). $^1$H NMR (500 MHz, CDCl$_3$) δ: 11.91 (1H, bs), 8.34-8.33 (2H, m), 7.72-7.70 (1H, m), 7.30-7.27 (1H, m), 7.05-7.04 (1H, m), 4.49 (2H, d, J=11.6 Hz), 4.05 (4H, s), 3.92 (3H, s), 3.68 (1H, d, J=12.8 Hz), 3.53-3.49 (2H, m), 3.1-3.05 (1H, m), 3.56 (3H, s), 2.29-2.21 (2H, m), 2.02-2.00 (2H, m). HRMS (M+H) calcd for C$_{25}$H$_{27}$FN$_7$O$_7$: 556.1956; found: 556.1951.

EXAMPLE 27

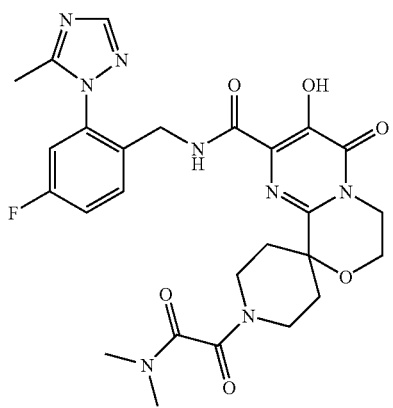

1-(2-(Dimethylamino)-2-oxoacetyl)-N-(4-fluoro-2-(5-methyl-1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide. A solution of Example 26 and 2M Me₂NH/MeOH (2 mL, 4 mmol) was stirred for 18 h. at room temperature. Concentration gave an oil that was purified by chromatography (YMC Combiprep ODS-A, 30 mm×50 mm, MeOH/H₂O/0.1% TFA) to give the title compound as white solid (0.227 g, 36%). ¹H NMR (300 MHz, CDCl3) δ: 8.61 (1H, s), 8.34 (1H, t, J=5.3 Hz), 7.69 (1H, dd, J=8.6, 5.7 Hz), 7.27 (1H, td, J=8.1, 2.3 Hz), 7.01 (1H, dd, J=8.0, 2.2 Hz), 4.48-4.41 (2H, m), (4.18 (1H, dd, J=14.4, 5.3 Hz), 4.02 (4H, s), 3.64-3.59 (1H, m), 3.48-3.40 (1H, m), 3.09-3.04 (1H, m), 3.03 (3H, s), 3.00 (3H, s), 2.54 (3H, s), 2.39-2.29 (1H, m), 2.21-2.10 (1H, m), 1.99-1.88 (1H, m). HRMS (M+H) calcd for C₂₆H₃₀FN₈O₆: 569.2272; found: 569.2272.

EXAMPLE 28

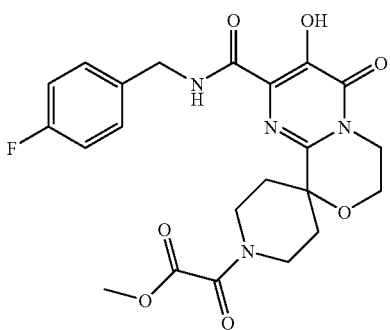

Methyl 2-(2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-yl)-2-oxoacetate. Following the procedure for Example 26 and using Intermediate 66 gave the title compound as white solid (0.0172 g, 24%). ¹H NMR (300 MHz, CDCl₃) δ: 12.20 (1H, s), 7.81 (1H, t, J=6.0 Hz), 7.31 (2H, dd, J=8.6, 5.3 Hz), 7.04-6.99 (2H, m), 4.58 (2H, d, J=4.8 Hz), 4.48-4.42 (1H, m), 4.02 (4H, s), 3.85 (3H, s), 3.60-3.55 (1H, m), 3.50-3.40 (1H, m), 3.06-2.97 (1H, m), 2.19-2.09 (2H, m), 1.94 (2H, t, J=13.2 Hz). LCMS (M+H) calcd for C₂₂H₂₄FN₄O₇: 475.16; found: 475.30.

EXAMPLE 29

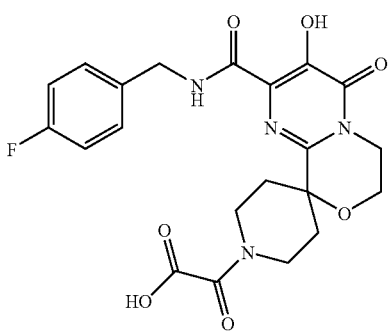

2-(2'-(4-Fluorobenzylcarbamoyl)-3'-hydroxy-4'-oxo-6',7'-dihydro-4'H-spiro[piperidine-4,9'-pyrimido[2,1-c][1,4]oxazine]-1-yl)-2-oxoacetic acid. A solution of Example 28 (0.0147 g, 0.03 mmol) and 2M Me₂NH/MeOH (0.10 mL, 0.2 mmol) in DMF (0.5 mL) was stirred at 80° C. in a sealed tube for 18 h and concentrated. The residue was purified by chromatography (YMC Combiprep ODS-A, 30 mm×50 mm, MeOH/H₂O/0.1% TFA) and the resulting residue was triturated with hot MeOH to give the title compound as white solid (0.0037 g, 25%). ¹H NMR (300 MHz, CDCl₃) δ: 12.21 (1H, bs), 7.92 (1H, t, J=5.8 Hz), 7.29 (2H, dd, J=8.4, 5.5 Hz), 7.00 (2H, t, J=8.6 Hz), 4.63-4.49 (2H, m), 4.46-4.40 (1H, m), 4.19-4.14 (1H, m), 4.01 (4H, s), 3.44 (1H, td, J=13.3, 2.1 Hz), 3.02 (1H, td, J=13.3, 2.4 Hz), 2.25-2.09 (2H, m), 1.98-1.91 (2H, m). HRMS (M+H) calcd for C₂₁H₂₂FN₄O₇: 461.1473; found: 461.1533.

EXAMPLE 30 AND 31

To a suspension of Intermediate 66 (0.58 g, 1.2 mmol) in THF (15 mL) was added N-methylmorpholine (2.7 mL, 2.4 mmol) and stirred for 10 min. To this was added N,N-Dimethyloxamic acid (0.28 g, 2.4 mmol) and then cooled to 0° C. To this mixture was added ethyl chloroformate (0.11 mL, 1.2 mmol), cold bath removed and stirred at room temperature for 18 h. The mixture was washed with H₂O and the organic phase was concentrated. The residue was purified by chromatography (YMC Combiprep ODS-A, 30 mm×50 mm, MeOH/H2O/0.1% TFA) to give Example 30 as pale brown foam (0.0905 g, 15%) and Example 31 as white solid (2% yield).

EXAMPLE 30

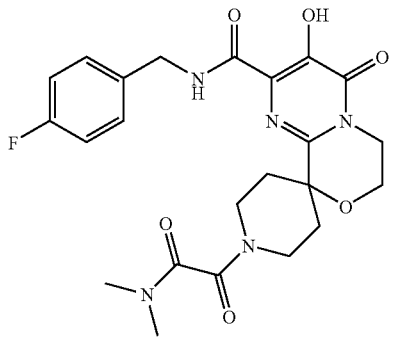

1-(2-(Dimethylamino)-2-oxoacetyl)-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide. ¹H NMR (300 MHz, CDCl₃) δ: 12.23 (1H, s), 7.99 (1H, t, J=6.4 Hz), 7.33-7.29 (2H, m), 7.03-6.97 (2H, m), 4.65-4.48 (2H, m), 4.01 (4H, s), 3.56-3.35 (2H, m), 3.06-2.91 (2H, m), 2.97 (3H, s), 2.95 (3H, s), 2.33-2.10 (2H, m), 1.98-1.84 (2H, m). HRMS (M+H) calcd for C₂₃H₂₇FN₅O₆: 488.1945; found: 488.1967.

EXAMPLE 31

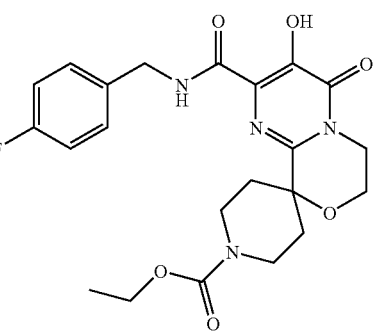

Ethyl 2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-carboxylate. $^1$H NMR (300 MHz, CDCl$_3$) δ: 12.10 (1H, s), 7.77 (1H, J=6.2 Hz), 7.33-7.28 (2H, m), 7.05-7.00 (2H, m), 4.57 (2H, d, J=6.2 Hz), 4.15-3.99 (4H, m), 4.00 (4H, s), 3.12-3.03 (2H, m), 2.11-2.01 (2H, m), 1.87-1.82 (2H, m), 1.23 (3H, t, J=7.1 Hz). HRMS (M+H) calcd for C$_{22}$H$_{26}$FN$_4$O$_6$: 461.1836; found: 461.1858.

EXAMPLES 32 AND 33

To a suspension of Intermediate 67 (0.1 g, 0.18 mmol) in THF (3 mL) was added N-methylmorpholine (0.36 mL, 0.36 mmol) and stirred for 10 min. To this was added N,N-Dimethyloxamic acid (0.02 g, 0.18 mmol) and then cooled to 0° C. To this mixture was added ethyl chloroformate (0.017 mL, 0.18 mmol), cold bath removed and stirred at room temperature for 18 h. The mixture was washed with H$_2$O and the organic phase was concentrated. The residue was purified by chromatography (YMC Combiprep ODS-A, 30 mm×50 mm, MeOH/H2O/0.1% TFA) to give Example 32 as white solid (0.039 g, 38%) and Example 33 as white solid (0.027 g, 28%).

EXAMPLE 32

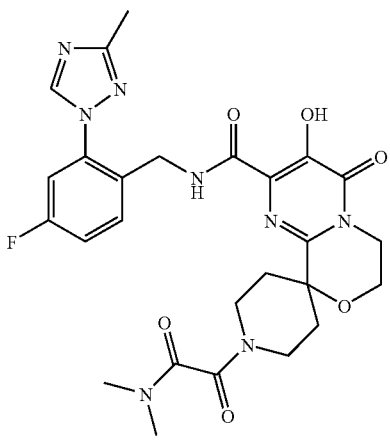

1-(2-(Dimethylamino)-2-oxoacetyl)-N-(4-fluoro-2-(3-methyl-1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide. $^1$H NMR (300 MHz, CDCl$_3$) δ: 12.09 (1H, bs), 8.83-8.81 (1H, m), 8.19 (1H, s), 7.62 (1H, dd, J=8.8, 5.6 Hz), 7.24-7.19 (1H, m), 7.10 (1H, dd, J=8.2, 2.4 Hz), 4.51-4.44 (2H, m), 4.02 (4H, s), 3.58-3.37 (2H, m), 3.08-2.99 (2H, m), 2.98 (3H, s), 2.95 (2H, s), 2.55 (3H, s), 2.24-2.11 (2H, s), 2.00-1.88 (2H, s). HRMS (M+H) calcd for C$_{26}$H$_{30}$FN$_8$O$_6$: 569.2272; found: 569.2258.

EXAMPLE 33

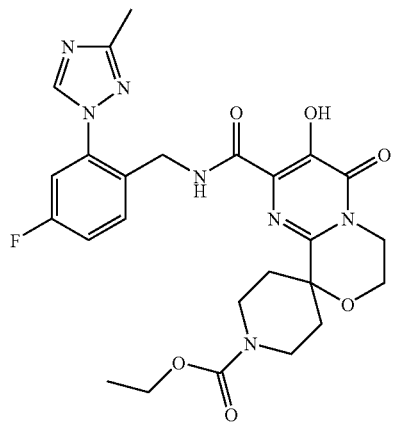

Ethyl 2'-(4-fluoro-2-(3-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate. $^1$H NMR (300 MHz, CDCl$_3$) δ: 12.21 (1H, s), 8.64-8.60 (1H, m), 8.34 (1H, s), 7.66 (1H, dd, J=8.4, 5.8 Hz), 7.15 (1H, td, J=8.1, 2.3 Hz), 7.06, 1H, dd, J=8.2, 2.4 Hz), 4.43 (2H, s), 4.13-4.03 (4H, m), 4.00 (4H, s), 3.13-3.05 (2H, m), 2.48 (3H, s), 2.21-2.10 (2H, m), 1.90-1.85 (2H, m), 1.24 (3H, t, J=6.9 Hz). HRMS (M+H) calcd for C$_{25}$H$_{29}$FN$_7$O$_6$: 542.2163; found: 542.2148.

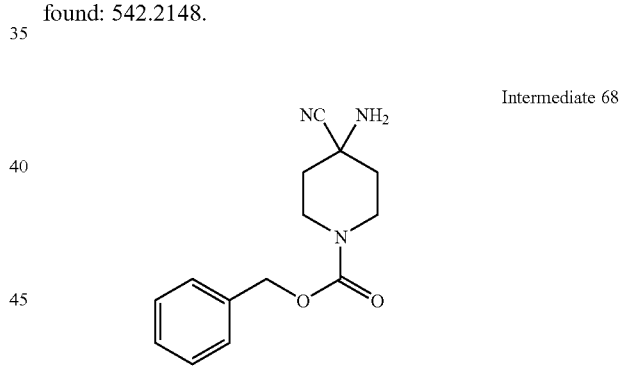

Intermediate 68

Benzyl 4-amino-4-cyanopiperidine-1-carboxylate. To a stirred mixture of ammonium hydroxide (856 mL), 1-(benzyloxycarbonyl)-4-piperidinone (1.07 mol) and ammonium chloride (113.42 g, 2.14 mol) in methanol (350 mL) was added sodium cyanide (105 g, 2.14 mmol) and stirred at room temperature for 36 h. The mixture was extracted with CH$_2$Cl$_2$ two times. The organic phases were combined and dried (Na$_2$SO$_4$) and concentrated. The pale yellow oil was dissolved in CH$_2$Cl$_2$ and ethereal HCl was added (699 mL, 1.4 mol, 2 M solution). The resulting white suspension was stirred at room temp 18 h. The solid was collected by filtration to give the title compound as white solid (314.5 g, 100% yield). $^1$H NMR (300 MHz, CDCl$_3$) δ: 7.33-7.27 (5H, m), 5.10 (2H, s), 4.00-3.97 (2H, m), 3.25 (2H, td, J=12.2, 2.8 Hz), 1.97-1.93 (2H, m), 1.78 (2H, s), 1.65-1.59 (2H, m).

Intermediate 69

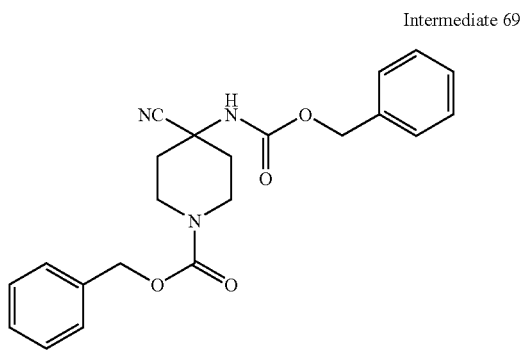

Benzyl 4-(benzyloxycarbonylamino)-4-cyanopiperidine-1-carboxylate. To a stirred mixture of Intermediate 68 (20.0 g, 68 mmol) and sodium carbonate (7.2 g, 68 mmol) in THF (300 mL) and H$_2$O (200 mL) at 0° C. was added benzyl chloroformate (10.8 mL, 74.8 mmol), and the mixture was gradually warmed to room temperature over 18 h. Then, mixture was diluted with EtOAc and the organic phase was washed with sat'd aq. NaHCO$_3$, brine, dried (Na$_2$SO$_4$) and concentrated. The resulting oil was purified by flash chromatography eluting with 1:1 EtOAc/hexanes to give the title compound as waxy pale yellow solid (19.5 g, 73% yield). $^1$H NMR (300 MHz, CDCl$_3$) δ: 7.36-7.25 (10H, m), 5.39 (1H, bs), 5.10 (2H, s), 5.09 (2H, s), 3.97-3.94 (2H, m), 3.29-3.22 (2H, m), 2.31-2.27 (2H, m), 1.75-1.66 (2H, m). LCMS (M+H) calcd for C$_{22}$H$_{24}$N$_3$O$_4$: 394.17; found: 394.30.

Intermediate 70

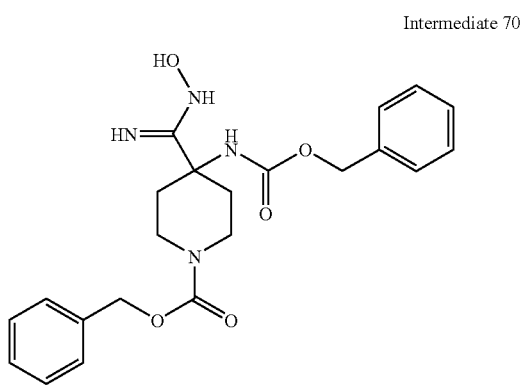

Benzyl 4-(benzyloxycarbonylamino)-4-(N-hydroxycarbamimidoyl)piperidine-1-carboxylate. Following the procedure for Intermediate 14 using Intermediate 69 gave colorless oil that was carried on without purification. $^1$H NMR (300 MHz, CDCl$_3$) δ: 7.34-7.28 (10H, m), 5.11-5.03 (4H, m), 4.04-3.94 (1H, m), 3.87-3.76 (1H, m), 3.33-3.13 (2H, m), 2.37-2.32 (1H, m), 2.17-1.98 (2H, m), 1.78-1.69 (1H, m). LCMS (M+H) calcd for C$_{22}$H$_{27}$N$_4$O$_5$: 427.19; found: 427.42.

Intermediate 71

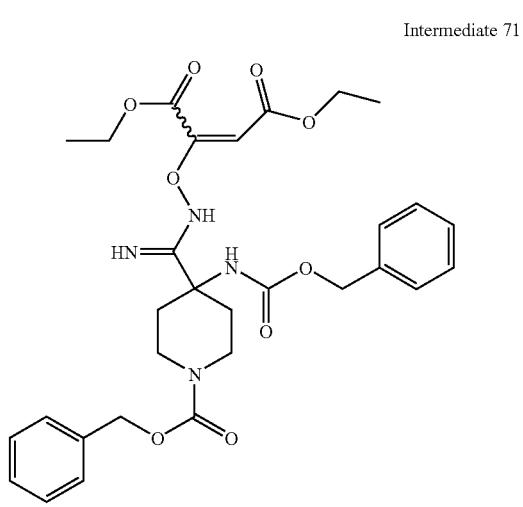

Diethyl 2-(1-(benzyloxycarbonyl)-4-(benzyloxycarbonylamino)piperidine-4-carboximidamidooxy)but-2-enedioate. Following the procedure for Intermediate 15 using Intermediate 70 gave the title compound as pale yellow oil (19.31 g, 61% yield over 2 steps). $^1$H NMR (300 MHz, CDCl$_3$) δ: 7.33-7.28 (10H, m), 5.86 (1H, bs), 5.70 (1H, d, J=14.3 Hz), 5.51 (1H, bs), 5.08 (2H, d, J=4.4 Hz), 5.04 (2H, d, J=1.5 Hz), 4.90 (1H, d, J=6.9 Hz), 4.35-4.20 (2H, m), 4.16-4.07 (2H, m), 3.78-3.67 (2H, m), 3.32-3.25 (2H, m), 2.19-1.99 (3H, m), 1.69 (1H, bs), 1.35-1.20 (6H, m). LCMS (M+H) calcd for C$_{30}$H$_{37}$N$_4$O$_9$: 597.25; found: 597.56.

Intermediate 72

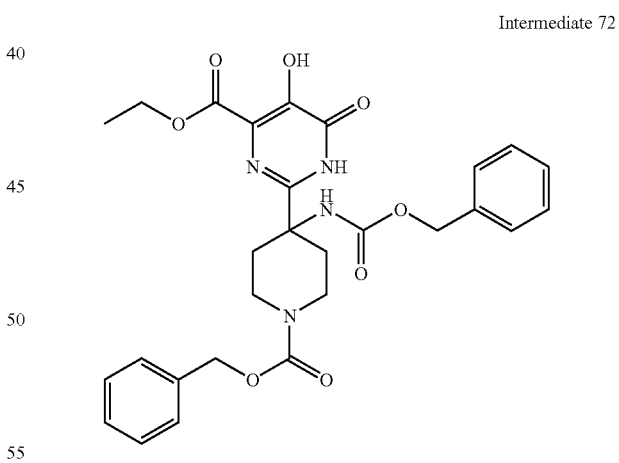

Ethyl 2-(1-(benzyloxycarbonyl)-4-(benzyloxycarbonylamino)piperidin-4-yl)-5-hydroxy-6-oxo-1,6-dihydropyrimidine-4-carboxylate. Following the procedure for Intermediate 16 using Intermediate 71 gave the title compound as tan solid (3.2365 g, 18% yield). $^1$H NMR (300 MHz, CDCl$_3$) δ: 11.85 (1H, bs), 11.01 (1H, bs), 7.36-7.22 (10H, m), 5.98 (1H, bs), 5.13 (2H, s), 4.98 (2H, s), 4.43 (2H, q, J=7.12 Hz), 3.95 (2H, bs), 3.30-3.27 (2H, m), 2.25-2.17 (4H, m), 1.43 (3H, t, J=7.0 Hz). LCMS (M+H) calcd for C$_{28}$H$_{31}$N$_4$O$_8$: 551.21; found: 551.53.

Intermediate 73

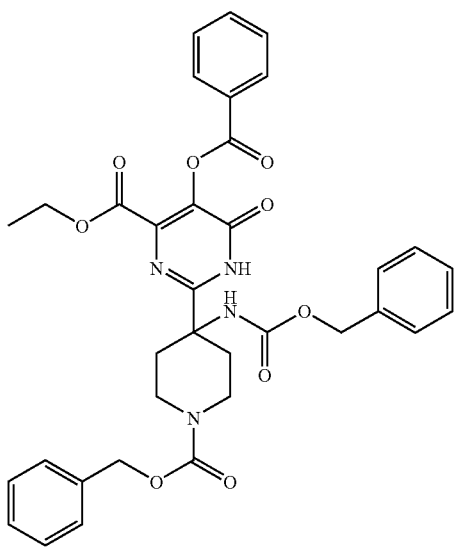

Ethyl 5-(benzoyloxy)-2-(1-(benzyloxycarbonyl)-4-(benzyloxycarbonylamino)-piperidin-4-yl)-6-oxo-1,6-dihydropyrimidine-4-carboxylate. To a solution of Intermediate 72 (3.23 g, 5.88 mmol) dissolved in pyridine (50 mL) was added benzoic anhydride (1.46 g, 6.5 mmol) and the mixture stirred at room temperature for 18 h. After concentration, the residue was dissolved in EtOAc, washed with 1N NaOH, 1N HCl, H$_2$O, brine, dried (Na$_2$SO$_4$) and concentrated to give the title compound as brown foam (3.93 g, 100% yield). $^1$H NMR (300 MHz, CDCl$_3$) δ: 8.12-8.09 (2H, m), 8.05-8.02 (2H, m), 7.63-7.53 (2H, m), 7.47-7.38 (3H, m), 7.34-7.19 (2H, m), 5.10 (2H, s), 4.98 (2H, s), 4.24 (2H, q, J=7.1 Hz), 4.00 (2H, bs), 3.12 (2H, t, J=11.2 Hz), 2.29-2.12 (4H, m), 1.11 (3H, t, J=7.1 Hz). LCMS (M+H) calcd for C$_{35}$H$_{35}$N$_4$O$_9$: 655.24; found: 655.59.

Intermediate 74

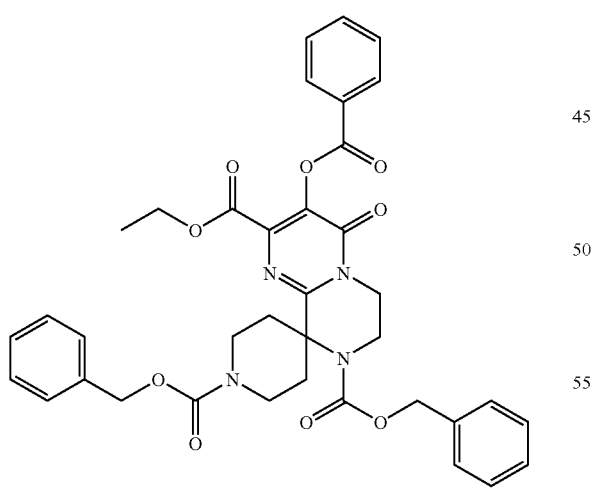

1,8'-Dibenzyl 2'-ethyl 3'-(benzoyloxy)-4'-oxo-6',7'-dihydrospiro[piperidine-4,9'-pyrazino[1,2-a]pyrimidine]-1,2',8' (4'H)-tricarboxylate. To a solution of Intermediate 73 (3.9 g, 5.8 mmol) in DMF (15 mL) was added potassium carbonate (1.6 g, 6.8 mmol) followed by dibromoethane (1.17 mL, 13.7 mmol). The resulting mixture was stirred at 70° C. for 6 h then concentrated. The residue was partitioned between H2O and EtOAc and the organic phase was washed with brine, dried (Na2SO4) and concentrated. The oil was purified by flash chromatography eluting with 1%-100% EtOAc/Hexane to give the title compound as white foam (1.35 g, 34% yield). LCMS (M+H) calcd for C$_{37}$H$_{37}$N$_4$O$_9$: 681.25; found: 681.67.

Intermediate 75

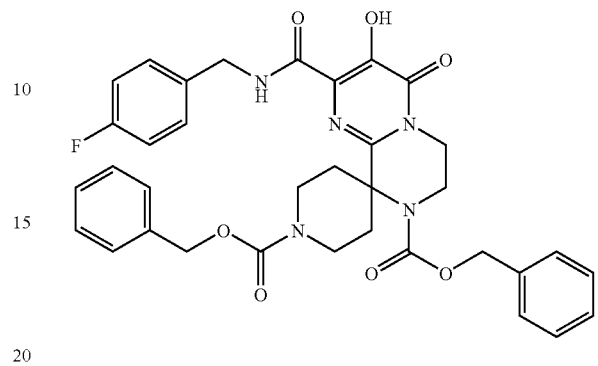

Dibenzyl 2'-(4-fluorobenzylcarbamoyl)-3'-hydroxy-4'-oxo-6',7'-dihydrospiro[piperidine-4,9'-pyrazino[1,2-a]pyrimidine]-1,8'(4'H)-dicarboxylate. Following the procedure for Example 1 using Intermediate 74 gave the title compound as yellow foam (0.2228 g, 8.5% yield).

Intermediate 76

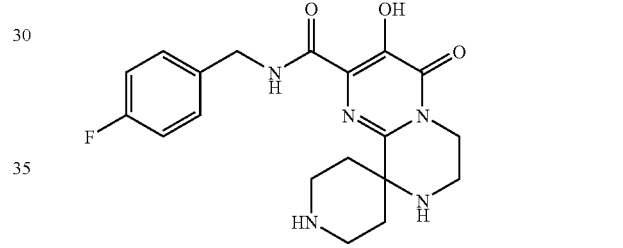

N-(4-Fluorobenzyl)-3'-hydroxy-4'-oxo-4',6',7',8'-tetrahydrospiro[piperidine-4,9'-pyrazino[1,2-a]pyrimidine]-2'-carboxamide. Following the procedure for Intermediate 67 using Intermediate 75 gave white solids that were triturated by MeOH to give the title compound as white solid HBr salt (100% yield). $^1$H NMR (500 MHz, DMSO) δ: 11.98 (1H, bs), 9.16 (1H, t, J=6.4 Hz), 8.66 (1H, bs), 8.55 (1H, bs), 7.37 (2H, dd, J=8.5, 5.8 Hz), 7.19-7.16 (2H, m), 4.52 (2H, d, J=6.1 Hz), 3.74 (2H, t, J=5.5 Hz), 3.17 (4H, bs), 3.07 (2H, t, J=5.0 Hz), 2.50-2.44 (2H, m), 1.93 (2H, d, J=13.7 Hz). HRMS (M+H) calcd for C$_{19}$H$_{23}$N$_5$O$_3$F: 388.1785; found: 388.1804.

EXAMPLE 34

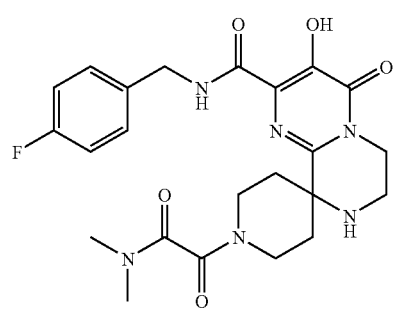

1-(2-(Dimethylamino)-2-oxoacetyl)-N-(4-fluorobenzyl)-3'-hydroxy-4'-oxo-4',6',7',8'-tetrahydrospiro[piperidine-4,9'-pyrazino[1,2-a]pyrimidine]-2'-carboxamide. Following the procedure for Example 31 using Intermediate 76 gave the title compound as a white solid (8% yield). $^1$H NMR (500 MHz, CDCl$_3$) δ: 12.13 (1H, s), 7.95 (1H, t, J=6.1 Hz), 7.36-7.33 (2H, m), 7.05-7.02 (2H, m), 4.66-4.55 (2H, m), 3.99-3.87 (2H, m), 3.52-3.49 (2H, m), 3.26-3.20 (2H, m), 2.99 (3H, s), 2.96 (3H, s), 3.02-2.93 (2H, m), 2.37-2.26 (2H, m), 1.74 (2H, t, J=15.7 Hz). HRMS (M+H) calcd for $C_{23}H_{28}N_6O_5F$: 487.21; found: 487.20.

EXAMPLE 35

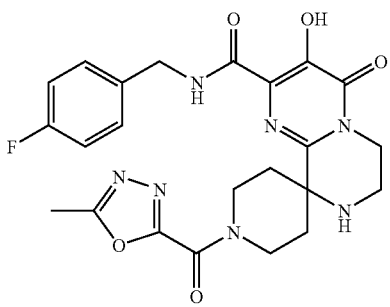

N-(4-Fluorobenzyl)-3'-hydroxy-1-(5-methyl-1,3,4-oxadiazole-2-carbonyl)-4'-oxo-4',6',7',8'-tetrahydrospiro[piperidine-4,9'-pyrazino[1,2-a]pyrimidine]-2'-carboxamide. To a suspension of potassium 5-methyl-1,3,4-oxadiazole-2-carboxylate (Belyk, K., M. et al WO 2006/060712; 0.25 g, 1.10 mmol) in CH$_2$Cl$_2$ (2 mL) with catalytic DMF was added oxalyl chloride (1.7 mL, 3.3 mmol, 2 M in CH$_2$Cl$_2$). The mixture was stirred at room temp for 30 min. and concentrated. The residue was taken up in CH$_2$Cl$_2$ (2 mL) and added to a mixture of Intermediate 76 (0.068 g, 0.12 mmol) and diisopropylethylamine (0.267 mL, 1.53 mmol) in CH$_2$Cl$_2$ (2 mL) and stirred at room temperature. Concentration and purification (YMC Combiprep ODS-A, 30 mm×50 mm, MeOH/H$_2$O/0.1% TFA) gave the title compound as an orange solid (0.0057 g, 9% yield). $^1$H NMR (500 MHz, CD$_3$OD) δ: 9.04 (1H, bs), 7.26-7.23 (2H, m), 6.95-6.91 (2H, m), 4.58 (2H, bs), 4.44 (2H, s), 3.97 (2H, bs), 3.39 (4H, bs), 2.51 (3H, s), 2.52-2.49 (2H, m), 1.99 (2H, bs).

Intermediate 77

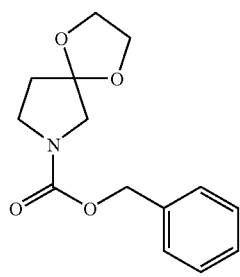

Benzyl 1,4-dioxa-7-azaspiro[4.4]nonane-7-carboxylate. A solution of benzyl 3-oxopyrrolidine-1-carboxylate (11.2 g, 51.09 mmol), ethylene glycol (2.4 g, 38.67 mmol) and TsOH.H$_2$O (10 mg) in benzene (100 mL) was heated at reflux using Dean-Stork condenser. After 20 h, the reaction mixture was cooled, diluted with EtOAc (100 mL), washed with water (2×25 mL), brine (25 mL), dried (MgSO4), filtered and concentrated to give yellow oil. Flash column chromatography purification on silica gel column with 1:4 followed by 3:7 EtOAc:hexanes provided desired product (10.32 g, 100%) as colorless liquid. $^1$H NMR (500 MHz, CDCl$_3$) δ: 7.38-7.28 (5H, m), 5.13 (2H, s), 3.99-3.92 (4H, m), 3.58-3.54 (2H, m), 3.45 (2H, d, J=10.7 Hz), 2.07-2.02 (2H, m).

Intermediate 78

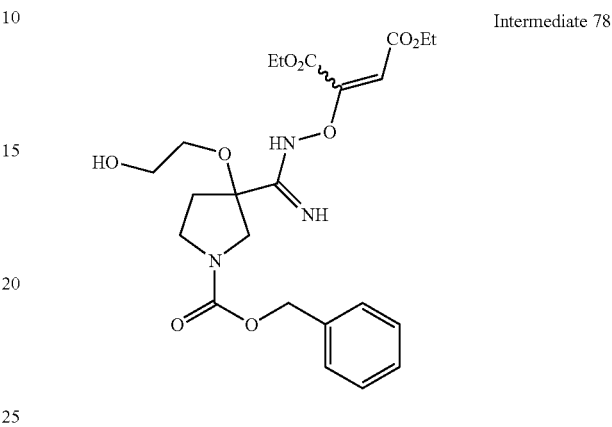

Diethyl 2-(1-(benzyloxycarbonyl)-3-(2-hydroxyethoxy)pyrrolidine-3-carboximidamidooxy)but-2-enedioate. To a stirred mixture of Intermediate 77 (10.3 g, 39 mmol) and ZnI$_2$ (1.2767 g, 4 mmol) was added TMS-CN (11 mL, 82 mmol) at room temperature. After stirring 72 h, the reaction mixture was diluted with EtOAc (200 mL) and cooled in ice-water bath. To this was added saturated Na$_2$CO$_3$ (20 mL) and stirred for 30 min. Then, aqueous layer separated and organic layer washed with brine (20 mL), dried (Na$_2$SO$_4$), filtered and concentrated to give viscous oil which was dissolved in EtOH (50 mL) and treated with 50% aq. NH$_2$OH (3.06 mL, 50 mmol). After 24 h at room temperature, the reaction mixture was concentrated under vaccuo and the resulting residue was re-dissolved in EtOH (50 m) and treated with diethyl acetylenedicarboxylate (6.4 mL, 40 mmol). After 24 h, the reaction mixture was concentrated and the resulting yellow residue was taken up in EtOAc (200 mL), washed with water (2×30 mL), brine (30 mL), dried (Na$_2$SO$_4$), filtered and concentrated to afford yellow oil. Flash column chromatography purification on silica gel column with 30% and 40% EtOAc:Hex followed by 9:1 CH$_2$Cl$_2$:MeOH provided desired product (7.459 g, 39%) as brown paste and mixture of isomers. HRMS (M+H) calcd for $C_{23}H_{32}N_3O_9$: 494.2139; found: 494.2154.

Intermediate 79

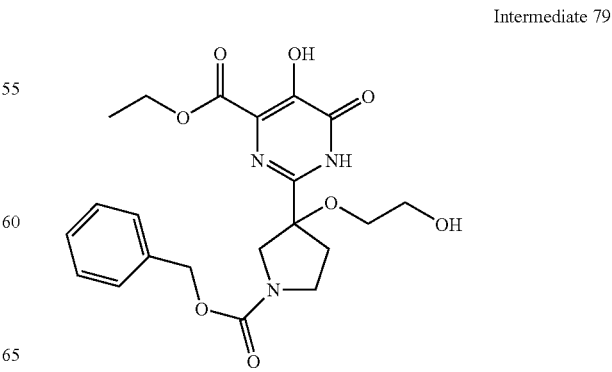

Ethyl 2-(1-(benzyloxycarbonyl)-3-(2-hydroxyethoxy)pyrrolidin-3-yl)-5-hydroxy-6-oxo-1,6-dihydropyrimidine-4-carboxylate. A solution of Intermediate 78 (7.459 g, 15.1143 mmol) in xylenes was heated at 150 C for 3 h and then the resulting dark reaction mixture was cooled and concentrated. The residue was taken up in EtOAc (200 mL), extracted with 0.2M NaOH (4×25 mL). The combined aqueous phases acidified with conc. HCl and extracted with CH$_2$Cl$_2$ (3×50 mL). The combined CH$_2$Cl$_2$ extracts dried (Na$_2$SO$_4$), filtered and concentrated to provide desired product (3.31 g, 90% pure) as dark paste which was used in the next step without purification. (M+H) calcd for C$_{21}$H$_{26}$N$_3$O$_8$: 448.1720; found: 448.1732.

Intermediate 80

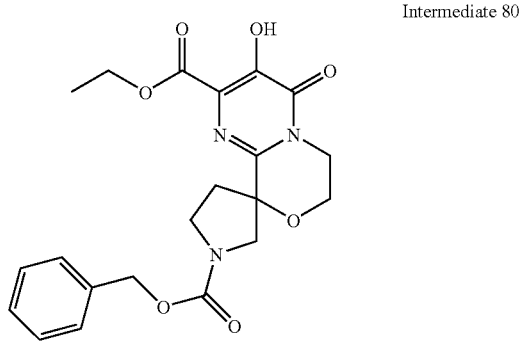

1'-Benzyl 2-ethyl 3-hydroxy-4-oxo-6,7-dihydro-4H-spiro[pyrimido[2,1-c][1,4]oxazine-9,3'-pyrrolidine]-1,2-dicarboxylate. To a stirred solution of Intermediate 79 (3.31 g) in THF (100 mL) was added Et$_3$N (4.2 mL, 30 mmol) followed by MsCl (1.16 mL, 15 mmol). The resulting reaction mixture was stirred for 24 h at room temperature and concentrated. The residue was taken up in EtOAc (150 mL), washed with water (2×30 mL), brine (30 mL), dried (Na$_2$SO$_4$), filtered and concentrated to provide desired product as brown paste which was used in the next step without purification.

A solution of above brown paste in 0.2M NaOEt/EtOH (50 mL) was stirred at room temperature for 16 h and concentrated. The residue was taken up in water (50 mL), washed with Et$_2$O (3×50 mL), acidified with conc. HCl and extracted with CH$_2$Cl$_2$ (3×50 mL). The combined CH$_2$Cl$_2$ extracts dried (Na$_2$SO$_4$), filtered and concentrated to provide desired product (2.093 g, 32%) as brown foam. HRMS (M+H) calcd for C$_{21}$H$_{24}$N$_3$O$_7$: 430.1614; found: 430.1621.

EXAMPLE 36

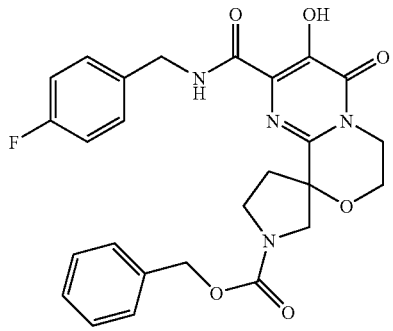

Benzyl 2-(4-fluorobenzylcarbamoyl)-3-hydroxy-4-oxo-6,7-dihydro-4H-spiro[pyrimido[2,1-c][1,4]oxazine-9,3'-pyrrolidine]-1'-carboxylate. A mixture of Intermediate 80 (0.859 g, 2 mmol), 4-fluorobenzylamine (1.25 g, 10 mmol) and Et$_3$N (10 mL, 7.143 mmol) in EtOH (40 mL) was stirred at reflux for 5 h. Then, cooled and purified by preparative HPLC using water/MeOH containing 0.1F TFA as eluant to afford desired product (0.4963 g, 49%) as light purple solid. $^1$H NMR (500 MHz, CDCl$_3$) δ: 12.20 (1H, br s), 7.78-7.67 (1H, m), 7.38-7.26 (7H, m), 7.05-7.01 (2H, m), 5.16-5.02 (2H, m), 4.62-4.47 (2H, m), 4.13-3.97 (4H, m), 3.90-3.72 (3H, m), 3.62-3.56 (1H, m), 2.50-2.42 (1H, m), 2.30-2.24 (1H, m). HRMS (M+H) calcd for C$_{26}$H$_{26}$N$_4$O$_6$F: 509.1836; found: 509.1815.

EXAMPLE 37

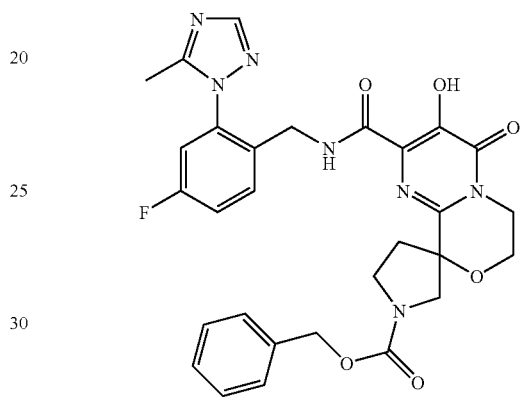

Benzyl 2-(4-fluoro-2-(5-methyl-1H-1,2,4-triazol-1-yl)benzylcarbamoyl)-3-hydroxy-4-oxo-6,7-dihydro-4H-spiro[pyrimido[2,1-c][1,4]oxazine-9,3'-pyrrolidine]-1'-carboxylate. Prepared according to the procedure for Example 36 using Intermediate 80 and (4-fluoro-2-(5-methyl-1H-1,2,4-triazol-1-yl)phenyl)methan-amine hydrochloride to afford desired product (62%) as light purple solid. $^1$H NMR (500 MHz, CDCl$_3$) δ: 12.02-11.24 (1H, br), 8.32-8.24 (1H, m), 8.06 (0.5H, s), 8.03 (0.5H, s), 7.65-7.62 (1H, m), 7.38-7.25 (5H, m), 7.18-7.14 (1H, m), 7.01-6.98 (1H, m), 5.18-5.11 (2H, m), 4.36-4.23 (2H, m), 4.17-3.93 (5H, m), 3.87-3.78 (2H, m), 3.67-3.60 (1H, m), 2.61-2.45 (4H, m), 2.33-2.27 (1H, m). HRMS (M+H) calcd for C$_{29}$H$_{29}$N$_7$O$_6$F: 590.2163; found: 590.2178.

Intermediate 81

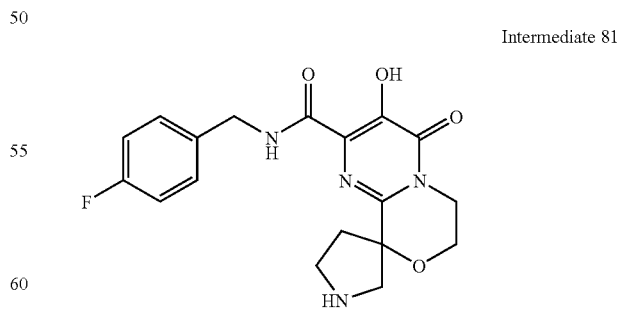

N-(4-Fluorobenzyl)-3-hydroxy-4-oxo-6,7-dihydro-4H-spiro[pyrimido[2,1-c][1,4]oxazine-9,3'-pyrrolidine]-2-carboxamide. To a stirred solution of Example 36 (0.388 g, 0.763 mmol) in 1,4-dioxane (5 mL) was added 33 wt % HBr in AcOH (1 mL) at room temperature. After 24 h, the resulting white slurry was diluted with Et2O (50 mL), filtered and dried to afford desired product as 1:1:1 product:HBr:dioxane adduct 0.3521 g, 85%). $^1$H NMR (500 MHz, DMSO-$d_6$) δ: 12.30 (1H, s), 9.48 (1H, t, J=6.4 Hz), 9.17 (1H, s), 7.39-7.36 (2H, m), 7.20-7.15 (2H, m), 4.57-4.48 (2H, m), 4.08-4.04 (2H, m), 3.94-3.84 (2H, m), 3.75-3.69 (1H, m), 3.60-3.49 (6H, m), 3.47-3.31 (4H, m), 2.69-2.62 (1H, m), 2.44-2.38 (1H, m). HRMS (M+H) calcd for $C_{18}H_{20}N_4O_4F$: 375.1469; found: 375.1466.

Intermediate 82

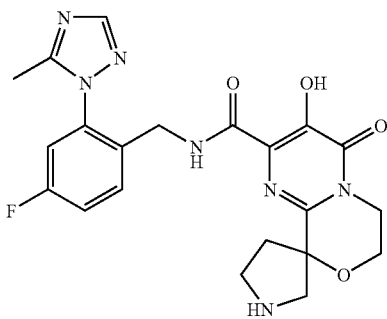

N-(4-Fluoro-2-(5-methyl-1H-1,2,4-triazol-1-yl)benzyl)-3-hydroxy-4-oxo-6,7-dihydro-4H-spiro[pyrimido[2,1-c][1,4]oxazine-9,3'-pyrrolidine]-2-carboxamide. To a stirred solution of Example 37 (1.1358 g, 1.9265 mmol) in 1,4-dioxane (10 mL) was added 33 wt % HBr in AcOH (2 mL) at room temperature. Immediately upon addition of HBr/AcOH to the reaction, solids precipitated out of the reaction mixture. So, 3 mL of anhydrous MeOH was added and stirred for 2 h. Then, the reaction mixture was purified by preparative HPLC using water/MeOH containing 0.1% TFA to afford desired product (0.448 g, 41%) as white solid. $^1$H NMR (500 MHz, DMSO-$d_6$) δ: 1205 (1H, s), 9.35-9.28 (1H, br s), 9.27-9.19 (1H, br s), 9.14 (1H, t, J=6.1 Hz), 8.12 (1H, s), 7.57-7.53 (2H, m), 7.48-7.44 (1H, m), 4.27 (2H, d, J=6.1 Hz), 4.09-4.05 (2H, m), 3.91-3.86 (2H, m), 3.70-3.49 (3H, m), 3.42-3.34 (1H, m), 2.66-2.59 (1H, m), 2.45-2.39 (1H, m), 2.33 (3H, s). HRMS (M+H) calcd for $C_{21}H_{23}N_7O_4F$: 456.1796; found: 456.1805.

EXAMPLE 38

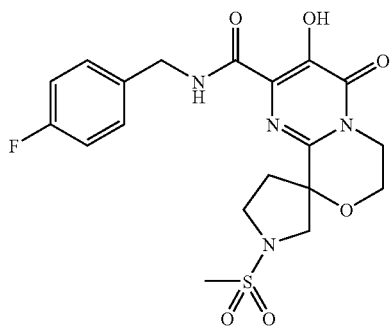

N-(4-Fluorobenzyl)-3-hydroxy-1'-(methylsulfonyl)-4-oxo-6,7-dihydro-4H-spiro[pyrimido[2,1-c][1,4]oxazine-9,3'-pyrrolidine]-2-carboxamide. To a stirred suspension of Intermediate 81 (0.10 g, 0.184 mmol) in $CH_2Cl_2$ (10 mL) was added DIEA (0.17 mL, 10 mmol) at room temperature. After 5 min, MsCl (0.04 mL, 0.5 mL) was added to the resulting clear homogenous reaction mixture and stirred for an additional 1 h. Then, the reaction mixture was concentrated and the residue was dissolved in THF (10 mL) and treated with 40 wt % aq. $Me_2NH$ (0.5 mL). After 18 h, the reaction mixture was concentrated and the resulting residue was taken up in EtOH (25 mL), washed with 1N aq. HCl (10 mL), water (10 mL), brine (10 mL), dried ($Na_2SO_4$), filtered and concentrated to give yellow paste which was crystalized from water/MeOH to afford desired product (0.0656 g, 79%) as off-white solid. $^1$H NMR (500 MHz, $CDCl_3$) δ: 12.29 (1H, s), 8.16 (1H, s), 7.35-7.32 (2H, m), 7.03 (2H, t, J=8.6 Hz), 4.60-4.50 (2H, m), 4.13-4.08 (2H, m), 4.06-3.98 (3, m), 3.79-3.74 (1H, m), 3.57 (1H, d, J=11.6 Hz), m3.49-3.42 (1H, m), 2.90 (3H, s), 2.56-2.50 (1H m), 2.38-2.33 (1H, m). HRMS (M+H) calcd for $C_{19}H_{22}N_4O_6SF$: 453.1244; found: 453.1251. Anal. calcd for $C_{19}H_{21}N_4O_6SF$: C, 50.43; H, 4.67; N, 12.38; found: C, 50.43; H, 4.77; N, 12.27.

EXAMPLE 39

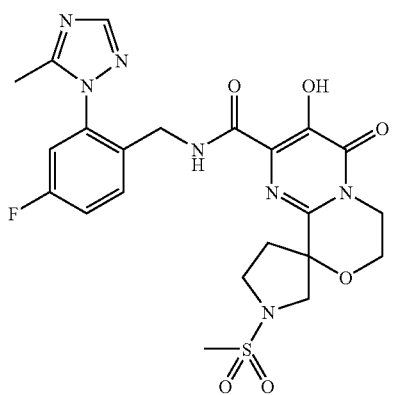

N-(4-Fluoro-2-(5-methyl-1H-1,2,4-triazol-1-yl)benzyl)-3-hydroxy-1'-(methylsulfonyl)-4-oxo-6,7-dihydro-4H-spiro[pyrimido[2,1-c][1,4]oxazine-9,3'-pyrrolidine]-2-carboxamide. Prepared according to the procedure for Example 38 using Intermediate 82 to afford desired product (49%) as purple solid. $^1$H NMR (500 MHz, $CDCl_3$) δ: 12.14-11.86 (1H, br), 8.51 (1H, s), 8.15 (1H, s), 7.68-7.65 (1H, m), 7.28-7.24 (1H, m), 7.02 (1H, dd, J=8.2, 2.4 Hz), 4.35-4.24 (2H, m), 4.11-4.00 (5H, m), 3.81-3.76 (1H, m), 3.63 (1H, d, J=11.6 Hz), 3.51-3.46 (1H, m), 2.90 (3H, s), 2.65-2.58 (1H, m), 2.50 (3H, s), 2.40-2.34 (1H, m). HRMS (M+H) calcd for $C_{22}H_{25}N_7O_6FS$: 534.1571; found: 534.1572. Anal. calcd for $C_{22}H_{24}N_7O_6FS.0.5$ TFA: C, 46.78; H, 4.18; N, 16.60; found: C, 46.63; H, 3.65; N, 16.47.

EXAMPLE 40

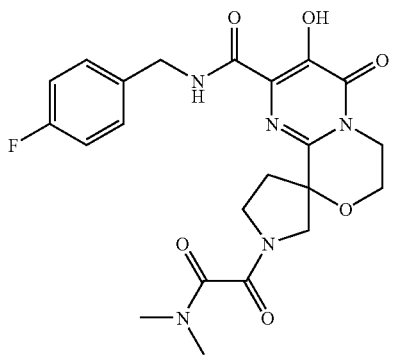

1'-(2-(Dimethylamino)-2-oxoacetyl)-N-(4-fluorobenzyl)-3-hydroxy-4-oxo-6,7-dihydro-4H-spiro[pyrimido[2,1-c][1,4]oxazine-9, 3'-pyrrolidine]-2-carboxamide. To a stirred mixture of 2-(dimethylamino)-2-oxoacetic acid (0.129 g, 1.10 mmol) in $CH_2Cl_2$ (10 mL) was added N-methylmorpholine (0.132 mL, 1.2 mmol). After 5 min, 1M isopropyl chloroformate in toluene (1 mL, 1 mmol) was added to the clear reaction mixture and stirred for 1h at room temperature. The (isopropyl carbonic) 2-(dimethylamino)-2-oxoacetic anhydride reagent prepared here was used in the subsequent reactions.

To a stirred solution of Intermediate 81 (0.0815 g, 0.15 mmol) and DIEA (0.08 mL, 0.5 mmol) in $CH_2Cl_2$ (5 mL) was added 2 mL of freshly prepared (isopropyl carbonic) 2-(dimethylamino)-2-oxoacetic anhydride (0.182 mmol) at room temperature. After 4 h. the reaction mixture was concentrated and the residue was taken up in EtOAc (50 mL), washed with 0.1N aq. HCl (2×10 mL), brine (10 mL), dried ($Na_2SO_4$), filtered and concentrated to give yellow solid which was purified by preparative HPLC using water/MeOH containing 0.1% TFA to afford desired product (0.0485 g, 68%) as white powder. $^1$H NMR (500 MHz, $CDCl_3$) δ: 12.99-11.93 (1H, br), 8.49 (0.6H, t, J=6.4 Hz), 8.32 (0.4H, t, J=5.8 Hz), 7.39-7.34 (2H, m), 7.04-6.99 (2H, m), 4.63-4.49 (2H, m), 4.22 (1H, d, J=11.9 Hz), 4.13-3.99 (4.6H, m), 3.91-3.85 (0.4H, m), 3.68-3.57 (2H, m), 3.07 (1.8H, s),3.04 (1.2H, s), 3.00 (1.8H, s), 2.96 (1.2H, s), 2.60-2.31 (2H, m). HRMS (M+H) calcd for $C_{22}H_{25}N_5O_6F$: 474.1789; found: 474.1787. Anal. calcd for $C_{22}H_{24}N_5O_6F.0.1H_2O.0.2TFA$: C, 54.02; H, 4.94; N, 14.06; found: C, 53.64; H, 5.13; N, 13.98.

EXAMPLE 41

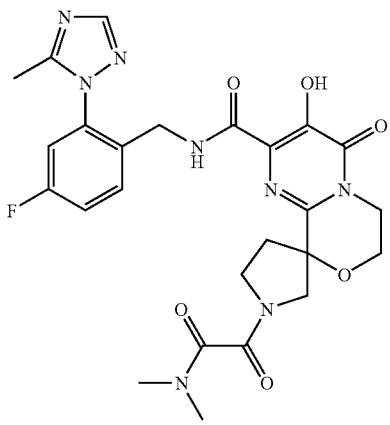

1'-(2-(Dimethylamino)-2-oxoacetyl)-N-(4-fluoro-2-(5-methyl-1H-1,2,4-triazol-1-yl)benzyl)-3-hydroxy-4-oxo-6,7-dihydro-4H-spiro[pyrimido[2,1-c][1,4]oxazine-9,3'-pyrrolidine]-2-carboxamide. Prepared according to the procedure for Example 40 using Intermediate 82 to afford desired product (22%) as white powder. $^1$H NMR (500 MHz, $CDCl_3$) δ: 12.23 (0.6H, s), 12.09 (0.4H, s), 8.66 (0.6H, t, J=6.4 Hz), 8.59 (0.4H, t, J=6.4 Hz), 8.10 (0.4H, s),8.02 (0.6H, s), 7.65-7.58 (1H, m), 7.28-7.20 (1H, m), 7.01-6.97 (1H, m), 4.42-4.26 (2H, m), 4.19 (1H, d, J=12.2 Hz), 4.08-3.89 (4H, m), 3.79-3.62 (2H, m), 3.12-3.08 (1H, m), 3.06 (1.8H, s), 3.04 (1.2H, s), 2.98 (1.8H,s), 2.96 (1.2H,s), 2.68-2.52 (1H, m), 2.45 (3H, s), 2.42-2.33 (1H, m). HRMS (M+H) calcd for $C_{25}H_{28}N_8O_6F$: 555.2116; found: 555.2141. Anal. calcd for $C_{25}H_{27}N_8O_6F.0.1H_2O.0.35TFA$: C, 51.77; H, 4.66; N, 18.79; found: C, 51.64; H, 4.94; N, 19.05.

EXAMPLE 42

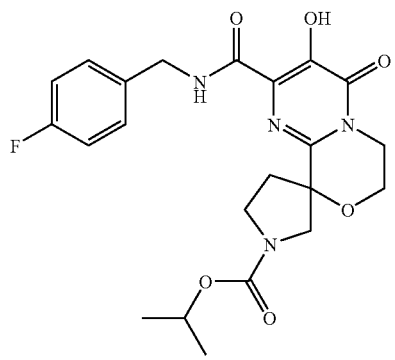

Isopropyl 2-(4-fluorobenzylcarbamoyl)-3-hydroxy-4-oxo-6,7-dihydro-4H-spiro[pyrimido[2,1-c][1,4]oxazine-9, 3'-pyrrolidine]-1'-carboxylate. To a stirred suspension of Intermediate 81 (0.0815 g, 0.15 mmol) and DIEA (0.08 mL, 0.5 mmol) in $CH_2Cl_2$ (5 mL) was added isopropyl chloroformate in toluene (1M, 0.16 mL, 0.16 mmol) at room temperature. After 1 h, the resulting clear reaction mixture was concentrated and the residue was purified by preparative HPLC using water/MeOH containing 0.1% TFA to afford desired product (0.0643 g, 93%) as light purple solid. $^1$H NMR (500 MHz, $CDCl_3$) δ: 12.32-12.09 (1H, br), 7.84-7.69 (1H, m), 7.37-7.28 (2H, m), 7.08-7.01 (2H, m), 4.95-4.77 (1H, m), 4.67-4.49 (2H, m), 4.15-3.97 (4H, m), 3.90-3.65 (3H, m), 3.60-3.50 (1H, m), 2.50-2.40 (1H, m), 2.30-2.23 (1H, m), 1.30-1.09 (6H, m). HRMS (M+H) calcd for $C_{22}H_{26}N_4O_6F$: 461.1836; found: 461.1857. Anal. calcd for $C_{22}H_{25}N_4O_6F.0.25TFA$: C, 55.27; H, 5.21; N, 11.46; found: C, 55.57; H, 5.00; N, 11.40.

EXAMPLE 43

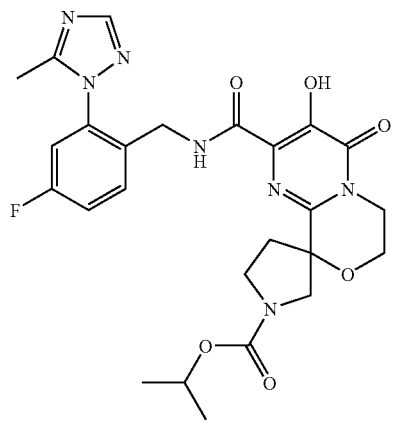

Isopropyl 2-(4-fluoro-2-(5-methyl-1H-1,2,4-triazol-1-yl) benzylcarbamoyl)-3-hydroxy-4-oxo-6,7-dihydro-4H-spiro [pyrimido[2,1-c][1,4]oxazine-9,3'-pyrrolidine]-1'-carboxylate. Prepared according to the procedure for Example 42 using Intermediate 82 to afford desired product (23%) as purple solid. $^1$H NMR (500 MHz, CDCl$_3$) δ: 12.18-11.77 (1H, br), 8.48-8.40 (1H, m), 8.03 (1H, s), 7.68-7.63 (1H, m), 7.30-7.26 (1H, m), 7.04-7.01 (1H, m), 4.99-4.89 (1H, m), 4.45-3.96 (6H, m), 3.93-3.88 (2H, m), 3.83-3.72 (1H, m), 3.65-3.52 (1H, m), 2.63-2.51 (1H, m), 2.50 (3 s, m), 2.32-2.25 (1H, m), 1.30-1.19 (6H, m). HRMS (M+H) calcd for C$_{25}$H$_{29}$N$_7$O$_6$F: 542.2163; found: 542.2171.

EXAMPLE 44 AND 44

To a stirred suspension of potassium 5-methyl-1,3,4-oxadiazole-2-carboxylate (0.0332 g, 0.2 mmol) CH$_2$Cl$_2$ (5 mL) containing cat. DMF was added oxalyl chloride (2M, 0.5 mL, 10 mmol) at room temperature. After 1 h, the resulting clear reaction mixture was concentrated and the resulting residue re-suspended in CH$_2$Cl$_2$ (10 mL) and added to the stirred solution of Intermediate 81 (0.072 g, 0.15 mmol) and Et$_3$N (0.14 mL, 10 mmol) in CH$_2$Cl$_2$ (5 mL) at room temperature. After 18 h, the reaction mixture was concentrated and the residue was purified by preparative HPLC using water/MeOH containing 0.1% TFA to afford Example 44 (0.0361 g, 56%) as tan solid and Example 45 (0.022 g, 35%) as brown solid.

EXAMPLE 44

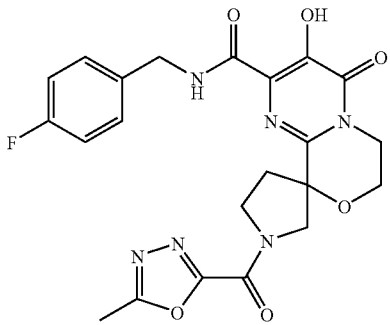

N-(4-Fluorobenzyl)-3-hydroxy-1'-(5-methyl-1,3,4-oxadiazole-2-carbonyl)-4-oxo-6,7-dihydro-4H-spiro[pyrimido[2,1-c][1,4]oxazine-9,3'-pyrrolidine]-2-carboxamide. $^1$H NMR (500 MHz, CDCl$_3$) δ: 12.27 (1H, s), 7.69 (1H, br s), 7.34-7.27 (2H, m), 7.06-7.00 (2H, m), 4.62-4.51 (3.5H, m), 4.40 (0.5H, d, J=12.8 Hz), 4.17-4.00 (6.5H, m), 3.88-3.80 (0.5H, m), 2.61 (3H, d, J=7.6 Hz), 2.57-2.37 (2H, m). HRMS (M+H) calcd for C$_{22}$H$_{22}$N$_6$O$_6$F: 485.1585; found: 485.1571. Anal. calcd for C$_{22}$H$_{21}$N$_6$O$_6$F.0.25TFA.1H$_2$O: C, 50.90; H, 4.41; N, 15.83; found: C, 50.79; H, 3.85; N, 15.52.

EXAMPLE 45

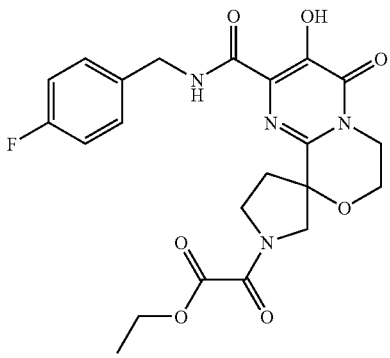

Ethyl 2-(2-(4-fluorobenzylcarbamoyl)-3-hydroxy-4-oxo-6,7-dihydro-4H-spiro[pyrimido[2,1-c][1,4]oxazine-9,3'-pyrrolidine]-1'-yl)-2-oxoacetate. $^1$H NMR (500 MHz, CDCl$_3$) δ: 12.30 (1H, s), 7.80-7.74 (1H, m), 7.35-7.31 (2H, m), 7.04 (2H, t, J=8.6 Hz), 4.65-4.50 (2H, m), 4.36-4.26 (2H, m), 4.13-3.92 (7H, m), 3.86-3.80 (0.5H, m), 3.70-3.64 (0.5H, m), 2.57-2.31 (3H, m), 1.38-1.32 (2H, m). HRMS (M+H) calcd for C$_{22}$H$_{24}$N$_4$O$_7$F: 475.1629; found: 475.1622. Anal. calcd for C$_{22}$H$_{23}$N$_4$O$_7$F.0.25TFA.0.25H$_2$O: C, 53.26; H, 4.72; N, 11.04; found: C, 52.93; H, 4.68; N, 110.10.

EXAMPLE 46 AND 47

Prepared according to the procedure for Example 44 using Intermediate 82 to afford Example 46 (35%) as light yellow solid and Example 47 (33%) as brown solid.

EXAMPLE 46

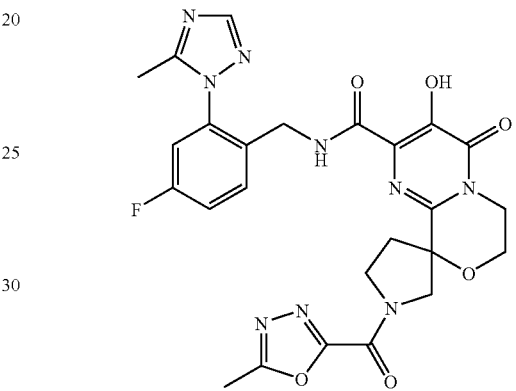

N-(4-Fluoro-2-(5-methyl-1H-1,2,4-triazol-1-yl)benzyl)-3-hydroxy-1'-(5-methyl-1,3,4-oxadiazole-2-carbonyl)-4-oxo-6,7-dihydro-4H-spiro[pyrimido[2,1-c][1,4]oxazine-9,3'-pyrrolidine]-2-carboxamide. $^1$H NMR (500 MHz, CDCl$_3$) δ: 12.33-11.23 (1H, br), 8.32 (0.5H, t, J=6.4 Hz), 8.27 (0.5H, t, J=6.4 Hz), 8.10 (0.5H, s), 8.09 (0.5H, s), 7.67-7.63 (1H, m), 7.31-7.25 (1H, m), 7.04-7.01 (1H, m), 4.63-4.57 (1H, m), 4.51-4.01 (8.5H, m), 3.91-3.85 (0.5H. m), 2.70-2.39 (2H, m), 2.64 (1.5H, s), 2.63 (1.5H, s), 2.52 (1.5H, s), 2.51 (1.5H,s). HRMS (M+H) calcd for C$_{25}$H$_{25}$N$_9$O$_6$F: 566.1912; found: 566.1912. Anal. calcd for C$_{25}$H$_{24}$N$_9$O$_6$F.1.1TFA.0.3CH$_2$Cl$_2$: C, 46.10; H, 3.62; N, 17.60; found: C, 46.34; H, 3.53; N, 16.67.

EXAMPLE 47

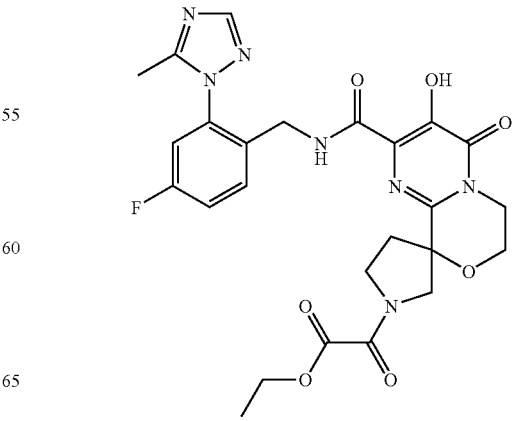

Ethyl 2-(2-(4-fluoro-2-(5-methyl-1H-1,2,4-triazol-1-yl)benzylcarbamoyl)-3-hydroxy-4-oxo-6,7-dihydro-4H-spiro[pyrimido[2,1-c][1,4]oxazine-9,3'-pyrrolidine]-1'-yl)-2-oxoacetate. $^1$H NMR (500 MHz, CDCl$_3$) δ: 12.11-11.02 (1H, br), 8.26-8.21 (1H, m), 8.17 (0.5H, s), 8.12 (0.5H, s), 7.68-7.63 (1H, m), 7.32-7.25 (1H, m), 7.05-7.01 (1H, m), 4.46-3.69 (12H, m), 2.65-2.48 (1H, m), 2.52 (3H, s), 2.43-2.34 (1H, m), 1.39-1.33 (3H, m). HRMS (M+H) calcd for C$_{25}$H$_{27}$N$_7$O$_7$F: 556.1956; found: 556.1940. Anal. calcd for C$_{25}$H$_{26}$N$_7$O$_7$F.1.3TFA: C, 47.11; H, 3.91; N, 13.93; found: C, 46.85; H, 3.54; N, 13.60.

Intermediate 83

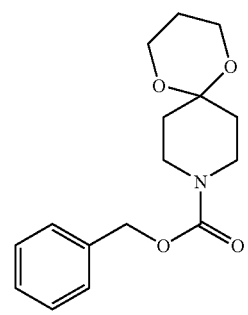

Benzyl 1,5-dioxa-9-azaspiro[5.5]undecane-9-carboxylate. To a solution of 1,5-dioxa-9-aza spiro[5.5]undecane (15.0 g, 95.4 mmol) and triethylamine (17.6 mL, 126 mmol) in THF (140 mL) cooled to 0° C. was added dropwise a solution of benzyl chloroformate (14 mL, 97.5 mmol) dissolved in THF (30 mL). The resulting mixture was stirred at room temp for 18 h. After diluting with EtOAc, the mixture was washed with water and brine and dried (Na$_2$SO$_4$). Concentration gave yellow oil that was purified by flash chromatography eluting with 20%-50% EtOAc/hexane to give the title compound as colorless oil (18.9 g, 68% yield). $^1$H NMR (300 MHz, CDCl$_3$) δ: 7.36-7.27 (5H, m), 5.09 (2H, s), 3.89-3.85 (4H, m), 3.51-3.47 (4H, m), 1.87-1.66 (6H, m). LCMS (M+H) calcd for C$_{16}$H$_{22}$NO$_4$: 292.15; found: 292.00.

Intermediate 84

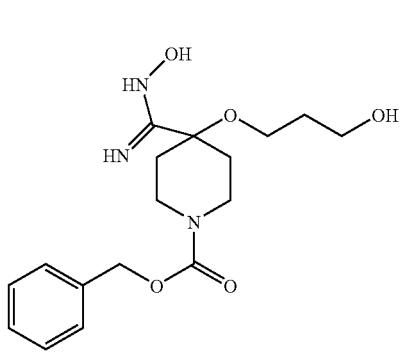

Benzyl 4-(N-hydroxycarbamimidoyl)-4-(3-hydroxypropoxy)piperidine-1-carboxylate. Added to a solution of Intermediate 83 (16.9 g, 58.10 mmol) in CH$_2$Cl$_2$ (10 mL) was BF3.Et2O (1.85 mL, 14.7 mmol). The solution was stirred for 10 min before adding trimethylsilylcyanide (7.8 mL, 58.1 mmol) with water bath cooling to control the exotherm. The mixture was stirred at room temperature for 3 days and concentrated. The crude mixture was taken up in THF (20 mL) and EtOH (100 mL). Added to this was hydroxylamine (3.5 mL, 58.10 mmol, 50 wt % in water) and the mixture was stirred at room temperature for 18 h. The mixture was concentrated to give the crude desired product that was carried on without purification. LCMS (M+H) cacld for C$_{17}$H$_{26}$N$_3$O$_5$: 352.18; found: 352.00.

Intermediate 85

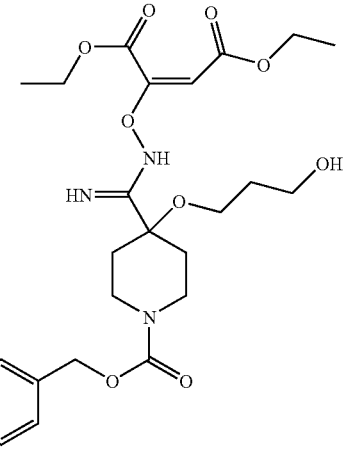

Diethyl 2-(1-(benzyloxycarbonyl)-4-(3-hydroxypropoxy)piperidine-4-carboximidamidooxy)maleate. Acetylene dicarboxylate (10 mL, 58 mmol) was added to a solution of crude Intermediate 84 (58 mmol) dissolved in ethanol/THF (100/20 mL) and the solution was stirred at room temperature for 24 h. Concentration followed by flash chromatography (0%-100% EtOAc/hexane) gave the title compound as a pale yellow oil (21.35 g, 70% yield). $^1$H NMR (300 MHz, CDCl$_3$) δ: 7.33-7.29 (5H, m), 5.72 (1H, d, J=14.3 Hz), 5.22 (1H, bs), 5.09 (2H, d, J=5.9 Hz), 4.35-4.22 (2H, m), 4.17-4.05 (3H, m), 3.95-3.80 (1H, m), 3.78-3.73 (2H, m), 3.47-3.42 (2H, m), 3.21-3.14 (2H, m), 1.91-1.78 (4H, m), 1.60 (2H, bs), 1.35-1.20 (6H, m). LCMS (M+H) calcd for C$_{26}$H$_{36}$N$_3$O$_9$: 522.24; found: 522.00.

Intermediate 86

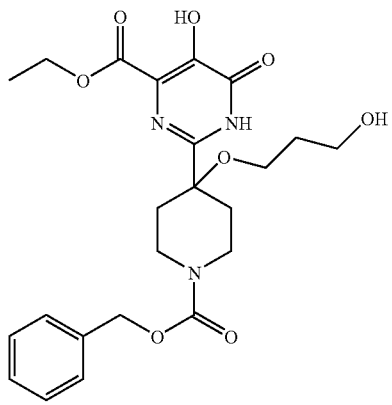

Ethyl 2-(1-(benzyloxycarbonyl)-4-(3-hydroxypropoxy)piperidin-4-yl)-5-hydroxy-6-oxo-1,6-dihydropyrimidine-4-carboxylate. Following the procedure for Intermediate 16 except using Intermediate 85 (21 g, 40 mmol), and the residue was taken up in EtOAc and extracted with aqueous Na$_2$CO$_3$.

The aqueous phase was acidified with concentrated HCl and extracted with EtOAc. The organic phase was dried (Na$_2$SO$_4$) and concentrated to give the title compound as a brown foam (10.72 g, 56% yield). $^1$H NMR (300 MHz, CDCl$_3$) δ: 10.79 (1H, bs), 7.34-7.28 (5H, m), 5.10 (2H, s), 4.64 (2H, q, J=7.2 Hz), 4.10-3.96 (2H, m), 3.86 (2H, t, J=5.5 Hz), 3.41 (2H, bs), 3.41 (2H, bs), 3.21-3.16 (2H, m), 2.12-2.02 (2H, m), 1.90-1.84 (4H, m), 1.40 (3H, t, J=7.1 Hz). LCMS (M+H) calcd for C$_{23}$H$_{30}$N$_3$O$_8$: 476.20; found: 476.00.

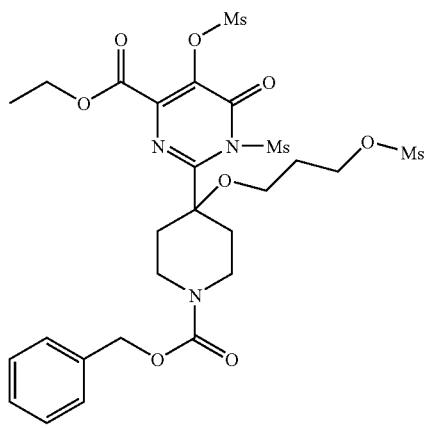

Intermediate 87

Ethyl 2-(1-(benzyloxycarbonyl)-4-(3-(methylsulfonyloxy)propoxy)piperidin-4-yl)-1-(methylsulfonyl)-5-(methylsulfonyloxy)-6-oxo-1,6-dihydropyrimidine-4-carboxylate. Following the procedure for Intermediate 63 except using Intermediate 86 (11.19 g, 23 mmol) gave the title compound as brown oil that was carried on without purification. LCMS (M+H) calcd for C$_{26}$H$_{36}$N$_3$O$_{14}$S$_3$: 710.13; found: 710.00.

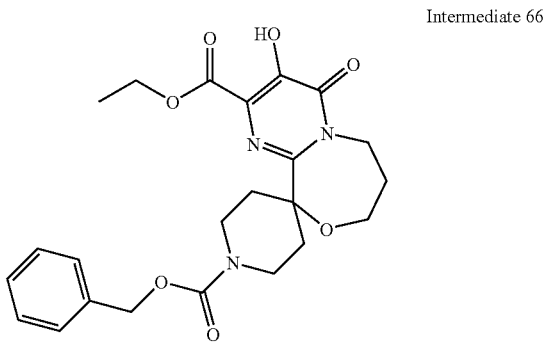

Intermediate 66

1-Benzyl 2'-ethyl 3'-hydroxy-4'-oxo-4',6',7',8'-tetrahydrospiro[piperidine-4,10'-pyrimido[2,1-c][1,4]oxazepine]-1,2'-dicarboxylate. Following the procedure for Intermediate 64 except using Intermediate 87 (23 mmol) gave the title compound as a pale brown solid sodium salt (3.98 g, 38% yield over 2 steps). $^1$H NMR (300 MHz, DMSO) δ: 7.37-7.29 (5H, m), 5.08 (2H, s), 4.27 (2H, bs), 4.08 (2H, q, J=7.1 Hz), 3.88-3.83 (2H, m), 3.62 (2H, t, J=6.0 Hz), 3.21 (2H, bs), 2.51-2.48 (4H, m), 1.86-1.74 (2H, m), 1.19 (3H, t, J=7.1 Hz).

HRMS (M+H) calcd for C$_{23}$H$_{28}$N$_3$O$_7$: 458.1927; found: 458.1910. Anal calcd for C$_{23}$H$_{27}$N$_3$O$_7$.0.5 H$_2$O/1 Na: C, 56.55; H, 5.57; N, 8.60; found: C, 56.53; H, 5.55; N, 8.38.

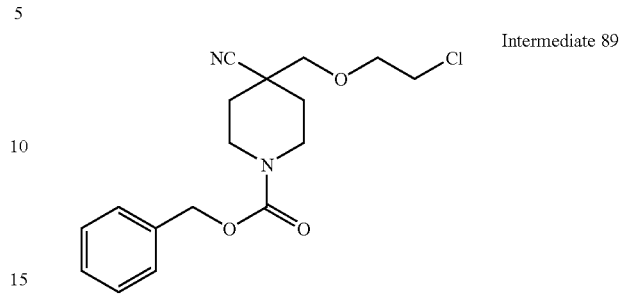

Intermediate 89

Benzyl 4-((2-chloroethoxy)methyl)-4-cyanopiperidine-1-carboxylate. A solution of benzyl 4-cyanopiperidine-1-carboxylate (10.0 g, 41 mmol) and 2-chloroethyl chloromethyl ether (6.3 mL, 49.2 mmol) in THF (80 mL) was cooled to −78° C. To this solution was added drop wise LiHMDS (50 mL, 50 mmol, 1N in THF) and the resulting mixture was gradually warmed to room temp over 5 h. The reaction was quenched with water and the organic phase was washed with brine, dried (Na$_2$SO$_4$) and concentrated. The residue was purified by flash chromatography (1:1 EtOAc/hexane) to give the title compound as yellow oil (11.9 g, 86% yield). $^1$H NMR (300 MHz, CDCl$_3$) δ: 7.33-7.31 (5H, m), 5.10 (2H, d, J=5.9 Hz), 4.21 (2H, bs), 3.79-3.76 (2H, m), 3.63-3.60 (2H, m), 3.52-3.51 (2H, m), 3.09 (2H, bs), 1.96-1.92 (2H, m), 1.55-1.51 (2H, m).

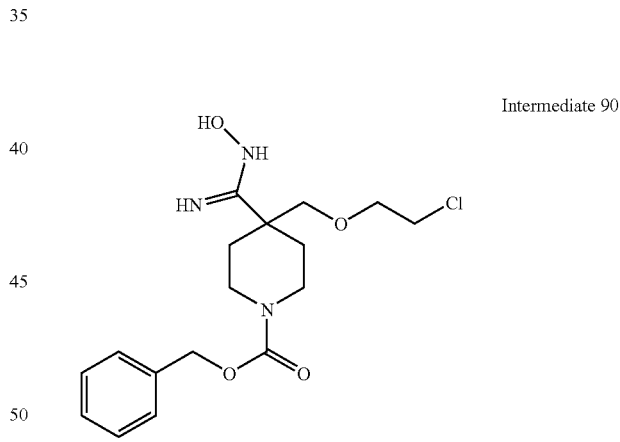

Intermediate 90

Benzyl 4-((2-chloroethoxy)methyl)-4-(N-hydroxycarbamimidoyl)piperidine-1-carboxylate. To a stirred solution Intermediate 89 (11.9 g, 35 mmol) in EtOH (50 mL) and THF (20 mL) was added 50% aqueous hydroxylamine (21 mL, 350 mmol). The resulting mixture was stirred at 90° C. for 4 h. The solution was cooled and concentrated, and the residue was partitioned between EtOAc and water. The organic phase was washed with water, brine and dried (Na$_2$SO$_4$). Concentration gave the title compound as colorless oil (12.20 g) that was carried on without further purification. LCMS (M+H) calcd for C$_{17}$H$_{25}$ClN$_3$O$_4$: 370.15; found: 370.09.

Intermediate 91

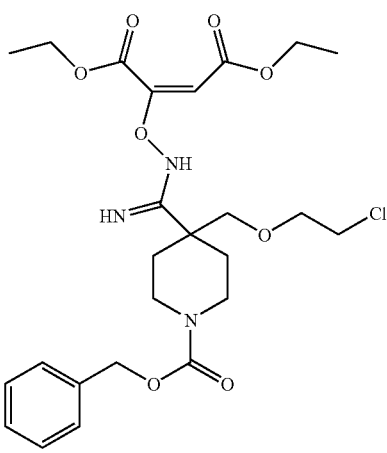

Diethyl 2-(1-(benzyloxycarbonyl)-4-((2-chloroethoxy)methyl)piperidine-4-carboximidamidooxy)maleate. Following the procedure for Intermediate 15 using Intermediate 90 (12.20 g) with purification by flash chromatography (35% EtOAc/hexane) gave the title compound as pale yellow oil (9.29 g, 49% yield over 2 steps). $^1$H NMR (300 MHz, CDCl$_3$) δ: 7.33-7.27 (5H, m), 5.70 (1H, s), 5.58 (1H, s), 5.55 (1H, s), 5.29 (1H, s), 5.08 (2H, d, J=4.4 Hz), 4.35-4.07 (4H, m), 3.83-3.77 (2H, m), 3.70-3.65 (2H, m), 3.62-3.58 (2H, m), 3.40 (2H, dd, J=15.0, 4.0 Hz), 3.26-3.15 (2H, m), 2.08-1.98 (2H, m), 1.44-1.36 (2H, m), 1.35-1.20 (6H, m). LCMS (M+H) calcd for $C_{25}H_{35}ClN_3O_8$: 540.21; found: 540.07.

Intermediate 92

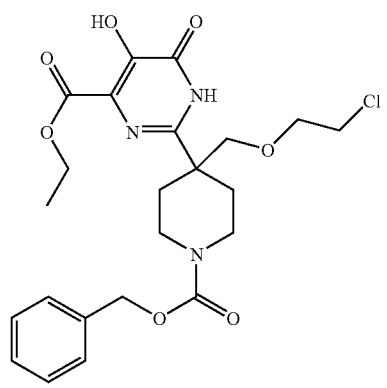

Ethyl 2-(1-(benzyloxycarbonyl)-4-((2-chloroethoxy)methyl)piperidin-4-yl)-5-hydroxy-6-oxo-1,6-dihydropyrimidine-4-carboxylate. Following the procedure for Intermediate 16 using Intermediate 91 (9.29 g, 17.2 mmol) gave the title compound as brown foam (5.56 g, 65% yield). LCMS (M+H) calcd for $C_{23}H_{29}ClN_3O_7$: 494.16; found: 494.11.

Intermediate 93

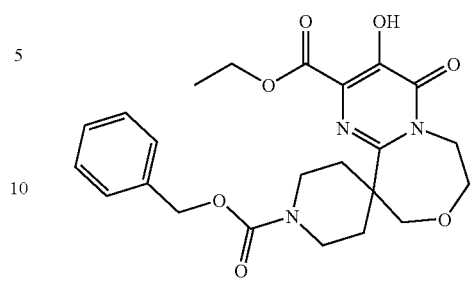

1-Benzyl 2'-ethyl 3'-hydroxy-4'-oxo-4',6',7',9'-tetrahydrospiro[piperidine-4,1'-pyrimido[1,2-d][1,4]oxazepine]-1,2'-dicarboxylate. To a solution of Intermediate 92 (4.1 g, 8.4 mmol) in DMF (10 mL) was added potassium carbonate (2.3 g, 16.7 mmol) and the resulting mixture was stirred at 90° C. for 8 h. The mixture was cooled and concentrated. The resulting residue was partitioned between EtOAc and water. The aqueous phase was acidified with concentrated HCl and extracted with EtOAc. The organic phase was dried (Na$_2$SO$_4$) and concentrated. The resulting oil was purified by flash chromatography (0% to 3% MeOH/CH$_2$Cl$_2$) to give the title compound as pale orange foam (0.6938 g, 18% yield). $^1$H NMR (300 MHz, CDCl$_3$) δ: 10.45 (1H, bs), 7.36-7.27 (1H, m), 5.10 (2H, s), 4.40 (2H, q, J=7.1 Hz), 3.91-3.31 (10H, m), 2.29-2.25 (2H, m), 1.72-1.59 (2H, m), 1.38 (3H, t, J=7.1 Hz). LCMS (M+H) calcd for $C_{23}H_{28}N_3O_7$: 458.19; found: 458.18.

Intermediate 94

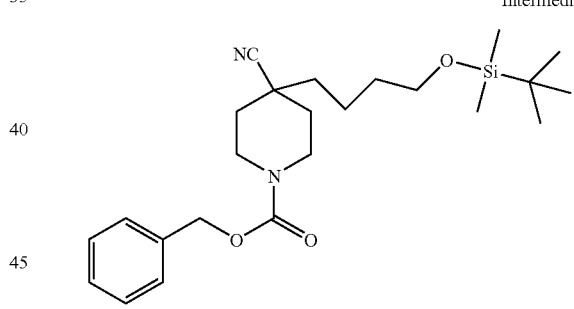

Benzyl 4-(4-(tert-butyldimethylsilyloxy)butyl)-4-cyanopiperidine-1-carboxylate. To a stirred solution of benzyl 4-cyanopiperidine-1-carboxylate (10 g, 41 mmol) and iodo-tert-butyldimethylsilane butane (12.6 mL, 49 mmol) in THF (80 mL) cooled to −78° C. was added LiHMDS (50 mL, 50 mmol, 1M in THF) dropwise over 30 min. The resulting mixture was stirred while gradually warming to room temperature for 18 h. After quenching with water, the organic phase was diluted with EtOAc and washed with water, brine and dried (Na$_2$SO$_4$). After concentration, the residue was purified by flash chromatography (10% to 20% EtOAc/hexane) to give the title compound as yellow oil (11.88 g, 67% yield). $^1$H NMR (300 MHz, CDCl$_3$) δ: 7.34-7.28 (5H, m), 5.09 (2H, s), 4.17 (2H, bs), 3.59 (2H, t, J=5.3 Hz), 3.07 (2H, bs), 1.89 (2H, d, J=13.2 Hz), 1.53 (6H, bs), 1.43-1.34 (2H, m), 0.85 (9H, s), 0.01 (6H, s). LCMS (M+H): 431.20.

Intermediate 95

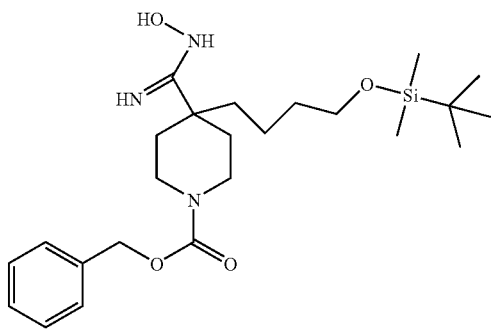

Benzyl 4-(4-(tert-butyldimethylsilyloxy)butyl)-4-(N-hydroxycarbamimidoyl)-piperidine-1-carboxylate. Following the procedure for Intermediate 14 using Intermediate 94 gave the title compound as colorless oil (12.8 g) that was carried on without further purification. $^1$H NMR (300 MHz, CDCl$_3$) δ: 7.35-7.27 (5H, m), 5.60 (2H, bs), 5.08 (2H, d, J=2.9 Hz), 3.85-3.81 (2H, m), 3.57-3.53 (2H, m), 3.16-3.09 (2H, m), 1.97-1.88 (2H, m), 1.53-1.38 (6H, m), 1.33-1.26 (2H, m), 0.84 (9H, s), −0.01 (6H, s). LCMS (M+H): 464.22.

Intermediate 96

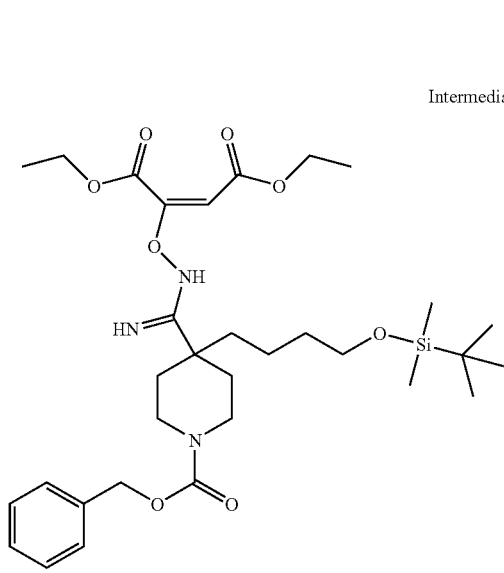

Diethyl 2-(1-(benzyloxycarbonyl)-4-(4-(tert-butyldimethylsilyloxy)butyl)-piperidine-4-carboximidamidooxy)maleate. Following the procedure for Intermediate 15 using Intermediate 95 gave the title compound as pale yellow oil (2.47 g, 11% yield over 2 steps). $^1$H NMR (300 MHz, CDCl$_3$) δ: 7.33-7.28 (5H, m), 5.08 (2H, s), 4.72 (1H, s), 4.35-4.05 (4H, m), 3.85 (2H, bs), 3.55 (2H, t, J=6.0 Hz), 3.14 (2H, bs), 1.98-1.93 (2H, m), 1.47-1.20 (14H, m), 0.84 (9H, s), 0.00 (6H, s). LCMS (M+H): 634.23.

Intermediate 97

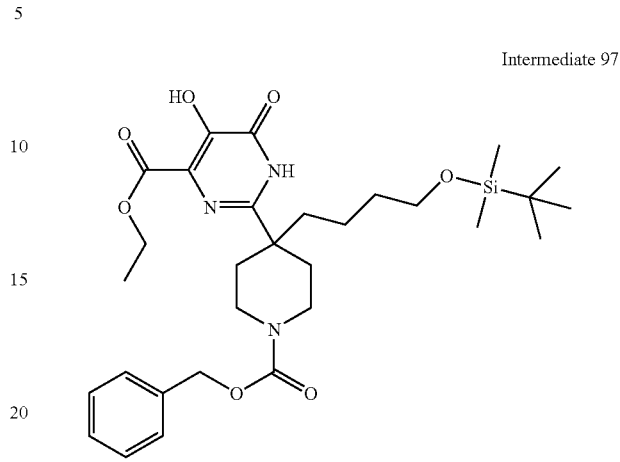

Ethyl 2-(1-(benzyloxycarbonyl)-4-(4-(tert-butyldimethylsilyloxy)butyl)-piperidin-4-yl)-5-hydroxy-6-oxo-1,6-dihydropyrimidine-4-carboxylate. Following the procedure for Intermediate 16 using Intermediate 96 gave the title compound as yellow oil (0.39 g, 17% yield). LCMS (M+H): 588.11.

Intermediate 98

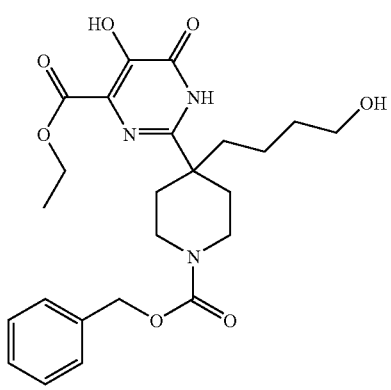

Ethyl 2-(1-(benzyloxycarbonyl)-4-(4-hydroxybutyl)piperidin-4-yl)-5-hydroxy-6-oxo-1,6-dihydropyrimidine-4-carboxylate. To a solution of Intermediate 97 (0.39 g, 0.67 mmol) in THF (4 mL) cooled to 0° C. was added TBAF (2.68 mL, 2.68 mmol, 1M in THF) and the resulting solution was stirred at room temperature for 4 h. The mixture was diluted with EtOAc and washed with water and dried (Na$_2$SO$_4$). After concentration, the residue was purified (YMC Combiprep ODS-A, 30 mm×50 mm, MeOH/H$_2$O/0.1% TFA) to give the title compound as a white foam (0.18 g, 57% yield). $^1$H NMR (300 MHz, CDCl$_3$) δ: 11.72 (1H, bs), 10.76 (1H, bs), 7.33-7.27 (5H, m), 5.08 (2H, s), 4.40 (2H, q, J=6.9 Hz), 3.86-3.82 (2H, m), 3.55 (2H, t, J=6.2 Hz), 3.16 (2H, t, J=11.0 Hz), 2.80 (1H, bs), 2.29-2.24 (2H, m), 1.75-1.69 (2H, m), 1.64-1.55

(2H, m), 1.48-1.37 (2H, m), 1.39 (3H, t, J=7.1 Hz), 1.22-1.10 (2H, m). LCMS (M+H): 474.08.

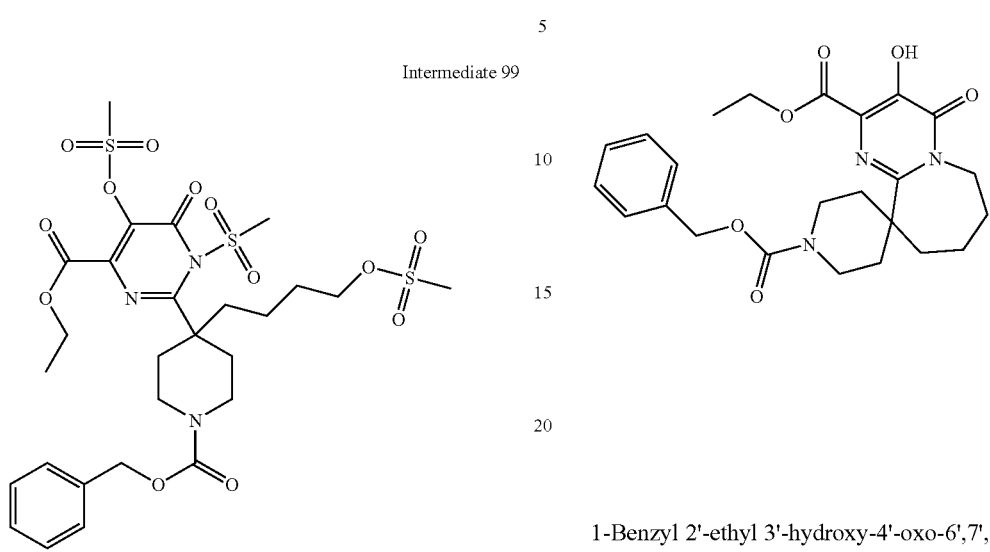

Intermediate 99

Ethyl 2-(1-(benzyloxycarbonyl)-4-(4-(methylsulfonyloxy)butyl)piperidin-4-yl)-1-(methylsulfonyl)-5-(methylsulfonyloxy)-6-oxo-1,6-dihydropyrimidine-4-carboxylate. Following the procedure for Intermediate 63 using Intermediate 98 gave the title compound as orange oil (0.096 g, 36% yield). LCMS (M+H): 708.09.

Intermediate 100

1-Benzyl 2'-ethyl 3'-hydroxy-4'-oxo-6',7',8',9'-tetrahydro-4'H-spiro-[piperidine-4,1'-pyrimido[1,2-a]azepine]-1,2'-dicarboxylate. Following the procedure for Intermediate 18 using Intermediate 99 gave the title compound as yellow foam (0.025 g, 40% yield). LCMS (M+H): 456.11.

The following examples in Table 6 were prepared according to the above procedure for Example 1 using appropriate intermediate and benzyl amine.

TABLE 6

| Example | Structure | Analytical data |
|---|---|---|
| 48 | 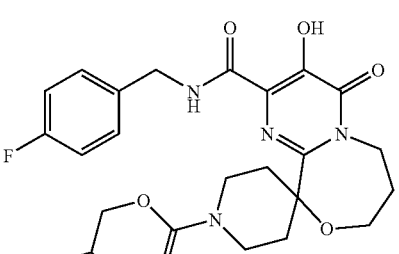<br>Benzyl 2'-(4-fluorobenzylcarbamoyl)-3'-hydroxy-4'-oxo-4',6',7',8'-tetrahydrospiro[piperidine-4,10'-pyrimido[2,1-c][1,4]oxazepine]-1-carboxylate | Yellow foam (0.7222 g, 61%, yield). $^1$H NMR(300 M Hz, CDCl$_3$) δ: 12.11(1H, s), 7.69(1H, t, J=6.4 Hz), 7.33-7.27(7H, m), 7.05-6.97(2H, m), 5.09(2H, s), 4.56-4.48(4H, m), 4.07(2H, d, J=13.2 Hz), 3.72-3.65(2H, m), 3.16(2H, t, J=13.2 Hz), 2.00-1.88(6H, m). HRMS(M + H) calcd for C$_{28}$H$_{30}$N$_4$O$_6$F: 537.2149; found: 537.2145. |

TABLE 6-continued

| Example | Structure | Analytical data |
|---------|-----------|-----------------|
| 49 | 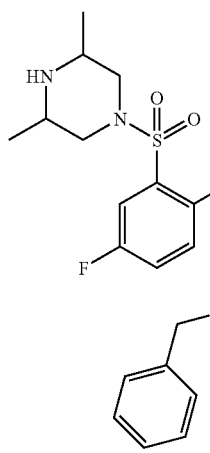 Benzyl 2'-(2-(3,5-dimethylpiperazin-1-yl-sulfonyl)-4-fluorobenzylcarbamoyl)-3'-hydroxy-4'-oxo-4',6',7',8'-tetrahydrospiro[piperidine-4,10'-pyrimido[2,1-c][1,4]oxazepine]-1-carboxylate | White foam. 32% yield. $^1$H NMR(500 M Hz, CDCl$_3$) δ: 11.87(1H, bs), 8.43(1H, t, J=6.7 Hz), 7.66(1H, dd, J=8.5, 5.2 Hz), 7.50(1H, dd, J=8.1, 2.6 Hz), 7.39-7.37(4H, m), 7.34-7.29(2H, m), 5.16(2H, s), 4.77(2H, s), 4.10-4.08(2H, m), 3.81(2H, d, J=11.9), 4.59-4.46(2H, m), 3.72-3.68(2H, m), 3.23-3.19(2H, m), 3.12(2H, t, J=12.7 Hz), 2.17-2.10(2H, m), 1.97-1.92(4H, m), 1.40(3H, s). HRMS (M + H) calcd for C$_{34}$H$_{42}$N$_6$O$_8$FS: 7.13.2769; found: 713.2786. |
| 50 | 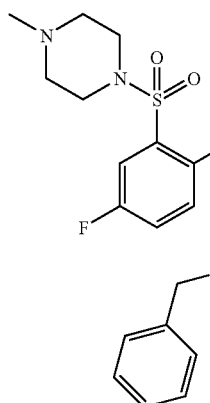 Benzyl 2'-(4-fluoro-2-(4-methyl-piperazin-1-ylsulfonyl)benzyl-carbamoyl)-3'-hydroxy-4'-oxo-4',6',7',8'-tetrahydrospiro[piperidine-4,10'-pyrimido[2,1-c][1,4]oxazepine]-1-carboxylate | White foam. 39% yield. $^1$H NMR(500 M Hz, CDCl$_3$) δ: 11.81(1H, bs), 8.54(1H, t, J=6.7 Hz), 7.67(1H, dd, J=8.1, 4.7 Hz), 7.45(1H, dd, J=7.9, 1.5 Hz), 7.40-7.29(6H, m), 5.16(2H, s), 4.76(2H, d, J=6.4 Hz), 4.08(2H, d, J=13.1 Hz), 3.94-3.91(2H, m), 3.85-3.65(4H, m), 3.50-3.46(2H, m), 3.28-3.03(8H, m), 2.81(3H, s), 2.03-1.90(4H, m). HRMS (M + H) calcd for C$_{33}$H$_{40}$N$_6$O$_8$FS: 699.2612; found: 699.2637. |

TABLE 6-continued

| Example | Structure | Analytical data |
|---|---|---|
| 51 | Benzyl 2'-(4-fluoro-2-(1,1-dioxo-1λ6-[1,2]thiazinan-2-yl)benzylcarbamoyl)-3'-hydroxy-4'-oxo-4',6',7',8'-tetrahydrospiro[piperidine-4,10'-pyrimido[2,1-c][1,4]oxazepine]-1-carboxylate | White solid. 39% yield. $^1$H NMR(500 M Hz, CDCl$_3$) δ: 7.49-7.46(1H, m), 7.32-7.28(5H, m), 7.13(1H, d, J=9.5 Hz), 7.05-7.02(1H, m), 5.14-5.04(4H, m), 4.92-4.89(2H, m), 4.29(2H, d, J=12.8 Hz), 4.09-4.00(4H, m), 3.79-3.62(4H, m), 3.42-3.34(2H, m), 3.18-3.07(4H, m), 3.18-3.15(4H, m), 1.96-1.82(4H, m). HRMS(M + H) calcd for C$_{32}$H$_{37}$N$_5$O$_8$FS: 670.2347; found: 670.2369. |
| 52 | Benzyl 2'-(4-fluoro-2-(morpholinosulfonyl)benzylcarbamoyl)-3'-hydroxy-4'-oxo-4',6',7',8'-tetrahydrospiro[piperidine-4,10'-pyrimido[2,1-c][1,4]oxazepine]-1-carboxylate | White foam. 30% yield. $^1$H NMR(500 M Hz, CDCl$_3$) δ: 11.90(1H, bs), 8.48(1H, t, J=6.7 Hz), 7.66(1H, dd, J=8.5, 5.2 Hz), 7.54(1H, dd, J=8.2, 2.4 Hz), 7.39-7.28(6H, m), 5.17(2H, s), 4.80(2H, d, J=7.0 Hz), 4.58-4.51(2H, m), 4.12-4.09(2H, m), 3.74-3.66(6H, m), 3.21-3.19(6H, m), 2.16-2.11(2H m), 1.96-1.91(4H, m). HRMS(M + H) calcd for C$_{32}$H$_{37}$N$_5$O$_9$FS: 686.2296; found: 686.2323. |
| 53 | Benzyl 2'-(4-fluoro-2-(5-methyl-1H-1,2,4-triazol-1-yl)benzylcarbamoyl)-3'-hydroxy-4'-oxo-4',6',7',8'-tetrahydrospiro[piperidine-4,10'-pyrimido[2,1-c][1,4]oxazepine]-1-carboxylate | Brown foam. 85% yield. $^1$H NMR(300 M Hz, CDCl$_3$) δ: 11.94(1H, bs), 8.52(1H, t, J=6.6 Hz), 8.01(1H, s), 7.62(1H, dd, J=8.6, 6.0 Hz), 7.32-7.26(5H, m), 7.19(1H, td, J=8.2, 2.7 Hz), 6.94(1H, dd, J=8.4, 2.6 Hz), 5.11(2H, d, J=22.3 Hz), 4.50(2H, bs), 4.24(2H, bs), 4.11(2H, bs), 3.66(2H, bs), 3.18(2H, bs), 2.43(3H, s), 2.19(2H, bs), 1.94-1.90(4H, m). HRMS(M + H) calcd for C$_{31}$H$_{33}$N$_7$O$_6$F: 618.2476; found: 618.2488. |

TABLE 6-continued

| Example | Structure | Analytical data |
|---|---|---|
| 54 | 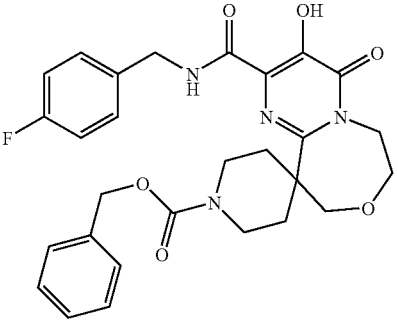 Benzyl 2'-(4-fluorobenzylcarbamoyl)-3'-hydroxy-4'-oxo-4',6',7',9'-tetrahydrospiro[piperidine-4,10'-pyrimido[1,2-d][1,4]oxazepine]-1-carboxylate | White solid. 3% yield. $^1$H NMR(300 M Hz, CDCl$_3$) δ: 12.01(1H, s), 7.61(1H, t, J=4.9 Hz), 7.31-7.25(6H, m), 7.01(2H, t, J=8.6 Hz), 5.09(2H, s), 4.56(2H, bs), 3.78-3.65(1H, m), 3.39-3.31(2H, m), 2.25-1.79(4H, m). HRMS(M + H) calcd for C$_{28}$H$_{30}$N$_4$O$_6$F: 537.2149; found: 537.2135. |
| 55 | 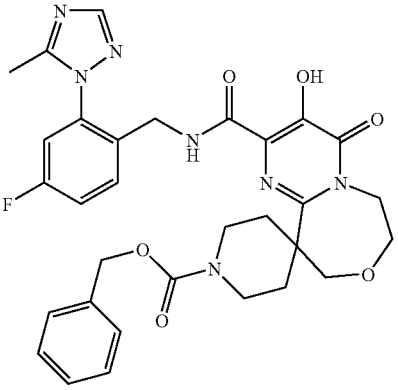 Benzyl 2'-(4-fluoro-2-(5-methyl-1H-1,2,4-triazol-1-yl)benzylcarbamoyl)-3'-hydroxy-4'-oxo-4',6',7',9'-tetrahydrospiro[piperidine-4,10'-pyrimido[1,2-d][1,4]oxazepine]-1-carboxylate | Yellow foam. 81% yield. $^1$H NMR(500 M Hz, CDCl$_3$) δ: 12.04(1H, s), 8.49(1H, t, J=5.8 Hz), 8.02(1H, s), 7.68-7.65(1H, m), 7.36-7.30(5H, m), 7.24-7.20(1H, m), 6.95(1H, d, J=7.6 Hz), 5.13-5.11(2H, m), 4.27(2H, d, J=14.6 Hz), 3.92-3.61(8H, m), 3.49-3.45(2H, m), 2.47(3H, s), 2.39-2.18(2H, m), 1.98-1.76(2H, m). HRMS(M + H) calcd for C$_{31}$H$_{33}$FN$_7$O$_6$: 618.2476; found: 618.2485. Anal. calcd for C$_{31}$H$_{32}$FN$_7$O$_6$•0.25 CH$_2$Cl$_2$: C, 58.75; H, 5.13; N, 15.35; found: C, 58.72; H, 4.83; N, 15.25. |
| 56 | 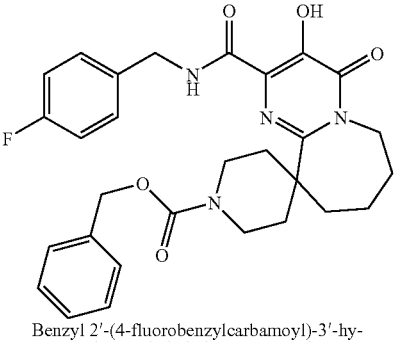 Benzyl 2'-(4-fluorobenzylcarbamoyl)-3'-hydroxy-4'-oxo-6',7',8',9'-tetrahydro-4'H-spiro[piperidine-4,10'-pyrimido[1,2-a]azepine]-1-carboxylate | White solid. 15% yield. $^1$H NMR(300 M Hz, CDCl$_3$) δ: 11.89(1H, s), 7.67(1H, t, J=6.4 Hz), 7.34-7.26(6H, m), 7.04-6.98(2H, m), 5.09(2H, s), 4.56(2H, d, J=6.22 Hz), 4.59-4.29(2H, m), 3.80-3.73(2H, m), 3.34-3.25(2H, m), 2.27-2.01(2H, m), 1.80-1.68(6H, m), 1.53(2H, bs). HRMS (M + H) calcd for C$_{29}$H$_{32}$N$_4$O$_5$F: 535.2358; found: 535.2341. |

Intermediate 101

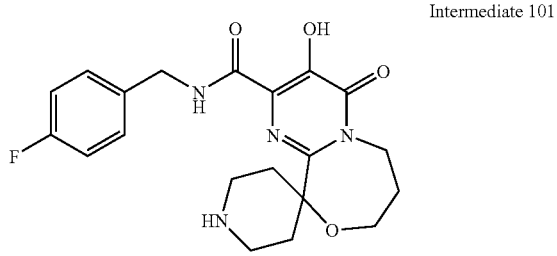

N-(4-Fluorobenzyl)-3'-hydroxy-4'-oxo-4',6',7',8'-tetrahydrospiro[piperidine-4,10'-pyrimido[2,1-c][1,4]oxazepine]-2'-carboxamide. To a solution of the Example 48 (0.7222 g, 1.35 mmol) in $CH_2Cl_2$ (10 mL) was added HBr/HOAc (10 mL, 5.5 mmol, 5.5 M solution). The resulting suspension was stirred at room temp for 3 h. The solids were collected by filtration and dried under vacuum to give the title compound as a pale brown solid (0.5646 g, 86% yield). $^1$H NMR (300 MHz, DMSO) δ: 12.24 (1H, s), 9.11 (1H, t, J=6.4 Hz), 8.58 (1H, bs), 7.42-7.37 (2H, m), 7.20-7.14 (2H, m), 4.50 (2H, d, J=6.6 Hz), 4.38 (2H, bs), 3.73 (2H, t, J=6.2 Hz), 3.27-3.22 (2H, m), 3.14-3.02 (2H, m), 2.56-2.45 (2H, m), 2.15 (2H, d, J=14.3 Hz), 1.92-1.85 (2H, m). HRMS (M+H) calcd for $C_{20}H_{24}N_4O_4F$: 403.1782; found: 403.1771. Anal calcd for $C_{20}H_{23}FN_4O_4 \cdot 1 HBr/0.2 H_2O$: C, 49.33; H, 5.05; N, 11.51; F, 3.90 found: C, 49.35; H, 4.99; N, 11.15; F, 3.53.

Intermediate 102

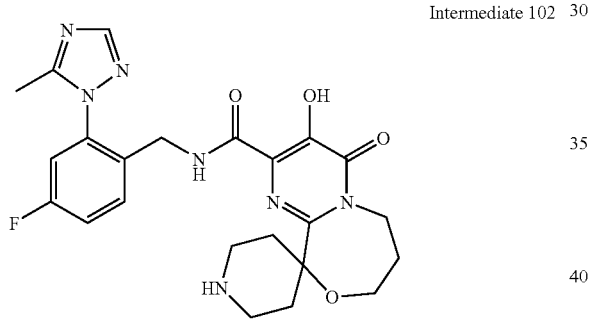

N-(4-Fluoro-2-(5-methyl-1H-1,2,4-triazol-1-yl)benzyl)-3'-hydroxy-4'-oxo-4',6',7',8'-tetrahydrospiro[piperidine-4,10'-pyrimido[2,1-c][1,4]oxazepine]-2'-carboxamide. Following the procedure for Example 101 using Example 53 gave the title compound as a yellow solid (63% yield). $^1$H NMR (500 MHz, MeOD) δ: 8.79 (1H, t, J=5.9 Hz), 8.75 (1H, s), 7.81-7.78 (1H, m), 7.39-7.35 (2H, m), 4.43 (2H, bs), 4.37 (2H, d, J=4.3 Hz), 3.72 (2H, t, J=5.9 Hz), 3.29-3.17 (4H, m), 2.66-2.61 (2H, m), 2.56 (3H, s), 2.18 (2H, d, J=15.0 Hz), 1.92 (2H, t, J=5.8 Hz). HRMS (M+H) calcd for $C_{23}H_{27}N_7O_4F$: 484.2109; found: 484.2125.

EXAMPLE 43 103

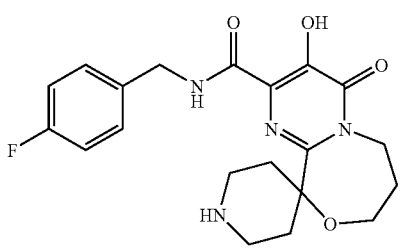

N-(4-Fluorobenzyl)-3'-hydroxy-4'-oxo-4',6',7',9'-tetrahydrospiro[piperidine-4,10'-pyrimido[1,2-d][1,4]oxazepine]-2'-carboxamide. Following the procedure for Intermediate 101 using Example 54 gave the title compound as brown powder (98% yield). LCMS (M+H) calcd for $C_{20}H_{24}FN_4O_4$: 403.17; found: 403.42.

EXAMPLE 104

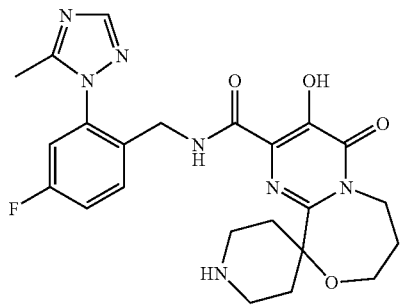

N-(4-Fluoro-2-(5-methyl-1H-1,2,4-triazol-1-yl)benzyl)-3'-hydroxy-4'-oxo-4',6',7',9'-tetrahydrospiro[piperidine-4,10'-pyrimido[1,2-d][1,4]oxazepine]-2'-carboxamide. Following the procedure for Example 101 using Example 55 gave the title compound as brown solid (81% yield). LCMS (M+H) calcd for $C_{23}H_{27}FN_7O_4$: 484.21; found: 484.47.

EXAMPLE 57

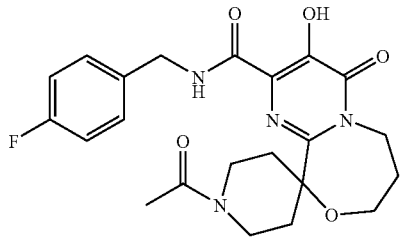

1-Acetyl-N-(4-fluorobenzyl)-3'-hydroxy-4'-oxo-4',6',7',8'-tetrahydrospiro-[piperidine-4,10'-pyrimido[2,1-c][1,4]oxazepine]-2'-carboxamide. To a mixture of Intermediate 101 (0.05 g, 0.10 mmol) and triethylamine (0.04 mL, 0.3 mmol) in $CH_2Cl_2$ (10 mL, was added acetic anhydride (0.01 mL, 0.11 mmol). The mixture was stirred at room temperature for 4 h and concentrated. Then, the resulting residue was triturated with EtOAc and $H_2O$, and the solids were collected by filtration to give the title compound as a white solid (0.0176 g, 40% yield). $^1$H NMR (300 MHz, CDCl$_3$) δ: 12.14 (1H, s), 7.70 (1H, bs), 7.32-7.27 (2H, m), 7.04-6.99 (2H, m), 4.66 (1H, bs), 4.56 (2H, d, J=5.9 Hz), 4.38 (1H, bs), 3.78-3.63 (4H, m), 3.50-3.41 (1H, m), 2.94-2.86 (1H, m), 2.07 (3H, s), 2.03-1.88 (6H, m). HRMS (M+H) calcd for $C_{22}H_{26}N_4O_5F$: 445.1887;

found: 445.1886. Anal calcd for $C_{22}H_{25}FN_4O_5 \cdot 0.5\ H_2O$: C, 58.27; H, 5.78; N, 12.35; F, 4.19 found: C, 58.34; H, 5.63; N, 12.19; F, 4.19.

EXAMPLE 58

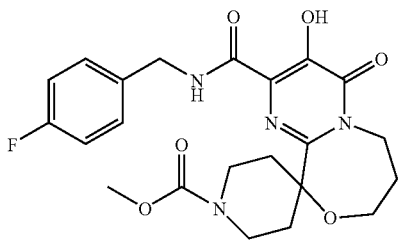

Methyl 2'-(4-fluorobenzylcarbamoyl)-3'-hydroxy-4'-oxo-4',6',7',8'-tetrahydrospiro[piperidine-4,10'-pyrimido[2,1-c][1,4]oxazepine]-1-carboxylate. To a mixture of Intermediate 101 (0.05 g, 0.10 mmol) and triethylamine (0.04 mL, 0.3 mmol) in $CH_2Cl_2$ (10 mL) was added methyl chloroformate (0.0085 mL, 0.110 mmol). The mixture was stirred at room temperature for 1 h and concentrated. The residue was purified by flash chromatography (eluting with 5% MeOH/$CH_2Cl_2$) to give the title compound as a white solid (0.0126 gm 27% yield). $^1$H NMR (500 MHz, CDCl$_3$) δ: 12.13 (1H, s), 7.71 (1H, t, J=5.9 Hz), 7.43-7.31 (2H,m), 7.06-7.03 (2H, m), 4.59 (2H, d, J=11.9 Hz), 4.59-4.51 (2H, m), 4.05 (2H, d, J=11.9 Hz), 3.69 (5H, bs), 3.17 (2H, t, J=13.0 Hz), 2.00-1.91 (6H, m). HRMS (M+H) calcd for $C_{22}H_{26}N_4O_6F$: 461.1836; found: 461.1847.

The following examples in Table 7 were prepared following the procedure for Examples 57-58 using the appropriate Intermediates and reagents.

TABLE 7

| Example | Structure | Analytical Data |
|---|---|---|
| 59 | N$^{2'}$-(4-Fluorobenzyl)-3'-hydroxy-N$^1$,N$^1$-di-methyl-4'-oxo-4',6',7',8'-tetra-hydrospiro[piperidine-4,10'-pyrimido[2,1-c][1,4]oxazepine]-1,2'-di-carboxamide | White solid. 63% yield. $^1$H NMR (500 M Hz, CDCl$_3$) δ: 12.14(1H, s), 7.88(1H, bs), 7.36-7.33(2H, m), 7.06-7.02(2H, m), 4.59(2H, d, J=6.4 Hz), 4.57-4.53(2H, m), 3.71(2H, bs), 3.63(2H, d, J=12.8 Hz), 3.26(2H, t, J=12.0 Hz), 2.84(6H, bs), 2.83-2.81(2H, m), 2.02-1.83(6H, m), HRMS(M + H) calcd for $C_{23}H_{29}N_5O_5F$: 474.2153; found: 474.2148. |
| 60 | N-(4-Fluorobenzyl)-3'-hydroxy-1-(meth-ylsulfonyl)-4'-oxo-4',6',7',8'-tetra-hydrospiro[piperidine-4,10'-pyri-mido[2,1-c][1,4]oxazepine]-2'-carbox-amide | White solid. 40% yield. $^1$H NMR (500 M Hz, CDCl$_3$) δ: 7.76(1H, t, J=6.1 Hz), 7.34-7.31(2H, m), 7.05-7.01(2H, m), 4.57(2H, d, J=6.4 Hz), 4.51(2H, bs), 3.70-3.68(4H, m), 3.05(2H, t, J=11.6 Hz), 2.65(3H, s), 2.27-2.24(2H, m), 2.04(2H, d, J=13.4 Hz), 1.98(2H, t, J=5.8 Hz). HRMS(M + H) calcd for $C_{21}H_{26}N_4O_6FS$: 481.1557; found: 481.1574. |
| 61 | 1-(N,N-Dimethylsulfamoyl)-N-(4-fluoro-benzyl)-3'-hydroxy-4'-oxo-4',6',7',8'-tetra-hydrospiro-[pipe-ridine-4,10'-pyrimido[2,1-c][1,4]oxa-zepine]-2'-carboxamide | White solid. 69% yield. $^1$H NMR (500 M Hz, CDCl$_3$) δ: 12.14(1H, bs), 7.74(1H, t, J=5.8 Hz), 7.35-7.32(2H, m), 7.06-7.03(2H, m), 4.60(2H, d, J=6.4 Hz), 4.55(2H, bs), 3.70-3.64(4H, m) 3.23(2H, t, J=12.5 Hz), 2.82(6H, s), 2.23(2H, bs), 2.00-1.95(4H, m). HRMS(M + H) calcd for $C_{22}H_{29}N_5O_6FS$: 510.1823; found: 510.1817. |

TABLE 7-continued

| Example | Structure | Analytical Data |
|---|---|---|
| 62 | 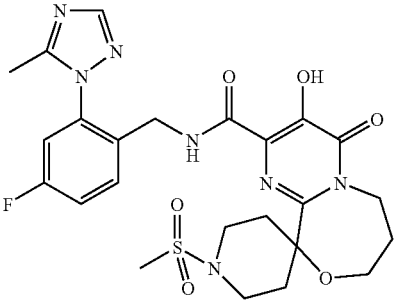<br>N-(4-Fluoro-2-(5-methyl-1H-1,2,4-triazol-1-yl)benzyl)-3'-hydroxy-1-(methylsulfonyl)-4'-oxo-4',6',7',8'-tetrahydrospiro[piperidine-4,10'-pyrimido[2,1-c][1,4]oxazepine]-2'-carboxamide | Pale brown solid. 28% yield. $^1$H NMR(500 M Hz, CDCl$_3$) δ: 12.03(1H, bs), 8.63(1H, s), 8.22(1H, s), 7.72-7.69(1H, m), 7.25-7.22(1H, m), 7.06-7.04(1H, m), 4.53(2H, bs), 4.33(2H, s), 3.74-3.72(4H, m), 3.07(2H, t, J=11.1 Hz), 2.81(3H, s), 2.55(3H, s), 2.48(2H, bs), 2.07(2H, d, J=10.4 Hz), 1.99(2H, bs). HRMS (M + H) calcd for C$_{24}$H$_{29}$N$_7$O$_6$FS: 562.1884; found: 562.1873. Anal calcd for C$_{24}$H$_{28}$FN$_7$O$_6$S•0.5H$_2$O: C, 50.52; H, 5.12; N, 17.18; found: C, 50.70; H, 5.29; N, 16.82. |
| 63 | 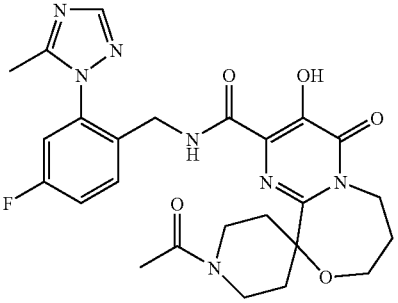<br>1-Acetyl-N-(4-fluoro-2-(5-methyl-1H-1,2,4-triazol-1-yl)benzyl)-3'-hydroxy-4'-oxo-4',6',7',8'-tetrahydrospiro[piperidine-4,10'-pyrimido[2,1-c][1,4]oxazepine]-2'-carboxamide | White solid. 25% yield. $^1$H NMR (500 M Hz, CDCl$_3$) δ: 11.98(1H, s), 8.44(1H, t, J=6.7 Hz), 8.19(1H, s), 7.69(1H, dd, J=8.5, 5.8 Hz), 7.26(1H, dd, J=8.5, 2.4 Hz), 7.05(1H, dd, J=8.2, 2.4 Hz), 4.59(2H, bs), 4.31(2H, d, J=36.9 Hz), 3.27(4H, bs), 3.00-2.94(2H, m), 2.53(2H, s), 2.28-2.19(2H, m), 2.15(3H, m), 1.99(4H, bs). HRMS(M + H) calcd for C$_{25}$H$_{29}$N$_7$O$_5$F: 516.2214; found: 526.2214. |
| 64 | 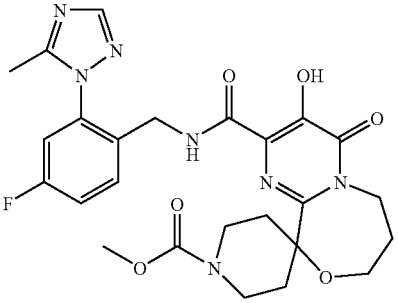<br>Methyl 2'-(4-fluoro-2-(5-methyl-1H-1,2,4-triazol-1-yl)benzylcarbamoyl)-3'-hydroxy-4'-oxo-4',6',7',8'-tetrahydrospiro[piperidine-4,10'-pyrimido[2,1-c][1,4]oxazepine]-1-carboxylate | White solid. 13% yield. $^1$H NMR (500 M Hz, CDCl$_3$) δ: 11.98(1H, s), 8.40(1H, bs), 8.27(1H, s), 7.71(1H, dd, J=8.4 Hz), 7.30(1H, t, J=7.8 Hz), 7.05(1H, d, J=6.7 Hz), 4.54(2H, bs), 4.37(2H, bs), 4.11-4.08(2H, m), 3.74(3H, s), 3.71(2H, bs), 3.22(2H, t, J=12.0 Hz), 2.60(3H, s), 2.19-2.16(2H, m), 1.99-1.95(4H, m). HRMS (M + H) calcd for C$_{25}$H$_{29}$N$_7$O$_6$F: 542.2163; found: 542.2145. |

TABLE 7-continued

| Example | Structure | Analytical Data |
|---|---|---|
| 65 | 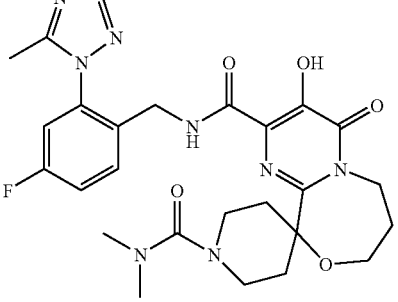<br>N2'-(4-Fluoro-2-(5-methyl-1H-1,2,4-triazol-1-yl)benzyl)-3'-hydroxy-N1,N1-dimethyl-4'-oxo-4',6',7',8'-tetrahydrospiro[piperidine-4,10'-pyrimido[2,1-c][1,4]oxazepine]-1,2'-dicarboxamide | White solid. 17% yield. $^1$H NMR (500 M Hz, CDCl$_3$) δ: 11.99(1H, s), 8.39(2H, s), 7.70(1H, t, J=6.7 Hz), 7.30(1H, t, J=7.6 Hz), 7.05(1H, d, J=7.0 Hz), 4.54(2H, bs), 4.32(2H, s), 3.70-3.67(4H, m), 3.34(2H, t, J=12.4 Hz), 2.88(6H, s), 2.59(3H, s), 2.25(2H, bs), 1.99-1.93(4H, m). Anal calcd for C$_{26}$H$_{31}$FN$_8$O$_5$•1.8TFA: C, 46.79; H, 4.35; N, 14.75; found: C, 46.66; H, 4.35; N, 14.69. |
| 66 | 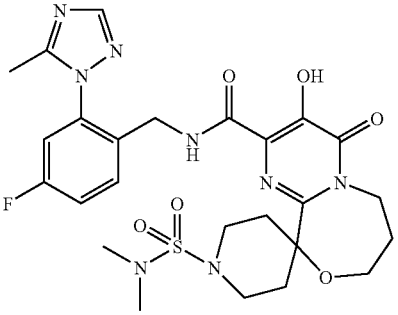<br>1-(N,N-Dimethylsulfamoyl)-N-(4-fluoro-2-(5-methyl-1H-1,2,4-triazol-1-yl)benzyl)-3'-hydroxy-4'-oxo-4',6',7',8'-tetrahydrospiro-[piperidine-4,10'-pyrimido[2,1-c][1,4]oxazepine]-2'-carboxamide | White solid. 33% yield. $^1$H NMR (500 M Hz, CDCl$_3$) δ: 12.02(1H, s), 8.55(1H, bs), 8.43(1H, bs), 7.71(1H, bs), 7.04(1H, bs), 4.54(2H, bs), 4.33(2H, bs), 3.27(2H, bs), 2.83(6H, s), 2.58(3H, bs), 2.40(2H, bs), 1.99(4H, bs). HRMS(M + H) calcd for C$_{25}$H$_{32}$N$_8$O$_6$FS: 591.2150; found; 591.2158. |
| 67 | 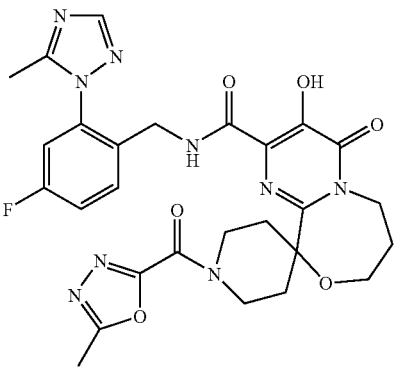<br>N-(4-Fluoro-2-(5-methyl-1H-1,2,4-triazol-1-yl)benzyl)-3'-hydroxy-1-(5-methyl-1,3,4-oxadiazole-2-carbonyl)-4'-oxo-4',6',7',8'-tetrahydrospiro[piperidine-4,10'-pyrimido[2,1-c][1,4]oxazepine]-2'-carboxamide | Yellow solid. 14% yield. $^1$H NMR(500 M Hz, CDCl$_3$) δ: 12.01(1H, s), 8.39(2H, s), 7.74-7.72(1H, m), 7.29-7.25(1H, m), 7.09-7.08(1H, m), 4.95(1H, d, J=12.2 Hz), 4.65(1H, d, J=12.5 Hz), 4.56(2H, bs), 4.34(2H, s), 3.75(2H, bs), 3.61(1H, t, J=13.3 Hz), 3.25(1H, t, J=12.7 Hz), 2.64-2.60(6H, m), 2.36(2H, bs), 2.10(2H, d, J=13.1 Hz), 2.02-2.00(2H, m). HRMS(M + H) calcd for C$_{27}$H$_{29}$N$_9$O$_6$F: 594.2225; found: 594.2228. Anal calcd for C$_{27}$H$_{28}$FN$_9$O$_6$•0.4TFA/0.8H$_2$O: C, 51.09; H, 4.63; N, 19.19; found: C, 51.41; H, 4.76; N, 18.91. |

TABLE 7-continued

| Example | Structure | Analytical Data |
|---|---|---|
| 68 | 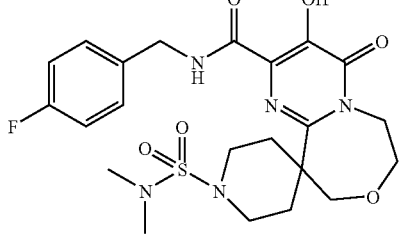<br>1-(N,N-Dimethylsulfamoyl)-N-(4-fluoro-benzyl)-3'-hydroxy-4'-oxo-4',6',7',9'-tetra-hydrospiro[piperidine-4,10'-pyrimido[1,2-d][1,4]oxazepine]-2'-carbox-amide | White solid. 14% yield. $^1$H NMR (500 M Hz, CDCl$_3$) δ: 12.04(1H, s), 7.62(1H, s), 7.34-7.30(2H, m), 7.08-7.03(2H, m), 4.60(2H, d, J=5.5 Hz), 3.77(4H, bs), 3.42(2H, bs), 3.23-3.19(2H, m), 2.78(3H, s), 2.79(3H, s), 2.26(2H, bs), 1.91(2H, bs), 1.57(2H, bs). HRMS(M + H) calcd for C$_{22}$H$_{29}$N$_5$O$_6$F: 510.1823; found: 510.1815. |
| 69 | 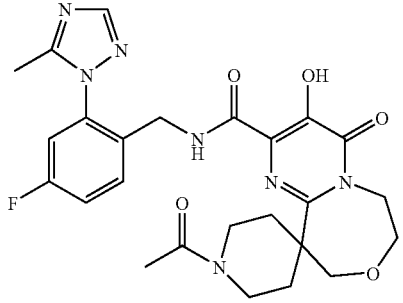<br>1-Acetyl-N-(4-fluoro-2-(5-methyl-1H-1,2,4-tri-azol-1-yl)benzyl)-3'-hy-droxy-4'-oxo-4',6',7',9'-tetra-hydrospiro[piperidine-4,10'-pyri-mido[1,2-d][1,4]oxazepine]-2'-carbox-amide | Brown glass. 24% yield. LCMS (M + H) calcd for C$_{25}$H$_{29}$FN$_7$O$_5$: 526.22; found: 526.52. Anal calcd for C$_{25}$H$_{28}$FN$_7$O$_5$·1.6TFA/0.4hexane: C, 49.50; H, 4.78; N, 13.21; found: C. 49.43; H, 4.43; N, 13.11. |
| 70 | 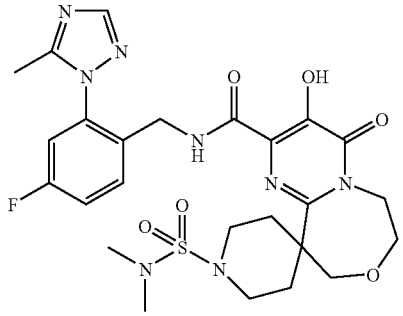<br>1-(N,N-Dimethylsulfamoyl)-N-(4-fluor-o-2-(5-methyl-1H-1,2,4-triazol-1-yl)ben-zyl)-3'-hydroxy-4'-oxo-4',6',7',9'-tetra-hydrospiro-[pipe-ridine-4,10'-pyrimido[1,2-d][1,4]oxa-zepine]-2'-carboxamide | White solid. 22% yield. $^1$H NMR (300 M Hz, CDCl$_3$) δ: 12.04(1H, bs), 8.50(1H, t, J=6.0 Hz), 8.03(1H, s), 7.65(1H, dd, J=8.8, 5.8 Hz), 7.21(1H, td, J=8.2, 2.7 Hz), 6.99(1H, dd, J=8.2, 2.7 Hz), 4.26(2H, d, J=6.2 Hz), 3.73(4H, bs), 3.37(2H, bs), 3.29-3.21(2H, m), 2.74(6H, s), 2.46(3H, s), 2.39(2H, bs), 1.92(2H, bs), 1.22(2H, bs). LCMS(M + H) calcd for C$_{25}$H$_{33}$FN$_8$O$_6$S: 591.21; found: 591.64. Anal calcd for C$_{25}$H$_{31}$FN$_8$O$_6$S·1 Na: C, 49.02; H, 4.94; N, 18.29; F, 3.10; found: C, 48.88; H, 4.70; N, 18.22; F, 3.01. |

TABLE 7-continued

| Example | Structure | Analytical Data |
|---|---|---|
| 71 | 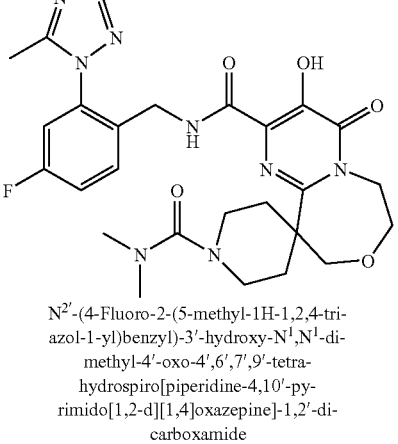<br>N2'-(4-Fluoro-2-(5-methyl-1H-1,2,4-triazol-1-yl)benzyl)-3'-hydroxy-N1,N1-dimethyl-4'-oxo-4',6',7',9'-tetrahydrospiro[piperidine-4,10'-pyrimido[1,2-d][1,4]oxazepine]-1,2'-dicarboxamide | Purple solid. 31% yield. $^1$H NMR (500 M Hz, CDCl$_3$) δ: 12.04(1H, s), 8.55(1H, t, J=6.2 Hz), 8.06(1H, s), 7.68(1H, dd, J=8.4, 5.9 Hz), 7.23(1H, td, J=8.2, 2.3 Hz), 7.01(1H, dd, J=8.2, 2.4 Hz), 4.28(2H, s), 3.78(4H, bs), 3.42(2H, bs), 3.24(2H, t, J=10.4 Hz), 2.80(6H, s) 2.48(3H, s), 2.40-1.64(6H, m). LCMS(M + H) calcd for C$_{26}$H$_{32}$FN$_8$O$_5$: 555.24; found: 555.70. Anal calcd for C$_{26}$H$_{31}$FN$_8$O$_5$•0.05 TFA: C, 55.95; H, 5.59; N, 20.00; found: C, 55.63; H, 5.91; N, 20.28. |
| 72 | 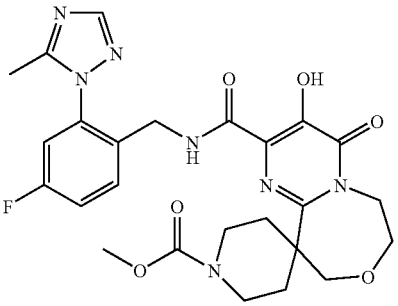<br>Methyl 2'-(4-fluoro-2-(5-methyl-1H-1,2,4-triazol-1-yl)benzylcarbamoyl)-3'-hydroxy-4'-oxo-4',6',7',9'-tetrahydrospiro[piperidine-4,10'-pyrimido[1,2-d][1,4]oxazepine]-1-carboxylate | Pale pink solid. 52% yield. $^1$H NMR(500 M Hz, CDCl$_3$) δ: 12.04(1H, s), 8.51(1H, t, J=5.8 Hz), 8.06(1H, s), 7.69(1H, dd, J=8.2, 6.1 Hz), 7.24(1H, td, J=9.4, 1.2 Hz), 7.02(1H, dd, J=8.4, 2.3 Hz), 4.28(2H, bs), 3.84-3.67(4H, m), 3.71(3H, s), 3.42(2H, t, J=9.9 Hz), 2.50(3H, s), 2.36-1.74(6H, m), 1.28-1.25(2H, m). LCMS(M + H) calcd for C$_{25}$H$_{29}$FN$_7$O$_6$: 542.21; found: 542.44. Anal calcd for C$_{25}$H$_{28}$FN$_7$O$_6$•1 TFA/0.2hexane: C, 50.34; H, 4.76; N, 14.57; found: C, 50.02; H, 4.94; N, 14.38. |
| 73 | 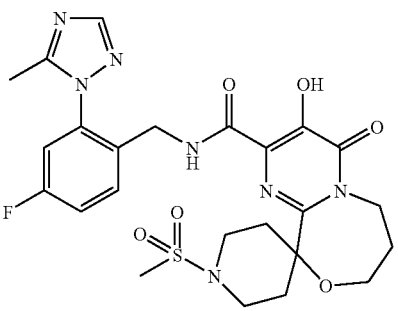<br>N-(4-Fluoro-2-(5-methyl-1H-1,2,4-triazol-1-yl)benzyl)-3'-hydroxy-1-(methylsulfonyl)-4'-oxo-4',6',7',9'-tetrahydrospiro[piperidine-4,10'-pyrimido[1,2-d][1,4]oxazepine]-2'-carboxamide | Brown solid. 22% yield. $^1$H NMR(500 M Hz, CDCl$_3$) δ: 12.05(1H, s), 8.47(1H, t, J=6.1 Hz), 8.06(1H, s), 7.69(1H, dd, J=8.5, 6.1 Hz), 7.24(1H, td, J=9.9, 2.1 Hz), 7.03(1H, dd, J=8.2, 2.1 Hz), 4.28(2H, d, J=6.7 Hz), 3.76(2H, bs), 3.40(2H, bs), 3.26(2H, t, J=8.5 Hz), 2.70(3H, s), 2.49(3H, s), 2.00-1.66(6H, m), 1.29-1.25(2H, m). LCMS(M + H) calcd for C$_{24}$H$_{29}$FN$_7$O$_6$S: 562.18; found: 562.41. |

EXAMPLE 74

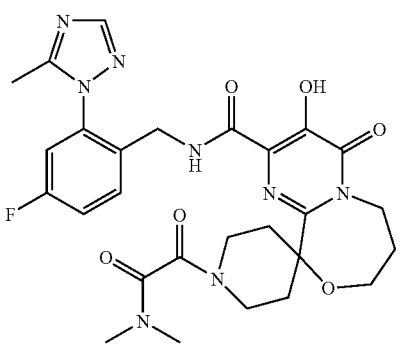

1-(2-(Dimethylamino)-2-oxoacetyl)-N-(4-fluoro-2-(5-methyl-1H-1,2,4-triazol-1-yl)benzyl)-3'-hydroxy-4'-oxo-4', 6',7',8'-tetrahydrospiro[piperidine-4,10'-pyrimido[2,1-c][1, 4]oxazepine]-2'-carboxamide. A solution of N-methylmorpholine (0.053 mL, 0.48 mmol) and N, N-dimethyloxamic acid (0.052 g, 0.44 mmol) in $CH_2Cl_2$ (2 mL) stirred for 5 min and then isopropyl chloroformate (0.4 mL, 0.4 mmol, 1M in toluene) was added and the mixture was stirred at room temperature for 2 h.

The above solution (1.4 mL, 0.25 mmol) was added to a mixture of Intermediate 102 (0.056 g, 0.1 mol) and diisopropylethylamine (0.1 mL, 0.68 mmol) in $CH_2Cl_2$ (10 mL). After stirring for 2 h, the solution was concentrated and purified (YMC Combiprep ODS-A, 30 mm×50 mm, MeOH/$H_2O$/0.1% TFA) to give the title compound as a white solid (0.0147 g, 25% yield). $^1$H NMR (300 MHz, $CDCl_3$) δ: 8.09 (2H, bs), 7.56-7.52 (1H, m), 7.05-6.98 (1H, m), 6.88 (1H, bs), 4.41 (2H, d, J=11.3 Hz), 4.15 (2H, bs), 3.56-3.45 (4H, m), 2.96 (3H, s), 2.93 (3H, s), 2.34 (3H, s), 2.19-1.73 (8H, m). HRMS (M+H) calcd for $C_{27}H_{32}N_8O_6F$: 583.2429; found: 583.2415. Anal calcd for $C_{24}H_{29}FN_4O_6S \cdot 1TFA/1.2 \ H_2O$: C, 48.50; H, 4.83; N, 15.60; found: C, 48.14; H, 4.96; N, 15.95.

EXAMPLE 75

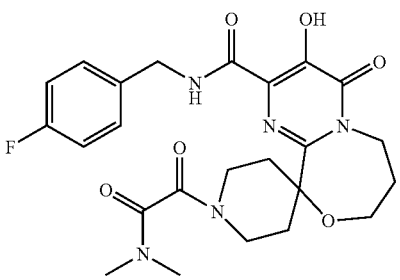

1-(2-(Dimethylamino)-2-oxoacetyl)-N-(4-fluorobenzyl)-3'-hydroxy-4'-oxo-4',6',7',8'-tetrahydrospiro[piperidine-4, 10'-pyrimido[2,1-c][1,4]oxazepine]-2'-carboxamide. Following the procedure for Example 74 using Intermediate 101 gave the title compound as a white solid (4% yield). $^1$H NMR (500 MHz, $CDCl_3$) δ: 12.24 (1H, s), 7.83 (1H, t, J=6.2 Hz), 7.35-7.33 (2H, m), 7.06-7.02 (2H, m), 4.65-4.54 (4H, m), 3.73 (2H, bs), 3.56-3.45 (2H, m), 3.00 (3H, s), 2.98 (3H, s), 2.25-2.13 (2H, m), 2.02-1.95 (4H, m). HRMS (M+H) calcd for $C_{24}H_{29}N_5O_6F$: 502.2102; found: 502.2078.

We claim:

1. A compound of Formula I

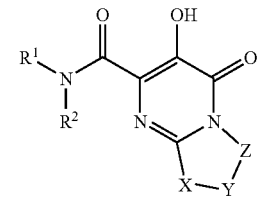

where:

$R^1$ is $(Ar^1)$alkyl;

$R^2$ is hydrogen, alkyl, hydroxy, or alkoxy;

$R^3$ is hydrogen, halo, hydroxy, cyano, alkyl, cycloalkyl, haloalkyl, alkoxy, haloalkoxy, $CON(R^6)(R^6)$, $CON(R^{11})(R^{12})$, $SOR^7$, $SO_2R^7$, $SO_2N(R^6)(R^6)$, $SO_2N(R^{11})(R^{12})$, $N(R^6)(R^6)$, $N(R^6)(R^6)$, $N(R^6)COR^7$, $N(R^6)CO_2R^7$, $N(R^6)SO_2R^7$, $PO(OR^6)_2$, $R^{16}$, or $Ar^2$;

$R^4$ is hydrogen, halo, hydroxy, cyano, alkyl, alkoxy, haloalkyl, or haloalkoxy;

$R^5$ is hydrogen, halo, hydroxy, cyano, alkyl, alkoxy, haloalkyl, or haloalkoxy;

$R^6$ is hydrogen or alkyl;

$R^7$ is alkyl or cycloalkyl;

$R^8$ and $R^9$ taken together is $CH_2N(R^{10})CH_2$, $CH_2N(R^{10})CH_2CH_2$, $CH_2N(R^{10})CH_2CH_2CH_2$, $CH_2N(R^{10})CH_2CH_2CH_2CH_2$, $CH_2CH_2N(R^{10})CH_2CH_2$, or $CH_2CH_2N(R^{10})CH_2CH_2CH_2$;

$R^{10}$ is $COR^6$, $CO_2(R^6)$, $COCO_2(R^6)$, $CON(R^6)(R^6)$, $COCON(R^6)(R^6)$, $CO_2(benzyl)$, $CO(phenyl)$, $SO_2R^7$, $SO_2N(R^6)(R^6)$, or $SO_2(phenyl)$ where the phenyl is substituted with 0-2 groups selected from alkyl, halo, haloalkyl, cyano, alkoxy, and haloalkoxy;

or $R^{10}$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of oxo, halo, alkyl, and alkoxy;

$R^{11}$ and $R^{12}$ taken together with the nitrogen to which they are attached is azetidinyl, pyrrolidinyl, $(R^6)$-piperidinyl, piperazinyl, dialkylpiperazinyl, $(R^{13})$-piperazinyl, $(R^{13})$-dialkylpiperazinyl, homopiperidinyl, morpholinyl, dialkylmorpholinyl, or thiomorpholinyl;

$R^{13}$ is alkyl, (cycloalkyl)alkyl, $SO_2R^{14}$, or $COR^{15}$;

$R^{14}$ is hydrogen, alkyl, amino, alkylamino, dialkylamino, azetidinyl, pyrrolidinyl, piperidinyl, hydroxypiperidinyl, piperizinyl, (alkyl)piperizinyl, morpholinyl, or thiomorpholinyl;

$R^{15}$ hydrogen, alkyl, hydroxy, alkoxy, amino, alkylamino, dialkylamino, azetidinyl, pyrrolidinyl, piperidinyl, hydroxypiperidinyl, piperizinyl, (alkyl)piperizinyl, morpholinyl, or thiomorpholinyl;

$R^{16}$ azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

Ar¹ is

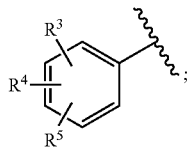

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of oxo, halo, alkyl, alkoxy, and $N(R^6)(R^6)$;

X—Y—Z is $C(R^8)(R^9)OCH_2CH_2$;

or a pharmaceutically acceptable salt thereof.

2. A compound of claim 1 where:

$R^{10}$ is $CO_2(R^6)$, $COCO_2(R^6)$, $CON(R^6)(R^6)$, $COCON(R^6)(R^6)$, $CO_2$(benzyl), CO(phenyl), $SO_2R^7$, $SO_2N(R^6)(R^6)$, or $SO_2$(phenyl) where the phenyl is substituted with 0-2 groups selected from alkyl, halo, haloalkyl, cyano, alkoxy, and haloalkoxy;

$R^{11}$ and $R^{12}$ taken together with the nitrogen to which they are attached is azetidinyl, pyrrolidinyl, $(R^6)$-piperidinyl, piperazinyl, $(R^{13})$-piperazinyl, homopiperidinyl, morpholinyl, or thiomorpholinyl; and X—Y—Z is $C(R^8)(R^9)OCH_2CH_2$;

or a pharmaceutically acceptable salt thereof.

3. A compound of claim 1 according to the following structure:

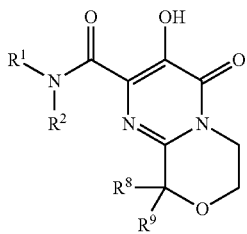

4. A compound of claim 1 where $R^1$ is $(Ar^1)$methyl.

5. A compound of claim 1 where $R^1$ is

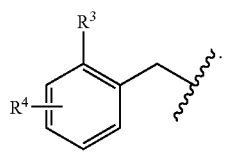

6. A compound of claim 1 where $R^1$ is

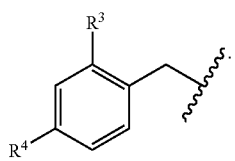

7. A compound of claim 6 where $R^3$ is fluoro, chloro, methyl, $CON(R^6)(R^6)$, or $Ar^2$ and $R^4$ is hydrogen, fluoro, chloro, or methyl.

8. A compound of claim 1 where $R^2$ is hydrogen.

9. A compound of claim 1 selected from the group consisting of 1-(N,N-Dimethylsulfamoyl)-N-(4-fluoro-2-(1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide;

1-(N,N-Dimethylsulfamoyl)-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide;

Methyl 2'-(4-fluoro-2-(1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate;

Methyl 2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-carboxylate;

$N^{2'}$-(4-Fluoro-2-(1H-1,2,4-triazol-1-yl)benzyl)-3'-hydroxy-$N^1$,$N^1$-dimethyl-4'-oxo-6',7'-dihydro-4'H-spiro[piperidine-4,9'-pyrimido[2,1-c][1,4]oxazine]-1,2'-dicarboxamide;

$N^{2'}$-(4-Fluorobenzyl)-3'-hydroxy-$N^1$,$N^1$-dimethyl-4'-oxo-6',7'-dihydro-4'H-spiro[piperidine-4,9'-pyrimido[2,1-c][1,4]oxazine]-1,2'-dicarboxamide;

N-(4-Fluoro-2-(1H-1,2,4-triazol-1-yl)benzyl)-3'-hydroxy-1-(methylsulfonyl)-4'-oxo-6',7'-dihydro-4'H-spiro[piperidine-4,9'-pyrimido[2,1-c][1,4]oxazine]-2'-carboxamide;

N-(4-Fluorobenzyl)-3'-hydroxy-1-(methylsulfonyl)-4'-oxo-6',7'-dihydro-4'H-spiro[piperidine-4,9'-pyrimido[2,1-c][1,4]oxazine]-2'-carboxamide;

1-Benzoyl-N-(4-fluoro-2-(1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide;

1-Benzoyl-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide;

N-(4-Fluoro-2-(1H-1,2,4-triazol-1-yl)benzyl)-3'-hydroxy-4'-oxo-1-tosyl-6',7'-dihydro-4'H-spiro[piperidine-4,9'-pyrimido[2,1-c][1,4]oxazine]-2'-carboxamide;

N-(1-(4-Fluorophenyl)ethyl)-3'-hydroxy-4'-oxo-1-tosyl-6',7'-dihydro-4'H-spiro[piperidine-4,9'-pyrimido[2,1-c][1,4]oxazine]-2'-carboxamide;

N-(4-Fluoro-2-(morpholinosulfonyl)benzyl)-3'-hydroxy-4'-oxo-1-tosyl-6',7'-dihydro-4'H-spiro[piperidine-4,9'-pyrimido[2,1-c][1,4]oxazine]-2'-carboxamide;

N-(4-Fluoro-2-(3-methyl-1H-1,2,4-triazol-1-yl)benzyl)-3'-hydroxy-4'-oxo-1-tosyl-6',7'-dihydro-4H-spiro[piperidine-4,9'-pyrimido[2,1-c][1,4]oxazine]-2'-carboxamide;

N-(4-Fluoro-2-(5-methyl-1H-1,2,4-triazol-1-yl)benzyl)-3'-hydroxy-4'-oxo-1-tosyl-6',7'-dihydro-4'H-spiro[piperidine-4,9'-pyrimido[2,1-c][1,4]oxazine]-2'-carboxamide;

N-(2-(3,5-Dimethyl-1H-1,2,4-triazol-1-yl)-4-fluorobenzyl)-3'-hydroxy-4'-oxo-1-tosyl-6',7'-dihydro-4'H-spiro[piperidine-4,9'-pyrimido[2,1-c][1,4]oxazine]-2'-carboxamide;

1-(5-Fluoro-2-methylphenylsulfonyl)-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide;

N-(4-Fluoro-2-(1H-1,2,4-triazol-1-yl)benzyl)-1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxamide;

N-(4-Fluoro-2-(3-methyl-1H-1,2,4-triazol-1-yl)benzyl)-1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxamide;

N-(4-Fluoro-2-(5-methyl-1H-1,2,4-triazol-1-yl)benzyl)-1-(5-fluoro-2-methylphenylsulfonyl)-3'-hydroxy-4'-oxo-6',7'-dihydro-4'H-spiro[piperidine-4,9'-pyrimido[2,1-c][1,4]oxazine]-2'-carboxamide;

Benzyl 2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-carboxylate;

Benzyl 2'-(4-fluoro-2-(5-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate;

Benzyl 2'-(4-fluoro-2-(3-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate;

Methyl 2-(2'-(4-fluoro-2-(5-methyl-1H-1,2,4-triazol-1-yl)benzylcarbamoyl)-3'-hydroxy-4'-oxo-6',7'-dihydro-4'-spiro[piperidine-4,9'-pyrimido[2,1-c][1,4]oxazine]-1-yl)-2-oxoacetate;

1-(2-(Dimethylamino)-2-oxoacetyl)-N-(4-fluoro-2-(5-methyl-1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide;

Methyl 2-(2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-yl)-2-oxoacetate;

2-(2'-(4-Fluorobenzylcarbamoyl)-3'-hydroxy-4'-oxo-6',7'-dihydro-4'H-spiro[piperidine-4,9'-pyrimido[2,1-c][1,4]oxazine]-1-yl)-2-oxoacetic acid;

1-(2-(Dimethylamino)-2-oxoacetyl)-N-(4-fluorobenzyl)-3'-hydroxy-4'-oxo-6',7'-dihydro-4'H-spiro[piperidine-4,9'-pyrimido[2,1-c][1,4]oxazine]-2'-carboxamide;

Ethyl 2'-(4-fluorobenzylcarbamoyl)-3'-hydroxy-4'-oxo-6',7'-dihydro-4'H-spiro[piperidine-4,9'-pyrimido[2,1-c][1,4]oxazine]-1-carboxylate;

1-(2-(Dimethylamino)-2-oxoacetyl)-N-(4-fluoro-2-(3-methyl-1H-1,2,4-triazol-1-yl)benzyl)-3'-hydroxy-4'-oxo-6',7'-dihydro-4'H-spiro[piperidine-4,9'-pyrimido[2,1-c][1,4]oxazine]-2'-carboxamide;

Ethyl 2'-(4-fluoro-2-(3-methyl-1H-1,2,4-triazol-1-yl)benzylcarbamoyl)-3'-hydroxy-4'-oxo-6',7'-dihydro-4'H-spiro[piperidine-4,9'-pyrimido[2,1-c][1,4]oxazine]-1-carboxylate;

Benzyl 2-(4-fluorobenzylcarbamoyl)-3-hydroxy-4-oxo-6,7-dihydro-4H-spiro[pyrimido[2,1-c][1,4]oxazine-9,3'-pyrrolidine]-1'-carboxylate;

Benzyl 2-(4-fluoro-2-(5-methyl-1H-1,2,4-triazol-1-yl)benzylcarbamoyl)-3-hydroxy-4-oxo-6,7-dihydro-4H-spiro[pyrimido[2,1-c][1,4]oxazine-9,3'-pyrrolidine]-1'-carboxylate;

N-(4-Fluorobenzyl)-3-hydroxy-1'-(methylsulfonyl)-4-oxo-6,7-dihydro-4H-spiro[pyrimido[2,1-c][1,4]oxazine-9,3'-pyrrolidine]-2-carboxamide;

N-(4-Fluoro-2-(5-methyl-1H-1,2,4-triazol-1-yl)benzyl)-3-hydroxy-1'-(methylsulfonyl)-4-oxo-6,7-dihydro-4H-spiro[pyrimido[2,1-c][1,4]oxazine-9,3'-pyrrolidine]-2-carboxamide;

1'-(2-(Dimethylamino)-2-oxoacetyl)-N-(4-fluorobenzyl)-3-hydroxy-4-oxo-6,7-dihydro-4H-spiro[pyrimido[2,1-c][1,4]oxazine-9,3'-pyrrolidine]-2-carboxamide;

1'-(2-(Dimethylamino)-2-oxoacetyl)-N-(4-fluoro-2-(5-methyl-1H-1,2,4-triazol-1-yl)benzyl)-3-hydroxy-4-oxo-6,7-dihydro-4H-spiro[pyrimido[2,1-c][1,4]oxazine-9,3'-pyrrolidine]-2-carboxamide;

Isopropyl 2-(4-fluorobenzylcarbamoyl)-3-hydroxy-4-oxo-6,7-dihydro-4H-spiro[pyrimido[2,1-c][1,4]oxazine-9,3'-pyrrolidine]-1'-carboxylate;

Isopropyl 2-(4-fluoro-2-(5-methyl-1H-1,2,4-triazol-1-yl)benzylcarbamoyl)-3-hydroxy-4-oxo-6,7-dihydro-4H-spiro[pyrimido[2,1-c][1,4]oxazine-9,3'-pyrrolidine]-1'-carboxylate;

Ethyl 2-(2-(4-fluorobenzylcarbamoyl)-3-hydroxy-4-oxo-6,7-dihydro-4H-spiro[pyrimido[2,1-c][1,4]oxazine-9,3'-pyrrolidine]-1'-yl)-2-oxoacetate; and Ethyl 2-(2-(4-fluoro-2-(5-methyl-1H-1,2,4-triazol-1-yl)benzylcarbamoyl)-3-hydroxy-4-oxo-6,7-dihydro-4H-spiro[pyrimido[2,1-c][1,4]oxazine-9,3'-pyrrolidine]-1'-yl)-2-oxoacetate;

or a pharmaceutically acceptable salt thereof.

10. A composition comprising a therapeutic amount of a compound of claim 1 and a pharmaceutically acceptable carrier.

11. A method for treating HIV infection comprising administering a therapeutically effective amount of a compound of claim 1, or a pharmaceutically acceptable salt thereof, to a patient in need thereof.

* * * * *

UNITED STATES PATENT AND TRADEMARK OFFICE
CERTIFICATE OF CORRECTION

PATENT NO.       : 7,897,593 B2
APPLICATION NO.  : 11/754462
DATED            : March 1, 2011
INVENTOR(S)      : B. Narasimhulu Naidu et al.

It is certified that error appears in the above-identified patent and that said Letters Patent is hereby corrected as shown below:

In the Claims:

Claim 1:

Column 104, line 64, change "oxazolidonyl" to -- oxazolidinonyl --.

Claim 9:

Column 106, line 30, change "7-dihydro" to -- 7′-dihydro --.

Column 106, line 53, change "4H" to -- 4′H --.

Column 107, line 26, change "-4′-" to -- -4′H- --. (Second Occurrence)

Signed and Sealed this
Twenty-seventh Day of December, 2011

David J. Kappos
*Director of the United States Patent and Trademark Office*